US011450437B2

United States Patent
Ou et al.

(10) Patent No.: US 11,450,437 B2
(45) Date of Patent: Sep. 20, 2022

(54) HEALTH MANAGEMENT METHOD, APPARATUS, AND SYSTEM

(71) Applicant: TENCENT TECHNOLOGY (SHENZHEN) COMPANY LIMITED, Shenzhen (CN)

(72) Inventors: Pinfu Ou, Shenzhen (CN); Rongjun Li, Shenzhen (CN); Tianchang Yu, Shenzhen (CN); Zhenghua Huang, Shenzhen (CN); Shiping Li, Shenzhen (CN); Kai Qiu, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 819 days.

(21) Appl. No.: 15/840,401

(22) Filed: Dec. 13, 2017

(65) Prior Publication Data

US 2018/0114601 A1  Apr. 26, 2018

Related U.S. Application Data

(60) Continuation of application No. PCT/CN2016/096041, filed on Aug. 19, 2016, and a
(Continued)

(30) Foreign Application Priority Data

Sep. 24, 2015 (CN) .......................... 201510618806.1
Sep. 28, 2015 (CN) .......................... 201510628649.2
(Continued)

(51) Int. Cl.
*G16H 50/30* (2018.01)
*G16H 80/00* (2018.01)
(Continued)

(52) U.S. Cl.
CPC ............. *G16H 50/30* (2018.01); *G16H 10/60* (2018.01); *G16H 40/63* (2018.01); *G16H 40/67* (2018.01); *G16H 80/00* (2018.01)

(58) Field of Classification Search
CPC ........ G16H 50/30; G16H 40/67; G16H 10/60; G16H 40/63; G16H 80/00
See application file for complete search history.

(56) References Cited

U.S. PATENT DOCUMENTS 7,538,336 B2 *  5/2009  Brock .................. G01N 21/251
                                                    250/559.4
7,798,961 B1    9/2010  Bakhshandeh
(Continued)

FOREIGN PATENT DOCUMENTS

CN   1265194 A   8/2000
CN   1964789 A   5/2007
(Continued)

OTHER PUBLICATIONS

The State Intellectual Property Office of the People's Republic of China (SIPO) Office Action 1 for 201510672951.8 Apr. 23, 2018 9 Pages (including translation).
(Continued)

*Primary Examiner* — Evangeline Barr
(74) *Attorney, Agent, or Firm* — Anova Law Group, PLLC

(57) ABSTRACT

The present disclosure provides a method, an apparatus, and a system for health management. The method includes: receiving, from a graphical interface of a first user terminal, login information of a first user account, the first user terminal having a memory, a processor, and a measurement sensor; obtaining, by the first user terminal, physiological data of a user based on a measurement value detected by the measurement sensor; storing the physiological data into a medical record corresponding to the first user account; and
(Continued)

sending, by the first user terminal via a server, the physiological data to a second user terminal associated with the first user account remotely.

15 Claims, 43 Drawing Sheets

Related U.S. Application Data continuation of application No. PCT/CN2016/097242, filed on Aug. 29, 2016, and a continuation of application No. PCT/CN2016/097537, filed on Aug. 31, 2016, and a division of application No. PCT/CN2016/099440, filed on Sep. 20, 2016.

(30) Foreign Application Priority Data

| Oct. 16, 2015 | (CN) | 201510672951.8 |
| Nov. 2, 2015 | (CN) | 201510733090.X |

(51) Int. Cl.

| G16H 10/60 | (2018.01) |
| G16H 40/67 | (2018.01) |
| G16H 40/63 | (2018.01) |

(56) References Cited

U.S. PATENT DOCUMENTS

| | | | |
|---|---|---|---|
| 8,165,893 | B1 | 4/2012 | Goldberg et al. |
| 2007/0273902 | A1* | 11/2007 | Robinson ......... G01N 33/48771 358/1.9 |
| 2008/0118984 | A1 | 5/2008 | Yuan et al. |
| 2008/0314882 | A1 | 12/2008 | Bhullar et al. |
| 2009/0216558 | A1 | 8/2009 | Reisman et al. |
| 2009/0223287 | A1* | 9/2009 | Dai ................. G01N 33/48771 73/64.56 |
| 2010/0222648 | A1* | 9/2010 | Tan ...................... G16H 40/67 702/85 |
| 2010/0222649 | A1* | 9/2010 | Schoenberg ....... G06Q 30/0203 600/301 |
| 2011/0132774 | A1 | 6/2011 | Aum |
| 2012/0109676 | A1* | 5/2012 | Landau ................ G16H 40/67 705/2 |
| 2012/0122227 | A1* | 5/2012 | Wiegel ............ G01N 33/48771 436/95 |
| 2013/0160141 | A1* | 6/2013 | Tseng ..................... G06F 21/31 726/28 |
| 2013/0317859 | A1 | 11/2013 | Rao |
| 2014/0275948 | A1 | 9/2014 | Kamisoyama |
| 2015/0347701 | A1* | 12/2015 | Atkin ..................... G16H 10/40 705/2 |
| 2016/0077091 | A1* | 3/2016 | Tyrrell ............ G01N 33/48792 436/501 |
| 2016/0270717 | A1* | 9/2016 | Luna .................... A61B 5/7246 |

FOREIGN PATENT DOCUMENTS

| | | |
|---|---|---|
| CN | 201152977 Y | 11/2008 |
| CN | 101470878 A | 7/2009 |
| CN | 101609086 A | 12/2009 |
| CN | 101667224 A | 3/2010 |
| CN | 101766479 A | 7/2010 |
| CN | 101785701 A | 7/2010 |
| CN | 201662554 U | 12/2010 |
| CN | 201716292 U | 1/2011 |
| CN | 101981454 A | 2/2011 |
| CN | 102370459 A | 3/2012 |
| CN | 102509064 A | 6/2012 |
| CN | 102841118 A | 12/2012 |
| CN | 102954962 A | 3/2013 |
| CN | 102980932 A | 3/2013 |
| CN | 203025141 U | 6/2013 |
| CN | 103263294 A | 8/2013 |
| CN | 203365439 U | 12/2013 |
| CN | 103514357 A | 1/2014 |
| CN | 103532997 A | 1/2014 |
| CN | 103575774 A | 2/2014 |
| CN | 103718039 A | 4/2014 |
| CN | 104142402 A | 11/2014 |
| CN | 104318353 A | 1/2015 |
| CN | 104539813 A | 4/2015 |
| CN | 104639655 A | 5/2015 |
| CN | 104665795 A | 6/2015 |
| CN | 104688207 A | 6/2015 |
| CN | 104732468 A | 6/2015 |
| CN | 104767608 A | 7/2015 |
| CN | 105404769 A | 3/2016 |
| CN | 105426652 A | 3/2016 |
| CN | 105445447 A | 3/2016 |
| CN | 105468892 A | 4/2016 |
| TW | M304662 U | 1/2007 |
| WO | 2013040724 A1 | 3/2013 |

OTHER PUBLICATIONS

The World Intellectual Property Organization (WIPO) International Search Report for PCT/CN2016/096041 dated Oct. 31, 2016 7 Pages (including translation).
The World Intellectual Property Organization (WIPO) International Search Report for PCT/CN2016/097242 dated Sep. 30, 2016 8 Pages (including translation).
The World Intellectual Property Organization (WIPO) International Search Report for PCT/CN2016/099440 dated Dec. 26, 2016 7 Pages (including translation).
The World Intellectual Property Organization (WIPO) International Search Report for PCT/CN2016/097537 dated Dec. 5, 2016 6 Pages (including translation).
The State Intellectual Property Office of the People's Republic of China (SIPO) Office Action 1 for 201510618806.1 dated Jul. 12, 2017 8 Pages (including translation).
The State Intellectual Property Office of the People's Republic of China (SIPO) Office Action 2 for 201510618806.1, Nov. 8, 2017 8 Pages (including translation).
The State Intellectual Property Office of the People's Republic of China (SIPO) Office Action 1 for 201510672951.8 Sep. 1, 2017 8 Pages (including translation).
The State Intellectual Property Office of the People's Republic of China (SIPO) Office Action 1 for 201510628649.2 Jun. 27, 2017 11 Pages (including translation).
The State Intellectual Property Office of the People's Republic of China (SIPO) Office Action 2 for 201510628649.2 Sep. 12, 2017 10 Pages (including translation).
The State Intellectual Property Office of the People's Republic of China (SIPO) Office Action 1 for 201510733090.2 Apr. 5, 2017 7 Pages (including translation).

* cited by examiner

HEALTH MANAGEMENT METHOD, APPARATUS, AND SYSTEM

CROSS-REFERENCES TO RELATED APPLICATIONS

This application claims priority to PCT Patent Application No. PCT/CN2016/096041, filed on Aug. 19, 2016, which claims priority to Chinese Patent Application No. 201510618806.1, entitled "METHOD, APPARATUS, AND SYSTEM FOR OBTAINING HEALTH CONSULTATION SERVICE" filed on Sep. 24, 2015.

This application further claims priority to PCT Patent Application No. PCT/CN2016/097242, filed on Aug. 29, 2016, which claims priority to Chinese Patent Application No. 201510628649.2, entitled "TEST-PAPER-BASED MEASUREMENT METHOD AND APPARATUS" filed on Sep. 28, 2015.

This application further claims priority to PCT Patent Application No. PCT/CN2016/099440, filed on Sep. 20, 2016 which claims priority to Chinese Patent Application No. 201510672951.8, entitled "HEALTH INDEX MEASUREMENT METHOD AND APPARATUS" filed on Oct. 16, 2015.

This application further claims priority to PCT Patent Application No. PCT/CN2016/097537, filed on Aug. 31, 2016, which claims priority to Chinese Patent Application No. 201510733090.X, entitled "METHOD AND APPARATUS FOR DISPLAYING HEALTH DATA" filed on Nov. 2, 2015. The entire contents of all of which are incorporated herein by reference.

FIELD OF THE TECHNOLOGY

Embodiments of the present disclosure relate to the field of medical service technologies, and in particular, to a method, an apparatus, and a system for health management.

BACKGROUND OF THE DISCLOSURE

Health monitoring device (or health index measurement devices) such as blood pressure meters, blood glucose meters, and body fat monitors have entered daily life of people. People can monitor health conditions of themselves by using the health monitoring devices. For blood glucose meters, matching test strips are needed to draw blood for analysis. Calibration information of the blood glucose test strip directly affects the measurement accuracy of the blood glucose meter.

In the prior art, when a user detects abnormal physiological data by using a health monitoring device and needs to consult with a doctor, the user needs to go to hospital. In this way, the efficiency of obtaining a health consultation service is relatively low. After the measurement on the health index is completed, the user needs to manually record the health index onto a corresponding recording card, to facilitate comparison with data measured next time. The accuracy of a blood glucose value obtained by using a blood glucose meter and a blood glucose test strip by a home user is relatively low due to, for example, inaccurate calibration information. Further, after a user completes blood glucose measurement by using a blood glucose meter, a blood glucose value of the user is displayed in a numerical form at a preset display position of the blood glucose meter. No information is provided for comparing the blood glucose value with a standard reference value, so as to obtain a measurement result of a blood glucose level higher than a normal level or a blood glucose level lower than the normal level of the user.

SUMMARY

One aspect of the present disclosure provides a method for health management. The method includes: receiving, from a graphical interface of a first user terminal, login information of a first user account, the first user terminal having a memory, a processor, and a measurement sensor; obtaining, by the first user terminal, physiological data of a user based on a measurement value detected by the measurement sensor; storing the physiological data into a medical record corresponding to the first user account; and sending, by the first user terminal via a server, the physiological data to a second user terminal associated with the first user account remotely.

Another aspect of the present disclosure provides an apparatus for health management. The apparatus includes: a memory, a processor coupled to the memory, and a measurement sensor. The processor is configured for: receiving, from a graphical interface, login information of a first user account; obtaining physiological data of a user based on a measurement value detected by the measurement sensor; storing the physiological data into a medical record corresponding to the first user account; and sending, via a server, the physiological data to a second user terminal associated with the first user account remotely.

BRIEF DESCRIPTION OF THE DRAWINGS

To describe the technical solutions of the embodiments of the present disclosure more clearly, the following briefly introduces the accompanying drawings required for describing the embodiments. Apparently, the accompanying drawings in the following description show only some embodiments of the present disclosure, and a person of ordinary skill in the art may still derive other drawings from these accompanying drawings without creative efforts.

DESCRIPTION OF EMBODIMENTS

To make the objective, technical solutions, and advantages of the present disclosure clearer, the present disclosure will be further described in detail below with reference to the accompanying drawings. Obviously, the described embodiments are merely some of the embodiments of the present disclosure, rather than all the embodiments of the present disclosure. Based on the embodiments in the present disclosure, all other embodiments obtained by a person of ordinary skill in the art without creative efforts fall into the protection scope of the present disclosure.

The present disclosure provides a method, an apparatus, and a system for health management. The apparatus (or a first user terminal) includes a memory, a processor, and a measurement sensor. The system may include the apparatus and a remote server connected to the apparatus. In some embodiments, the system may further include a second user terminal connected to the remote server. The method may be implemented by the apparatus or the system. The method includes: receiving, from a graphical interface of a first user terminal, login information of a first user account, the first user terminal having a memory, a processor, and a measurement sensor; obtaining, by the first user terminal, physiological data of a user based on a measurement value detected by the measurement sensor; storing the physiological data into a medical record corresponding to the first user account; and sending, by the first user terminal via a server, the physiological data to a second user terminal associated with the first user account remotely. In some embodiments, the physiological data may be automatically sent out by the first user terminal at once when the measurement value is detected and the physiological data is obtained.

Figure 1:
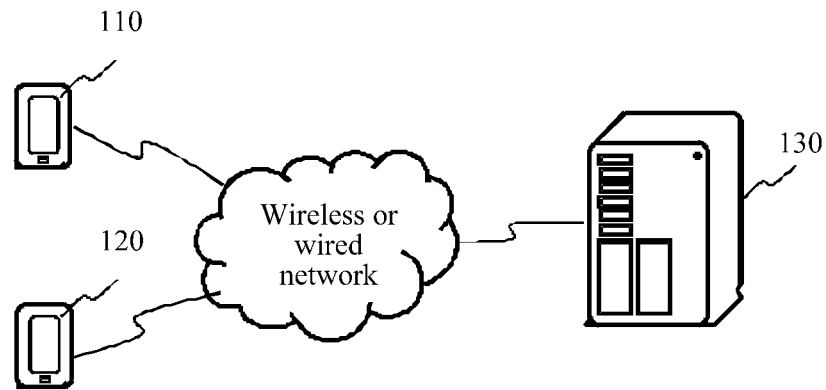
FIG. 1 is a schematic diagram of an environment in which methods, which are provided in various embodiments of the present disclosure, for obtaining a health consultation service are implemented.

Referring to FIG. 1, FIG. 1 is a schematic diagram of an environment in which methods, which are provided in various embodiments of the present disclosure, for obtaining a health consultation service are implemented. As shown in FIG. 1, the implementation environment may include a first terminal 110, a second terminal 120, and a server 130.

Figure 22:
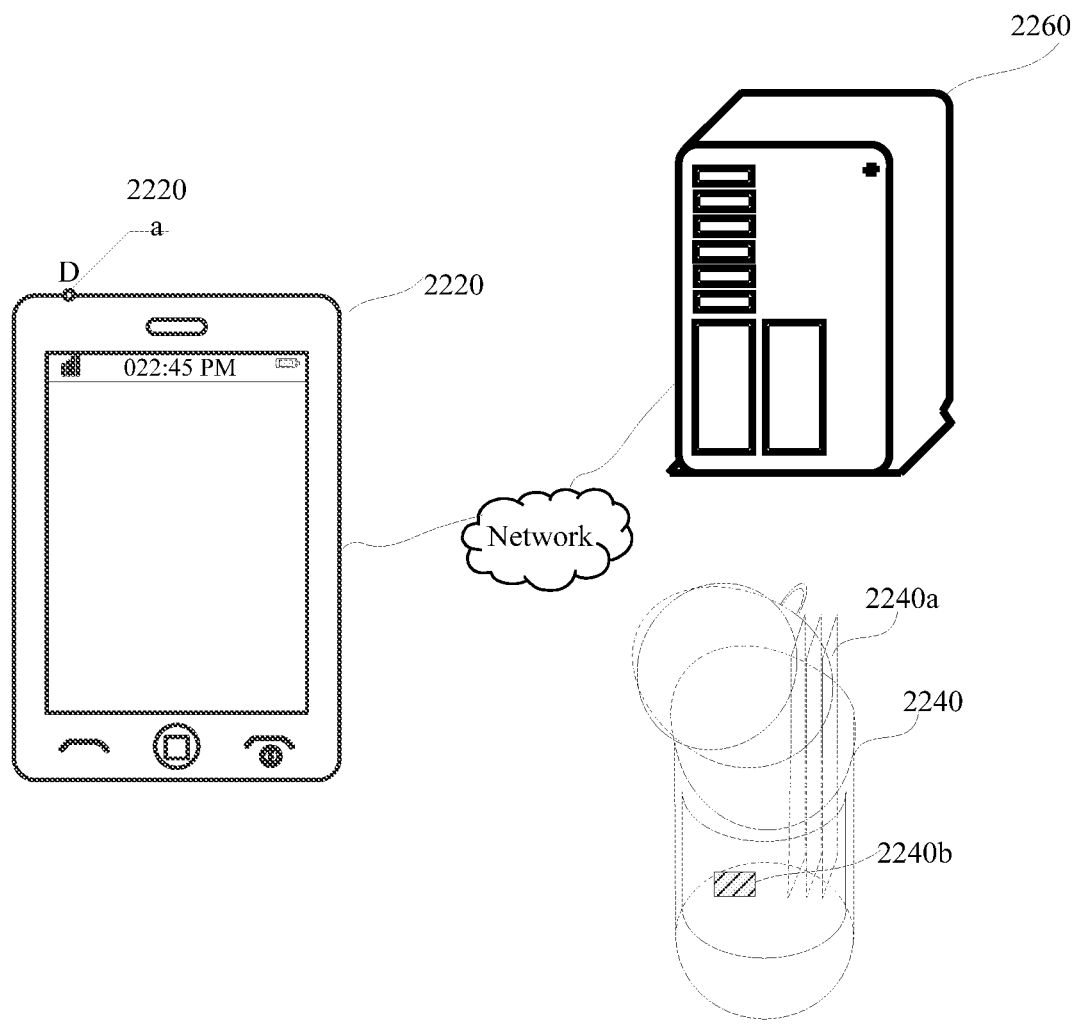
FIG. 22 is a schematic diagram of an implementation scenario involved in a test-paper-based measurement method according to an embodiment of the present disclosure.

The first terminal 110 is a terminal used by a patient, and is briefly referred to as a patient terminal (e.g., test strip analysis device 2220 shown in FIG. 22). The first terminal 110 may be a health monitoring device used by a patient (e.g., health index measurement device 1140 shown in FIG. 11, first device 2920 shown in FIG. 29), or may be a terminal (e.g., terminal 1160 shown in FIG. 11, second device 2940 shown in FIG. 29) bound with a health monitoring device, for example, a mobile phone, a tablet computer, a desktop computer, a wearable device, or a head-mounted device, or a combination thereof. The first terminal 110 may be connected to the server 130 by using a wired network or a wireless network. Schematically, the first terminal 110 is a health monitoring device such as a blood glucose meter, an electrocardiograph, a body weight scale, or a blood pressure meter, and the health monitoring device is a household health monitoring device, or a personal health monitoring device. The first terminal 110 or the health monitoring device, as used herein, may be referred as a health management apparatus. In some embodiments, the first terminal 110, the health index measurement device 1140, the test strip analysis device 2220, and first device 2920 may be integrated in one health management apparatus. Further, the graphical interfaces shown in FIGS. 5B, 5C, 13B, 14A-14E, 15B, 15E, 15H, 24B, 24C, 24D, 35A, and 35B, may all be integrated in and provided by one application program installed on the health management apparatus.

The second terminal 120 is a terminal used by a doctor, and is briefly referred to as a doctor terminal. The second terminal 120 may be a terminal such as a mobile phone, a tablet computer, or a computer. Moreover, the second terminal 120 may be connected to the server 130 by using a wired network or a wireless network. In some embodiments, the second terminal 120, the terminal 1160, and the second device 2940 may be integrated in one terminal that receives information remotely from the health management device through a server.

The server 130 may be a server, a server cluster, or a virtual calculation platform. In some embodiments, some or all of the server 130, server 1120, server 2260, and server 2960 may be integrated in one server.

Optionally, the foregoing wireless network or wired network uses a standard communications technology and/or protocol. The network is usually the Internet, or may be any network, including but not limited to a local area network (LAN), a metropolitan area network (MAN), a wide area network (WAN), or any combination of a mobile, wired, or wireless network, a dedicated network, or a virtual private network). In some embodiments, technologies and/or formats such as Hypertext Markup Language (HTML) and Extensible Markup Language (XML) are used to represent data exchanged by using the network. In addition, conventional encryption technologies such as Secure Sockets Layer (SSL), Transport Layer Security (TLS), virtual private network (VPN) and Internet Protocol Security (IPsec) are used to encrypt all or some links. In some other embodiments, customized and/or dedicated data communications technologies may alternatively be used to replace or supplement the foregoing data communications technologies.

Figure 2:
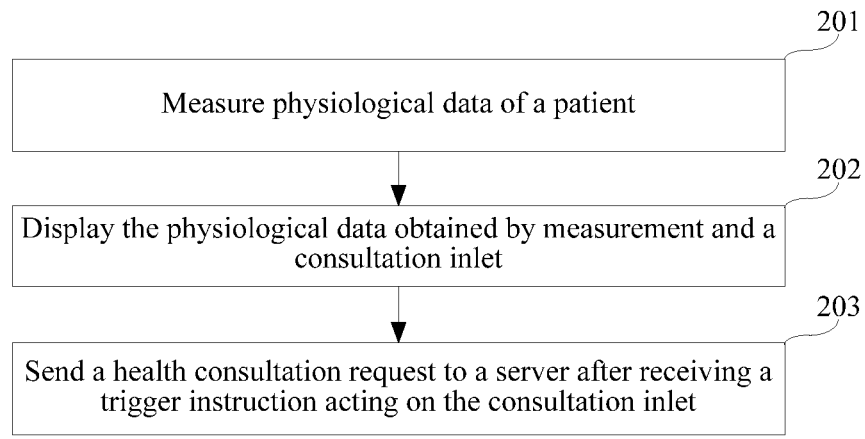
FIG. 2 is a method flowchart of a method for obtaining a health consultation service according to an embodiment of the present disclosure.

Referring to FIG. 2, FIG. 2 is a method flowchart of a method for obtaining a health consultation service according to an embodiment of the present disclosure. This embodiment is described by using an example that the method for obtaining a health consultation service is used in the first terminal 110 shown in FIG. 1. As shown in FIG. 2, the method for obtaining a health consultation service may include:

Step 201: Measure physiological data of a patient.

Optionally, physiological data is at least one type of data, such as a blood glucose value, a blood pressure value, a body weight value, an electrocardiogram, a pulse, or a heart rate. The physiological data is also referred to as a health index.

Step 202: Display the physiological data obtained by measurement and a consultation inlet.

Optionally, a health monitoring device displays the physiological data obtained by measurement in at least one of forms of text, images, audios, or videos.

Optionally, a consultation inlet is an inlet for triggering health consultation presented on the graphical user interface. A specific form of expression of the consultation inlet is at least one of a preset key control, a hyperlink control, or a menu item control.

Step 203: Send a health consultation request to a server after receiving a trigger instruction acting on the consultation inlet.

After the physiological data of a patient is obtained by measurement performed by the health monitoring device, when the patient needs professional guidance of a doctor, the patient may apply a trigger instruction on the consultation inlet on the health monitoring device. After receiving the trigger instruction, the health monitoring device sends a health consultation request to a server.

The trigger instruction may be an instruction of pressing a preset key in the health monitoring device, or may be a trigger instruction of selecting a trigger option displayed in the health monitoring device. Optionally, the trigger option is a hyperlink control or a menu item control.

Optionally, the health consultation request carries a contact method of the patient, or carries a patient identifier, and the server stores a contact method corresponding to the patient identifier.

Optionally, the health consultation request is used to request the server to forward the health consultation request to a doctor terminal, and request the doctor to provide, according to the contact method of the patient, the health consultation service to the patient.

Based on the above, according to the method for obtaining a health consultation service according to this embodiment, after a trigger instruction is received, a health consultation request is sent to a server, so that the server can forward the health consultation request to a doctor terminal that provides a consultation service to a patient; the health consultation request is used to request a doctor to provide a health consultation service to the patient according to a contact method of the patient. In this way, the problem in the prior art that a patient can obtain a health consultation service only after the patient performs registration (e.g., checks-in and waits in line) in hospital, resulting in low efficiency of obtaining the health consultation service is resolved, and the effect of improving the efficiency of obtaining, by the patient, the health consultation service can be achieved.

Figure 3:
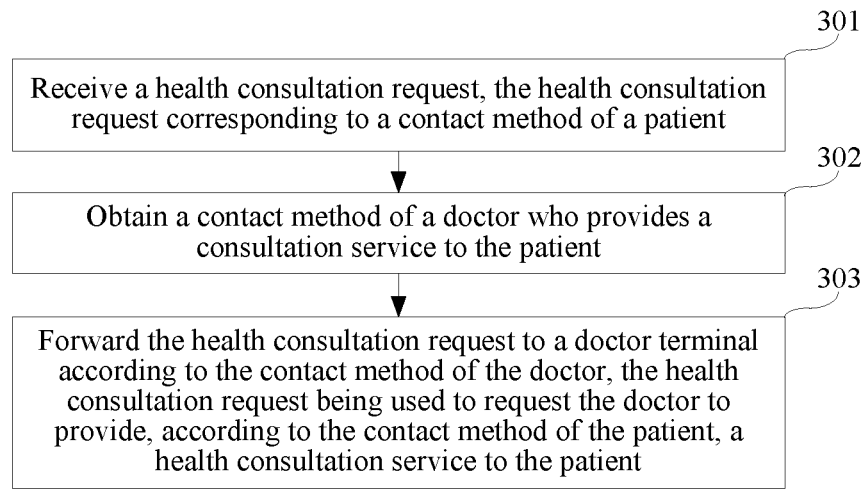
FIG. 3 is a method flowchart of a method for obtaining a health consultation service according to another embodiment of the present disclosure.

Referring to FIG. 3, FIG. 3 is a method flowchart of a method for obtaining a health consultation service according to another embodiment of the present disclosure. This embodiment is described by using an example that the method for obtaining a health consultation service is used in the server 130 shown in FIG. 1. As shown in FIG. 3, the method for obtaining a health consultation service may include:

Step 301: Receive a health consultation request, the health consultation request corresponding to a contact method of a patient.

Optionally, a health consultation request carries a contact method of a patient, or carries a patient identifier, and the server stores a contact method corresponding to the patient identifier. The contact method of the patient and/or patient identifier may be stored in a profile corresponding to the user account.

Step 302: Obtain a contact method of a doctor who provides a consultation service to the patient.

Step 303: Forward the health consultation request to a doctor terminal according to the contact method of the doctor, the health consultation request being used to request the doctor to provide, according to the contact method of the patient, a health consultation service to the patient. In some embodiments, information forwarded to the doctor terminal further includes: the measured physiological data, and/or medical record of the patient.

Based on the above, according to the method for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a health consultation service only after the patient performs registration in hospital, resulting in low efficiency of obtaining the health consultation service is resolved, and the effect of improving the efficiency of obtaining, by the patient, the health consultation service can be achieved.

Figure 4A:
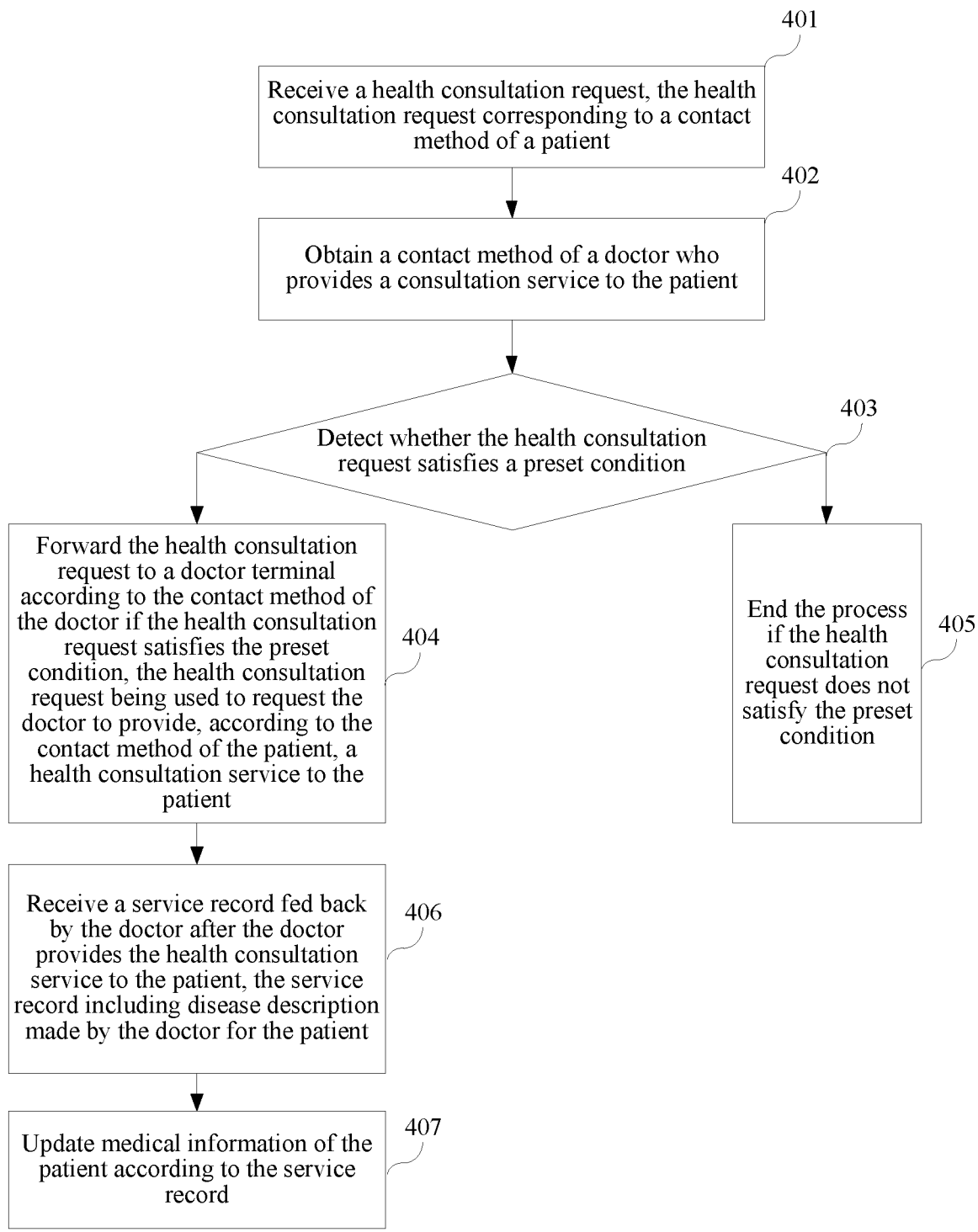
FIG. 4A is a method flowchart of a method for obtaining a health consultation service according to still another embodiment of the present disclosure.

Referring to FIG. 4A, FIG. 4A is a method flowchart of a method for obtaining a health consultation service according to still another embodiment of the present disclosure. This embodiment is described by using an example that the method for obtaining a health consultation service is used in the server 130 shown in FIG. 1. As shown in FIG. 4A, the method for obtaining a health consultation service includes:

Step 401: Receive a health consultation request, the health consultation request carrying a contact method of a patient.

When a patient needs to obtain a health consultation service, the patient may send a health consultation request to the server by using a first terminal used by the patient. Correspondingly, the server receives the health consultation request.

The first terminal may be a health monitoring device used by the patient for measuring physiological data, or may be a terminal bound with the health monitoring device, for example, a device such as a mobile phone, a tablet computer, or a desktop computer. Moreover, the first terminal may send the health consultation request to the server by using a 2-Generation wireless telephone technology (2G), 3G, 4G, or Wireless-Fidelity (WiFi) network.

Optionally, the health consultation request carries a contact method of the patient, or carries a patient identifier, and the server stores a contact method corresponding to the patient identifier. The contact method of the patient includes at least one of a telephone number, a social account of a social application client, an email address, or a home address of the patient.

Description is made by using an example that the first terminal is a blood glucose meter used by the patient as an example. When the patient detects an abnormal blood glucose value by measurement by using a blood glucose meter and wants to consult with a doctor, the patient presses a key in the blood glucose meter for calling the doctor. After receiving a press signal, the blood glucose meter sends the health consultation request to the server. Optionally, the blood glucose meter further displays a display interface including a call option. After receiving a selection signal that the patient selects the call option, the blood glucose meter sends the health consultation request to the server.

Step 402: Obtain a contact method of a doctor who provides a consultation service to the patient.

Optionally, this step includes the following two possible implementation manners.

The first possible implementation manner is that the first terminal determines a doctor corresponding to the patient according to a preset correspondence between the patient and the doctor, and obtains a contact method of the determined doctor.

Optionally, the server pre-stores the preset correspondence between the patient and the doctor. After the health consultation request is received, the doctor corresponding to the patient is queried in the preset correspondence. The patient may correspond to one doctor or may correspond to a doctor team including at least two candidate doctors.

Optionally, if there are at least two candidate doctors corresponding to the patient, the server determines a doctor for the patient according to at least one of a quantity of patients who each candidate doctor currently needs to serve or qualifications of the candidate doctors.

Schematically, the server determines the quantity of patients who each candidate doctor currently needs to serve, and determines a candidate doctor who currently needs to serve a minimum quantity of patients as the doctor corresponding to the patient.

Schematically, the server determines a qualification of each candidate doctor, and determines a candidate doctor with a highest qualification as the doctor corresponding to the patient. Optionally, the qualification is an occupation qualification or a degree qualification.

Schematically, for each candidate doctor, the server calculates a first score according to the quantity of patients who the candidate doctor currently needs to serve, calculates a second score according to a qualification of the candidate doctor, obtains a third score corresponding to the candidate doctor by adding the first score to the second score, and determines a candidate doctor with a highest third score as the doctor corresponding to the patient.

Moreover, the preset correspondence in the server may be a correspondence generated and stored by the server when the patient provisions the health consultation service.

The second possible implementation manner is to allocate a doctor among various candidate doctors to the patient, and obtain a contact method of the doctor allocated to the patient.

The step of allocating a doctor among various candidate doctors to the patient includes the following steps:

(1) Obtain pre-stored medical record information of a patient.

(2) Obtain diagnosis skills of candidate doctors.

(3) Allocate a matching doctor to the patient according to the medical record information and the diagnosis skills of the candidate doctors.

Schematically, the server extract a first keyword set from medical record information, and extracts a second keyword set from a diagnosis skill of each candidate doctor; the server calculates a similarity between the first keyword set and the second keyword set, and determines a candidate doctor corresponding to a second keyword set with a highest similarity as the doctor allocated to the patient.

The contact method of the doctor includes a telephone number, a social account of a social application client, or an email address.

It should be supplemented that after receiving the health consultation request, the server feeds back acknowledgement information to the first terminal used by the patient, and the acknowledgement information is used to indicate that doctor calling of this time succeeds.

Step 403: Detect whether the health consultation request satisfies a preset condition. The health consultation request is sent to the doctor terminal in response to that the health consultation request satisfies the preset condition.

A preset condition includes: a historical health consultation request of the patient is not received within a first time period before the health consultation request is received, and/or no doctor provides the health consultation service to the patient within a second time period before the health consultation request is received.

Schematically, for example, if the first time period is 5 minutes, after receiving the health consultation request, the server detects whether a historical health consultation request from a same patient is received within latest 5 minutes; if the historical health consultation request is not received, it is determined that the health consultation request satisfies the preset condition, and if the historical health consultation request is received, the health consultation request received this time may possibly be a request false-triggered by the patient; in this case, the server determines that the health consultation request does not satisfy the preset condition.

Schematically, for example, if the second time period is 10 minutes, after receiving the health consultation request, the server obtains a service record fed back by the doctor after the doctor provides the consultation service to the patient in historical time periods, determines, according to the obtained service record, time when the doctor provides the consultation service to the patient for the latest time, and detects whether the time belongs to 10 minutes before the health consultation request is received this time. If the time belongs to 10 minutes before the health consultation request is received this time, it indicates that the doctor provides the consultation service to the patient just now, and the health consultation request received this time may possibly be a request false-triggered by the patient, and in this case, the server determines that the health consultation request received this time does not satisfy the present condition; otherwise, if the time does not belong to 10 minutes before the health consultation request is received this time, the server determines that the health consultation request received this time satisfies the preset condition.

If the preset condition is satisfied, step 404 is entered, and if the preset condition is not satisfied, step 405 is entered.

It should be supplemented that this step is an optional step, and in actual implementation, the server may directly perform step 404. Moreover, this embodiment is described only by using an example that this step is performed after step 402. Optionally, the server may alternatively perform step 402 and step 403 simultaneously, or first perform step 403 and then perform step 402. This embodiment makes no limitation to the specific sequence of performing step 402 and step 403.

Step 404: Forward the health consultation request to a doctor terminal according to the contact method of the doctor if the health consultation request satisfies the preset condition, the health consultation request being used to request the doctor to provide, according to the contact method of the patient, a health consultation service to the patient.

Schematically, if the health consultation request carries the contact method of the patient, the server directly sends the health consultation request to a doctor terminal; if the health consultation request carries the patient identifier, the server queries the contact method corresponding to the patient identifier, carries the contact method in the health consultation request, and sends same to the doctor terminal.

Correspondingly, the doctor terminal receives the health consultation request forwarded by the server. Moreover, after obtaining the health consultation request, the doctor needs to provide the health consultation service to the patient according to the contact method of the patient. For example, description is made by using that the contact method of the patient includes a telephone number. The doctor dials the telephone number, and then provides the consultation service to the patient.

Step 405: End the process if the health consultation request does not satisfy the preset condition.

Step 406: Receive a service record fed back by the doctor terminal after the health consultation service is provided to the patient, the service record including disease description made by the doctor for the patient.

After providing the consultation service to the patient, the doctor feeds back the service record by using the doctor terminal. Specifically, the doctor may edit the service record in the doctor terminal, and then feeds back the service record to the server by using a second terminal. The service record includes disease description made by the doctor for the patient, and may be video information, voice information, or text information.

Optionally, the service record further includes the patient identifier.

Step 407: Update medical record information of the patient according to the service record.

The server updates medical record information of the patient according to disease description in the received service record.

Figure 4B:
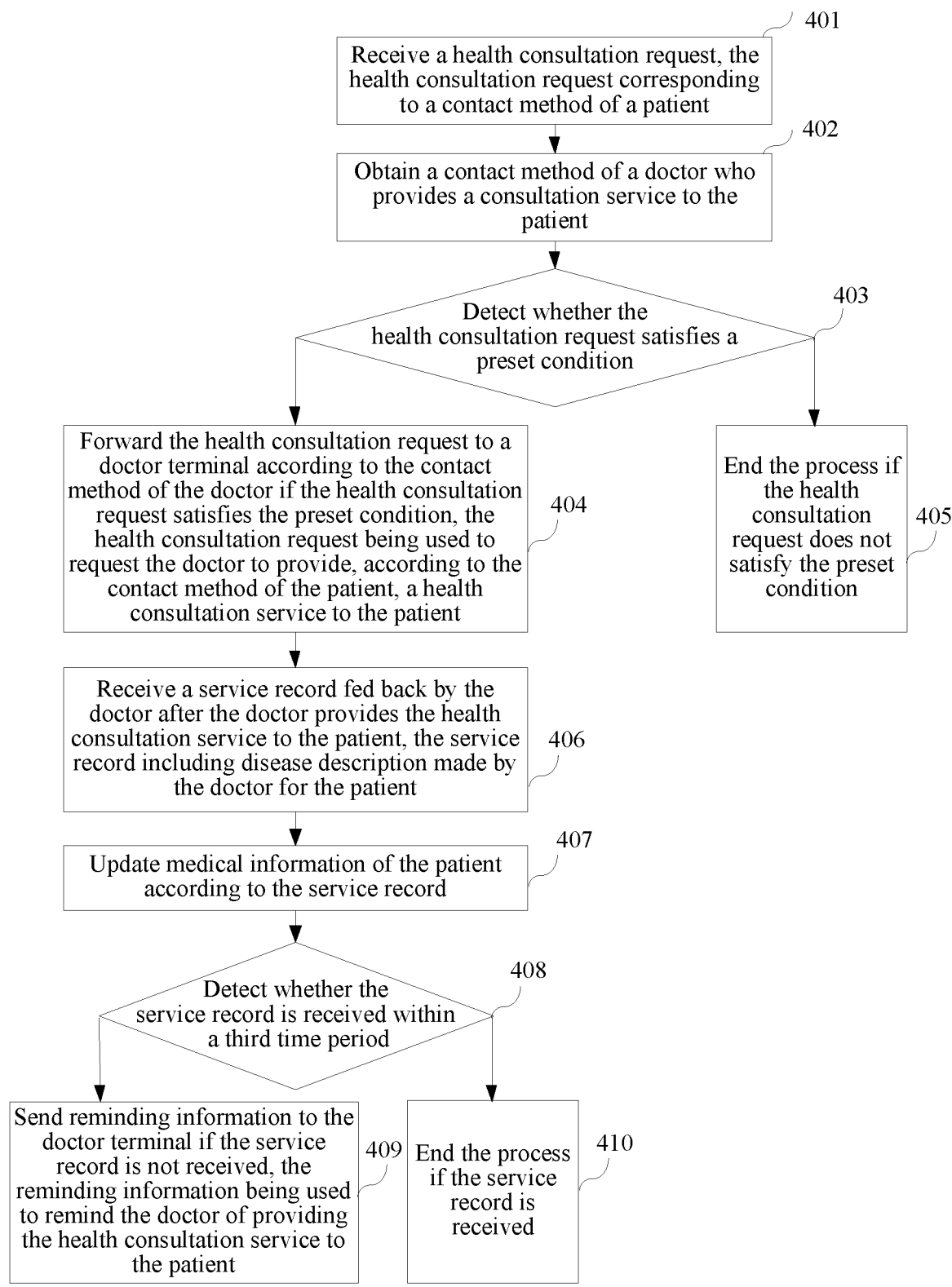
FIG. 4B is another method flowchart of the method for obtaining a health consultation service according to the still another embodiment of the present disclosure.

It should be supplemented that, referring to FIG. 4B, after step 404, the method for obtaining a health consultation request further includes the following steps:

Step 408: Detect whether the service record is received within a third time period.

After forwarding the health consultation request to the doctor terminal, the server detects whether the service record fed back by the doctor is received within a third time period.

Optionally, a starting moment of the third time period is a moment when the health consultation request is forwarded.

If the service record is not received within the third time period, step 409 is entered; if the service record is received within the third time period, step 410 is entered.

Step 409: Send reminding information to the doctor terminal if the service record is not received, the reminding information being used to remind the doctor of providing the health consultation service to the patient.

If the service record is not received, it indicates that the doctor is possibly providing the consultation service to the patient, or the doctor forgets to feed back the service record. In this case, the server sends reminding information to the doctor terminal. The reminding information is used to remind the doctor of providing the health consultation service to the patient. The reminding information is at least one of a text message, a picture message, an audio message, or a video message.

Step 410: End the process if the service record is received.

If the service record has been received, it indicates that the doctor has provided the consultation service to the patient, and in this case, the process ends.

Based on the above, according to the method for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a health consultation service only after the patient performs registration in hospital, resulting in low efficiency of obtaining the health consultation service is resolved, and the effect of improving the efficiency of obtaining, by the patient, the health consultation service can be achieved.

Before the health consultation request is forwarded to the doctor terminal, whether the health consultation request satisfies a preset condition is first detected, and the health consultation request is forwarded to the doctor terminal only when a result of the detection is that the health consultation request satisfies the preset condition. In this way, the problem that the doctor repeatedly provides the health consultation service to the patient after the patient frequently calls the doctor, resulting in resource waste and confusion brought to the patient is avoided.

After the health consultation request is forwarded to the doctor terminal, whether a service record fed back by the doctor is received within a third time period is detected, and reminding information is sent to the doctor terminal when the service record is not received, to remind the doctor of providing the health consultation service to the patient as soon as possible, thereby improving the efficiency of obtaining, by the patient, the health consultation service.

Figure 5A:
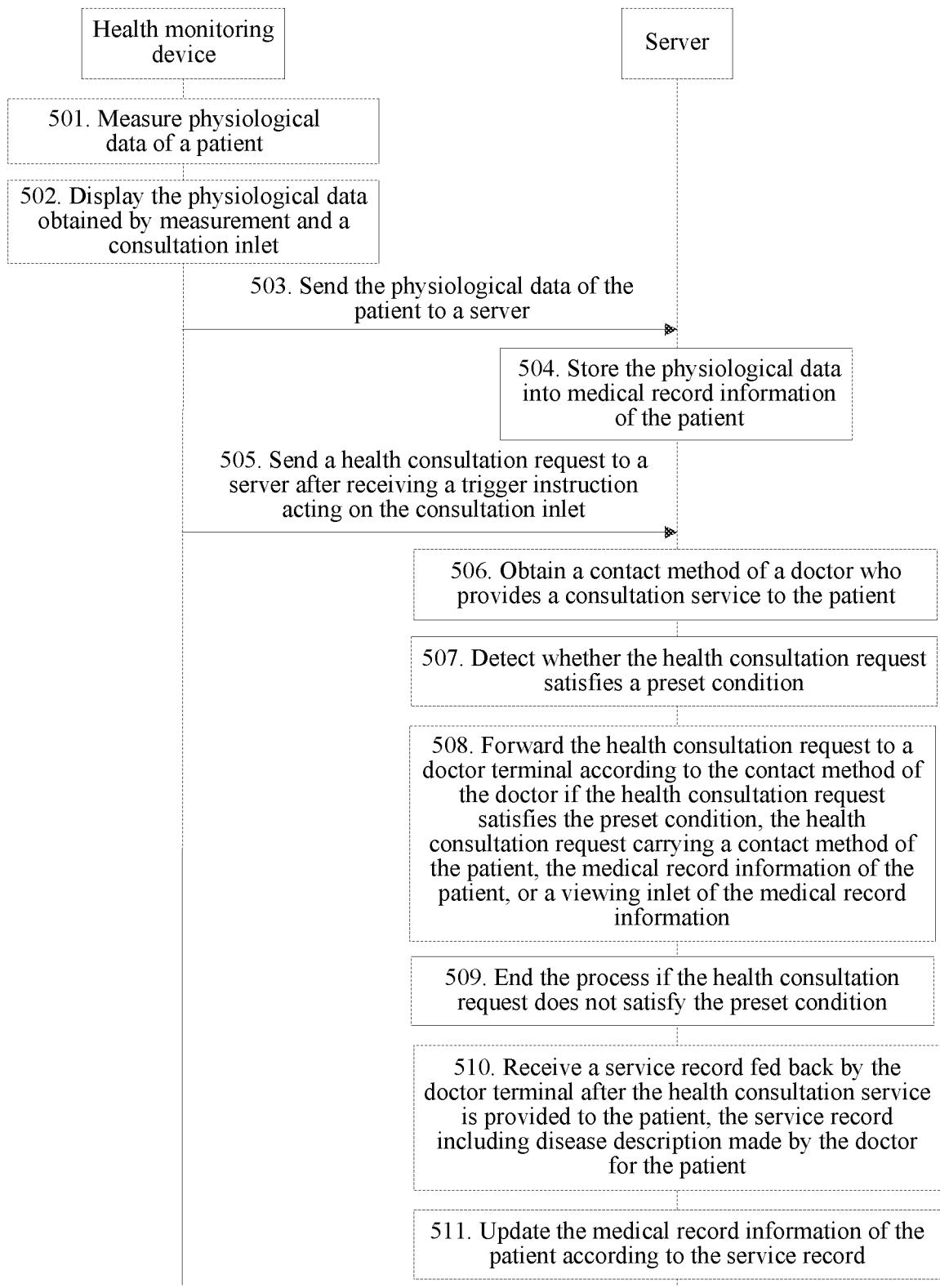
FIG. 5A is a method flowchart of a method for obtaining a health consultation service according to yet another embodiment of the present disclosure.

Referring to FIG. 5A, FIG. 5A is a flowchart of a method for obtaining a health consultation service according to an embodiment of the present disclosure. This embodiment is described by using an example that the method for obtaining a health consultation service is used in the implementation environment shown in FIG. 1. As shown in FIG. 5A, the method includes the following.

Step 501: A health monitoring device measures physiological data of a patient.

Optionally, a health monitoring device measures physiological data of a patient by using measurement components such as a test strip, an electrode, and a sensor. The health monitoring device may include blood glucose meter, coupled with lancing device and lancets for drawing blood to be collected by the test strip.

Optionally, physiological data is at least one type of data, such as a blood glucose value, a blood pressure value, a body weight value, an electrocardiogram, a pulse, or a heart rate.

Step 502: The health monitoring device displays the physiological data obtained by measurement and a consultation inlet.

Optionally, the health monitoring device displays the physiological data obtained by measurement in at least one of forms of text, images, audios, or videos.

Optionally, a consultation inlet is an inlet for triggering health consultation.

Figure 5B:
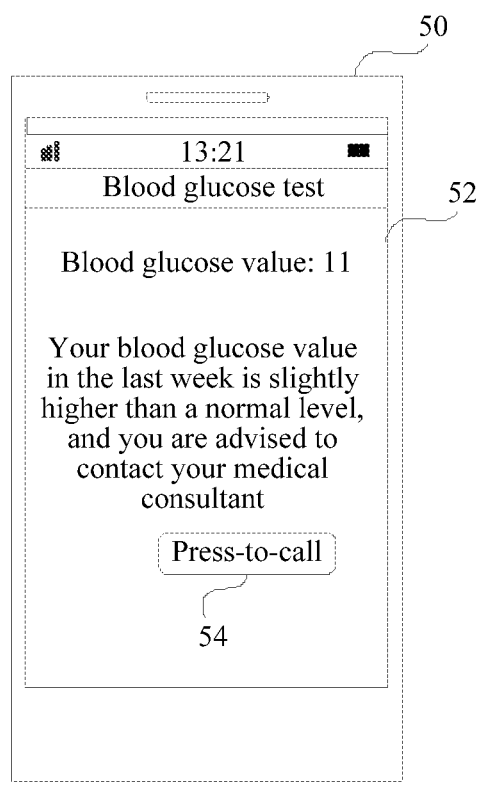
FIG. 5B is a schematic diagram of an interface during specific implementation of the method for obtaining a health consultation service according to the embodiment of FIG. 5A.

Schematically, referring to FIG. 5B, a blood glucose meter 50 obtains a blood glucose value of the patient by measurement by using a blood glucose test strip, and displays the blood glucose value of the patient and a consultation inlet 54 on a user interface 52. Prompt information "your blood glucose value in the latest week is slightly higher than a normal level, and you are advised to contact your medical consultant" is displayed on the user interface 52. The consultation inlet 54 is a key control, and "press-to-call" is displayed on the button control.

Step 503: The health monitoring device sends the physiological data of the patient to a server.

The health monitoring device sends the physiological data of the patient to a server. Optionally, the physiological data includes: a patient identifier, physiological data collected this time, and collection time this time.

Correspondingly, the server receives the physiological data sent by the health monitoring device.

Step 504: The server stores the physiological data into medical record information of the patient.

Optionally, the server stores the physiological data into medical record information corresponding to the patient identifier. Optionally, the medical record information includes: the patient identifier, basic information about the patient, physiological data of the patient, and a historical service record of the patient. The following Table 1 schematically shows the medical record information.

TABLE 1

| Patient identifier | 0001 | 0002 |
|---|---|---|
| Name | User A | User B |
| Age | 45 | 67 |
| Gender | Male | Female |
| Contact method | 138-0000-xxxx | 131-8888-xxxx |
| Blood glucose value for a first time | 7.6 (collection time A1) | 6.1 (collection time B1) |
| Blood glucose value for a second time | 11 (collection time A2) | 5 (collection time B2) |
| Blood glucose value for a third time | 10.2 (collection time A3) | 6 (collection time B3) |
| ... | ... | ... |
| Service record for the first time | Lack of control on diet causes blood glucose to be slightly higher than a normal value for multiple times. Do eat less each time and eat for more times (service time A4) | Blood glucose is normal, and there is no obvious abnormality (service time B4) |
| Service record for the second time | Blood glucose is relatively stable, and control on diet is relatively good (service time A5) | Null |

Step 505: The health monitoring device sends a health consultation request to a server after receiving a trigger instruction acting on the consultation inlet.

Optionally, a health consultation request carries a contact method of the patient, or carries the patient identifier, and the server stores a contact method corresponding to the patient identifier.

It should be noted that this embodiment makes no limitation to the sequence for performing step 503 and step 504. In other embodiments, step 503 and step 505 are simultaneously performed, or step 503 is performed after step 505.

Correspondingly, the server receives the health consultation request.

Step 506: The server obtains a contact method of a doctor who provides a consultation service to the patient.

After receiving the health consultation request, the server obtains a contact method of a doctor who provides the consultation service to the patient.

The contact method of the doctor includes a telephone number, a social account of a social application client, or an email address.

Step 507: The server detects whether the health consultation request satisfies a preset condition.

A preset condition includes: a historical health consultation request of the patient is not received within a first time period before the health consultation request is received, and/or no doctor provides the health consultation service to the patient within a second time period before the health consultation request is received.

If the preset condition is satisfied, step 508 is entered, and if the preset condition is not satisfied, step 509 is entered.

It should be supplemented that this step is an optional step, and in actual implementation, the server may directly perform step 508. Moreover, this embodiment is described only by using an example that this step is performed after step 506. Optionally, the server may alternatively perform step 506 and step 507 simultaneously, or first perform step 507 and then perform step 506. This embodiment makes no limitation to the specific sequence of performing step 506 and step 507.

Step 508: Forward the health consultation request to a doctor terminal according to the contact method of the doctor if the health consultation request satisfies the preset condition, the health consultation request carrying a contact method of the patient, the medical record information of the patient, or a viewing inlet of the medical record information.

Schematically, if the health consultation request carries the contact method of the patient, the server adds the medical record information of the patient or a viewing inlet of the medical record information into the health consultation request, and sends the health consultation request to a doctor terminal.

Schematically, if the health consultation request carries the patient identifier, the server queries the contact method and medical record information corresponding to the patient identifier, adds the contact method of the patient, the medical record information of the patient, or the viewing inlet of the medical record information into the health consultation request, and sends the health consultation request to the doctor terminal.

Figure 5C:
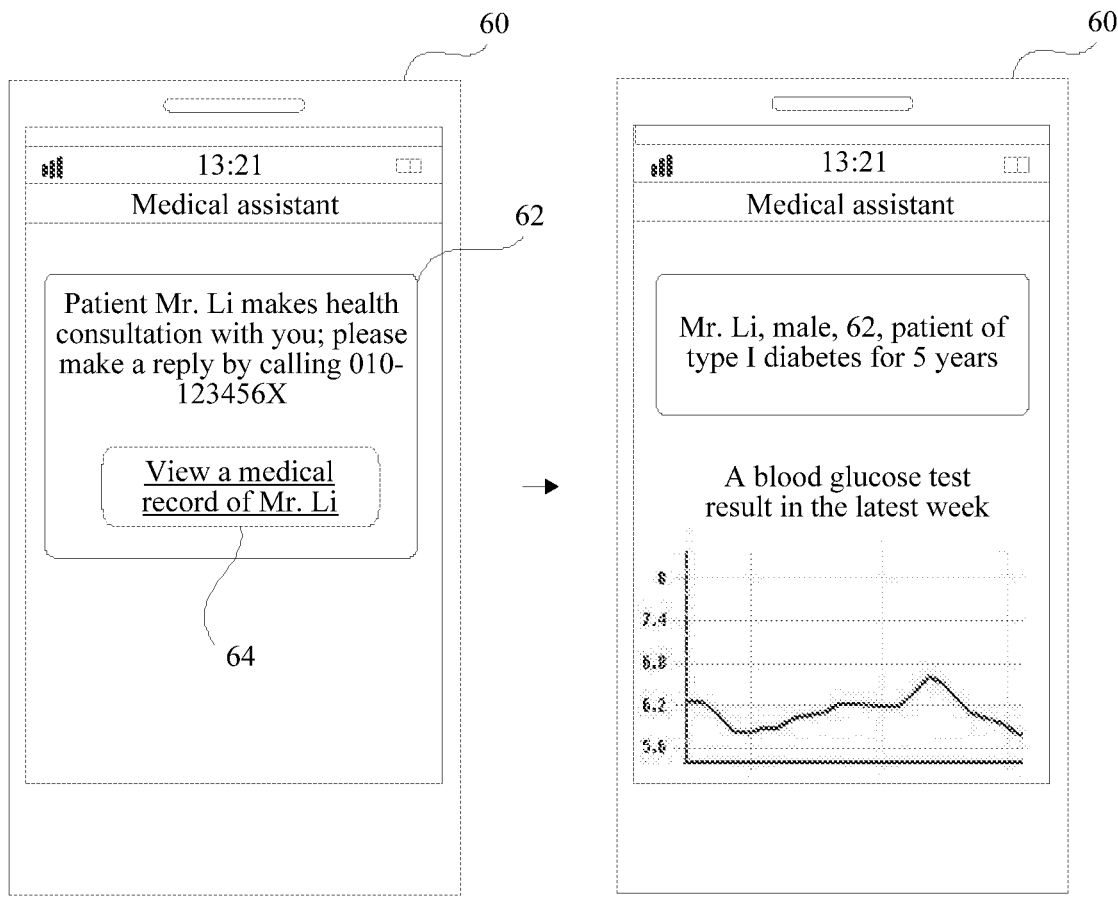
FIG. 5C is a schematic diagram of an interface during specific implementation of the method for obtaining a health consultation service according to the embodiment of FIG. 5A.

Referring to FIG. 5C, the doctor terminal 60 receives the health consultation request, and displays the health consultation request by using a pop-up box 62. The pop-up box 62 includes: prompt information "patient 0001 makes health consultation with you; please make a reply as soon as possible" and a hyperlink 64 "view a medical record of the patient". After the hyperlink 64 "view a medical record of the patient" is selected, the doctor terminal 60 jumps to display the medical record information of the patient.

Correspondingly, the doctor terminal receives the health consultation request forwarded by the server. Moreover, after obtaining the health consultation request, the doctor needs to provide the health consultation service to the patient according to the contact method of the patient. For example, description is made by using that the contact method of the patient includes a telephone number. The doctor dials the telephone number, and then provides the consultation service to the patient.

Step 509: End the process if the health consultation request does not satisfy the preset condition.

Step 510: The server receives a service record fed back by the doctor terminal after the health consultation service is provided to the patient, the service record including disease description made by the doctor for the patient.

After providing the consultation service to the patient, the doctor feeds back a service record by using the doctor terminal. Specifically, the doctor may edit the service record in the doctor terminal, and then feeds back the service record to the server by using a second terminal. The service record includes disease description made by the doctor for the patient, and may be video information, voice information, or text information.

Optionally, the service record further includes the patient identifier.

Step 511: The server updates the medical record information of the patient according to the service record.

The server updates the medical record information of the patient according to the disease description in the received service record.

Based on the above, according to the method for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a consultation service only after the patient performs registration in hospital, resulting in low efficiency of obtaining the service is resolved, and the effect of improving the efficiency of obtaining, by the patient, the consultation service can be achieved.

Compared with the embodiment of FIG. 4A, in this embodiment, physiological data collected by a health monitoring device is further automatically uploaded to a server, and the server stores the physiological data into medical record information of the patient, so that the doctor can conveniently view the medical record information recorded by the patient when receiving the health consultation request, thereby improving the efficiency of diagnosis.

By using an example that the health monitoring device is a blood glucose meter, a diabetic patient measures a blood glucose value of himself each day after purchasing the blood glucose meter. The blood glucose meter records the blood glucose value measured each day by the patient, and synchronizes the blood glucose value into the server, and the server stores the blood glucose value into the medical record information of the patient. If the patient finds that the blood glucose value on one day is slightly higher than a normal value and hopes to obtain the health consultation service from the doctor, the patient directly presses a key of the blood glucose meter to call the doctor. The server allocates a doctor to the patient, and the doctor provides the health consultation service to the patient in a form of a telephone service, an instant messaging service, or a truck roll. When providing the health consultation service, the doctor can conveniently view the medical record information of the patient. The medical record information not only includes various physiological data obtained by measurement performed by the patient himself, but also includes service records fed back by other doctors in a historical service process.

Obviously, from the perspective of the patient, only one blood glucose meter needs to be purchased to implement multiple functions of automatically establishing medical record information, automatically generating the medical record information, pressing to call the doctor, and providing the medical record information to the doctor without manually collating the medical record information and registration in hospital by the patient. From the perspective of the doctor, the health consultation service can be provided to the patient in time, and the medical record information of the patient can be conveniently viewed, and the medical record information is comprehensive, detailed and in-time medical record information.

In another possible embodiment, the health monitoring device is a portable electrocardiograph. When a patient has a heart attack, the patient directly calls a doctor by using the portable electrocardiograph, and sends electrocardiogram data that is measured most recently to the doctor for diagnosis, and the entire process may need only one minute. However, if the patient performs registration, measures an electrocardiogram, and waits in a queue for diagnosis of a doctor in hospital, the entire process needs several hours or more than ten hours, and consequently, the optimal diagnosis time for heat attacks is missed. Based on the above, in the daily use process of the health monitoring device of the patient, the health monitoring device automatically constructs medical record information of a patient, and provides a health consultation service, so that a convenient, effective, and in-time health consultation service can be provided to the patient. Therefore, the function of the health monitoring device is not limited to a device, and instead, the health monitoring device becomes a personal health consultant of the patient, and can better ensure health of the patient.

Figure 6:
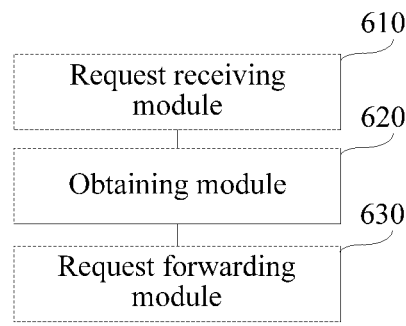
FIG. 6 is a structural block diagram of an apparatus for obtaining a health consultation service according to an embodiment of the present disclosure.

Referring to FIG. 6, FIG. 6 is a structural block diagram of an apparatus for obtaining a health consultation service according to an embodiment of the present disclosure. The apparatus for obtaining a health consultation service may include: a request receiving module 610, an obtaining module 620, and a request forwarding module 630.

The request receiving module 610 is configured to receive a health consultation request, the health consultation request carrying a contact method of a patient.

The obtaining module 620 is configured to obtain a contact method of a doctor who provides a consultation service to the patient.

The request forwarding module 630 is configured to forward the health consultation request to a doctor terminal according to the contact method, obtained by the obtaining module 620, of the doctor, the health consultation request being used to request the doctor to provide, according to the contact method of the patient, the health consultation service to the patient.

Based on the above, according to the apparatus for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a health consultation service only after the patient performs registration in hospital, resulting in low efficiency of obtaining the health consultation service is resolved, and the effect of improving the efficiency of obtaining, by the patient, the health consultation service can be achieved.

Figure 7:
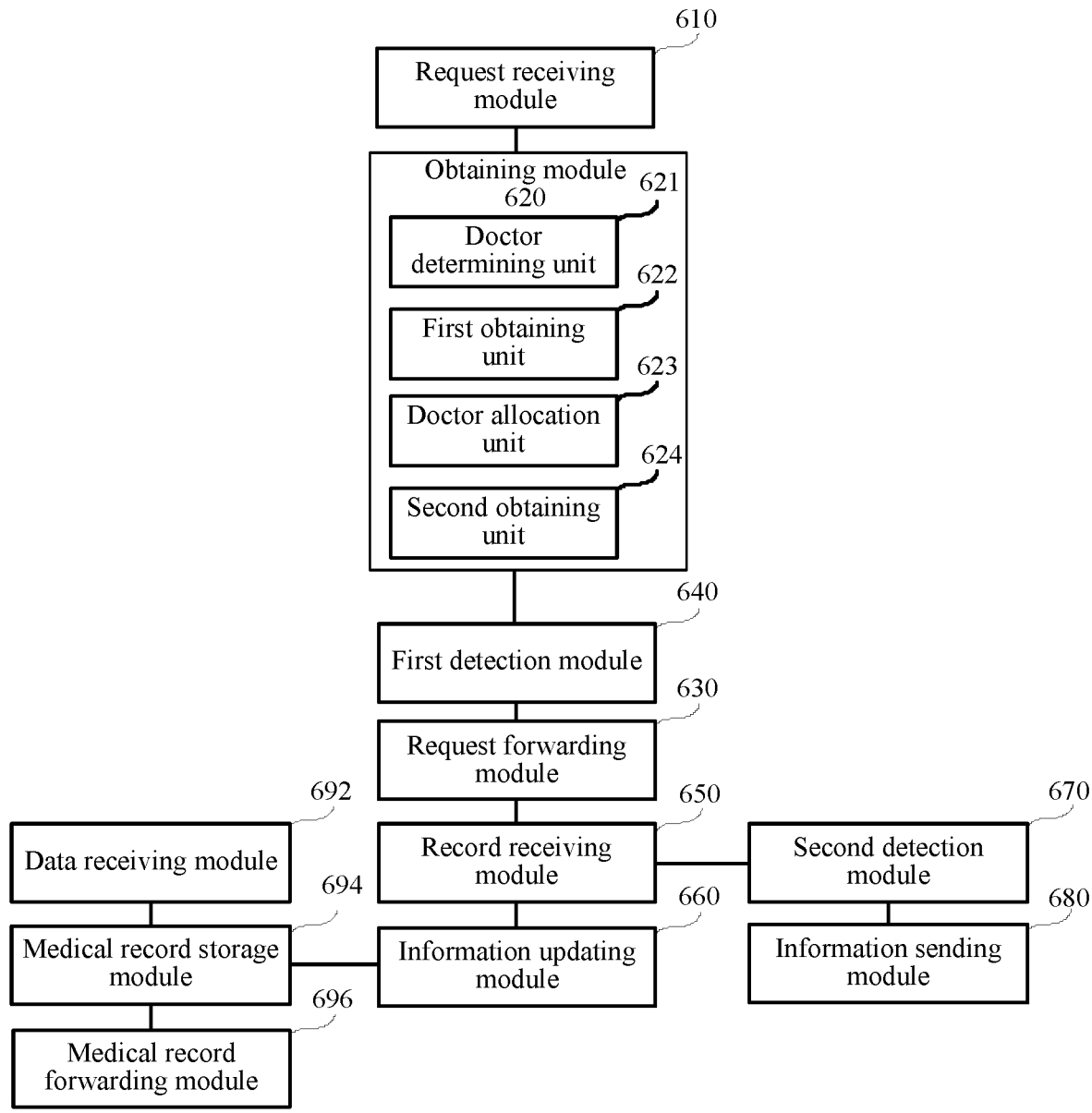
FIG. 7 is a structural block diagram of an apparatus for obtaining a health consultation service according to another embodiment of the present disclosure.

Referring to FIG. 7, FIG. 7 is a structural block diagram of an apparatus for obtaining a health consultation service according to another embodiment of the present disclosure. The apparatus for obtaining a health consultation service may include: a request receiving module 610, an obtaining module 620, and a request forwarding module 630.

The request receiving module 610 is configured to receive a health consultation request, the health consultation request carrying a contact method of a patient.

The obtaining module 620 is configured to obtain a contact method of a doctor who provides a consultation service to the patient.

The request forwarding module 630 is configured to forward the health consultation request to a doctor terminal according to the contact method, obtained by the obtaining module 620, of the doctor, the health consultation request being used to request the doctor to provide, according to the contact method of the patient, the health consultation service to the patient.

Optionally, the apparatus further includes: a data receiving module 692, a medical record storage module 694, and a medical record forwarding module 696; the data receiving module 692 is configured to receive physiological data, sent by a health monitoring device, of the patient; the medical record storage module 694 is configured to store the physiological data into medical record information of the patient; and the medical record forwarding module 696 is configured to send the medical record information of the patient or a viewing inlet of the medical record information to the doctor terminal according to the contact method of the doctor when the health consultation request is forwarded.

Optionally, the apparatus further includes: a first detection module 640, configured to detect whether the health consultation request satisfies a preset condition before the request forwarding module 630 forwards the health consultation request to the doctor terminal according to the contact method of the doctor, the preset condition including: a historical health consultation request of the patient is not received within a first time period before the health consultation request is received, and/or no doctor provides the health consultation service to the patient (e.g., no doctor terminal responds to the health consultation request) within a second time period before the health consultation request is received; and the request forwarding module 630 is further configured to perform the operation of forwarding the health consultation request to a doctor terminal according to the contact method of the doctor if a detection result of the first detection module 640 is that the health consultation request satisfies the preset condition.

Optionally, the obtaining module 620 includes: a doctor determining unit 621, configured to determine a doctor corresponding to the patient according to a preset correspondence between the patient and the doctor; and a first obtaining unit 622, configured to obtain a contact method of the doctor determined by the determining unit 621; or, a doctor allocation unit 623, configured to allocate a doctor among various candidate doctors to the patient; and a second obtaining unit 624, configured to obtain a contact method of the doctor allocated by the doctor allocation unit 623.

Optionally, the second obtaining unit 624 is further configured to: obtain pre-stored medical record information of the patient; obtain diagnosis skills of the candidate doctors; and allocate a doctor to the patient according to the medical record information and the diagnosis skills of the candidate doctors.

Optionally, the apparatus further includes: a record receiving module 650, configured to receive a service record fed back by the doctor after the doctor provides the health consultation service to the patient, the service record including disease description made by the doctor for the patient; and an information updating module 660, configured to update medical record information of the patient according to the service record received by the record receiving module 650.

Optionally, the apparatus further includes: a second detection module 670, configured to detect whether the service record is received within a third time period after the request forwarding module 630 forwards the health consultation request to the doctor terminal according to the contact method of the doctor; and an information sending module 680, configured to send reminding information to the doctor terminal if a detection result of the second detection module 670 is that the service record is not received, the reminding information being used to remind the doctor of providing the health consultation service to the patient.

Based on the above, according to the apparatus for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a consultation service only after the patient performs registration in hospital, resulting in low efficiency of obtaining the service is resolved, and the effect of improving the efficiency of obtaining, by the patient, the health consultation service can be achieved.

Before the health consultation request is forwarded to the doctor terminal, whether the health consultation request satisfies a preset condition is first detected, and the health consultation request is forwarded to the doctor terminal only when a result of the detection is that the health consultation request satisfies the preset condition. In this way, the problem that the doctor repeatedly provides the health consultation service to the patient after the patient frequently calls the doctor, resulting in resource waste and confusion brought to the patient is avoided.

After the health consultation request is forwarded to the doctor terminal, whether a service record fed back by the doctor is received within a third time period is detected, and reminding information is sent to the doctor terminal when the service record is not received, to remind the doctor of providing the health consultation service to the patient as soon as possible, thereby improving the efficiency of obtaining, by the patient, the health consultation service.

In this embodiment, physiological data collected by a health monitoring device is further automatically uploaded to a server, and the server stores the physiological data into medical record information of the patient, so that the doctor can conveniently view the medical record information recorded by the patient when receiving the health consultation request, thereby improving the efficiency of diagnosis.

Figure 8:
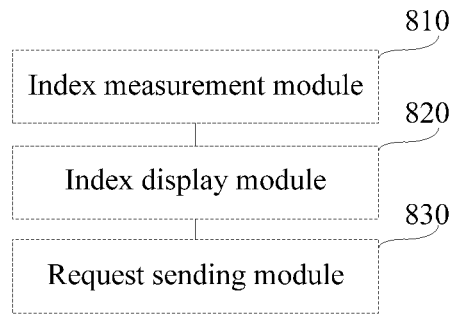
FIG. 8 is a structural block diagram of an apparatus for obtaining a health consultation service according to another embodiment of the present disclosure.

Referring to FIG. 8, FIG. 8 is a structural block diagram of an apparatus for obtaining a health consultation service according to an embodiment of the present disclosure. The apparatus for obtaining a health consultation service may include an index measurement module 810, an index display module 820, and a request sending module 830.

The index measurement module 810 is configured to measure physiological data of a patient.

The index display module 820 is configured to display the physiological data obtained by measurement performed by the index measurement module 810 and a consultation inlet.

The request sending module 830 is configured to send a health consultation request to a server after receiving a trigger instruction acting on the consultation inlet, the health consultation request carrying a contact method of the patient, and being used to request the server to forward the health consultation request to a doctor terminal that provides a consultation service to the patient, and request the doctor to provide, according to the contact method of the patient, the health consultation service to the patient.

Optionally, the apparatus further includes a data sending module (not shown in the figure). The data sending module is configured to send the physiological data of the patient to the server.

Based on the above, according to the apparatus for obtaining a health consultation service according to this embodiment, after a trigger instruction is received, a health consultation request is sent to a server, so that the server can forward the health consultation request to a doctor terminal that provides a consultation service to a patient; the health consultation request is used to request a doctor to provide a health consultation service to the patient according to a contact method of the patient. In this way, the problem in the prior art that a patient can obtain a consultation service only after the patient performs registration in hospital, resulting in low efficiency of obtaining the service is resolved, and the effect of improving the efficiency of obtaining, by the patient, the health consultation service can be achieved.

It should be noted that the above functional modules are only described for exemplary purposes when the apparatuses for obtaining a health consultation service provided by the foregoing embodiments obtain the health consultation service. In actual applications, the functions may be allocated to different functional modules according to specific needs, which means that the internal structure of the apparatus is divided to different functional modules to complete all or some of the above described functions. In addition, the apparatuses for obtaining a health consultation service provided by the foregoing embodiments are based on the same concept as the methods for obtaining a health consultation service in the foregoing embodiments. For the specific implementation process, refer to the method embodiments, and the details are not described herein again.

Figure 9:
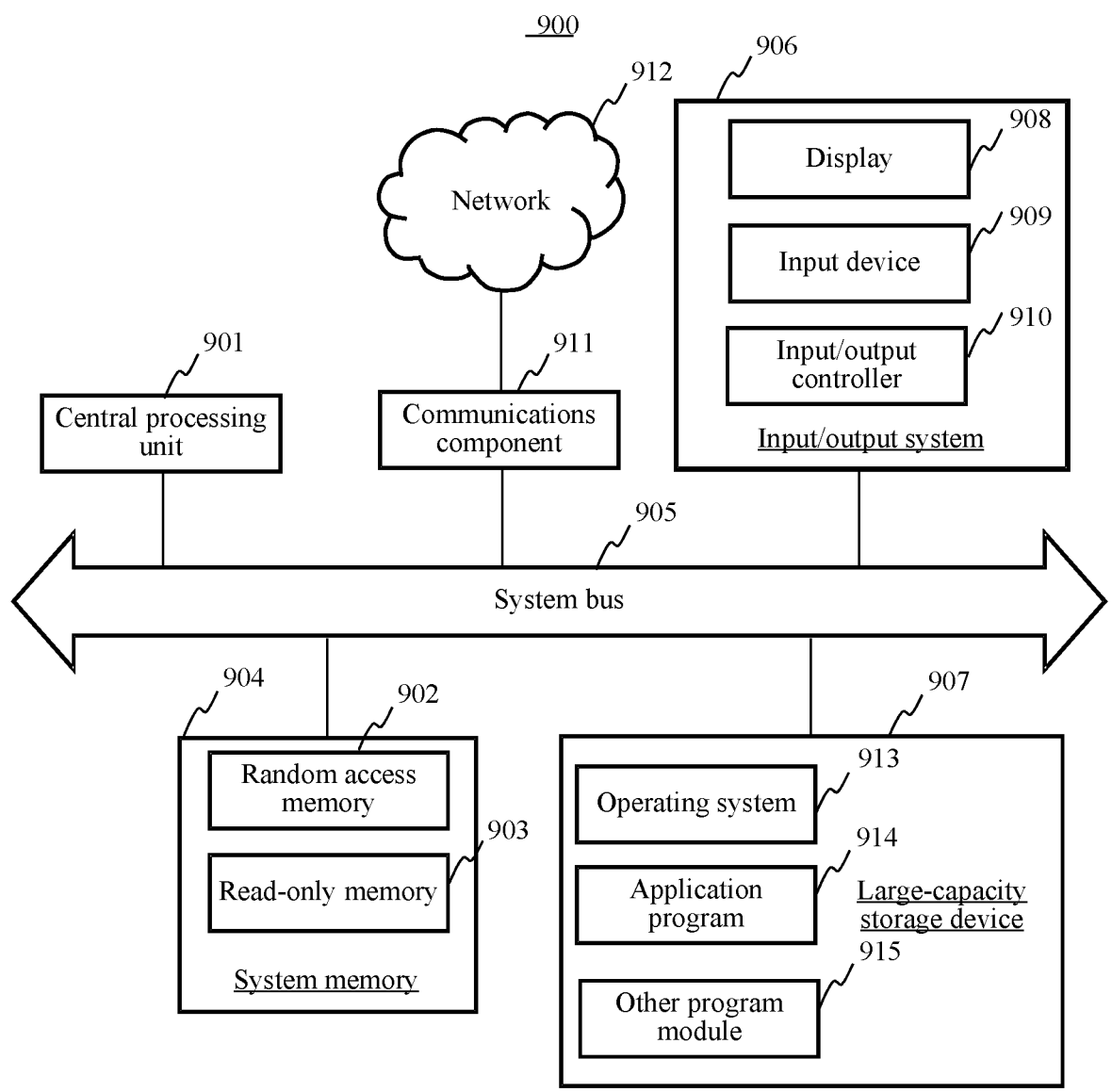
FIG. 9 is a structural block diagram of a server according to another embodiment of the present disclosure.

Referring to FIG. 9, FIG. 9 is a structural block diagram of a server according to an embodiment of the present disclosure. The server 900 includes a central processing unit (CPU) 901, a system memory 904 including a random access memory (RAM) 902 and a read-only memory (ROM) 903, and a system bus 905 connected to the system memory 904 and the CPU 901. The server 900 further includes a basic input/output system (I/O system) 906 helping information transmission between various devices in a computer, and a large-capacity storage device 907 configured to store an operating system 913, an application program 914, and other program modules 915.

The basic I/O system 906 includes a display 908 configured to display information and an input device 909 configured to enter information by a user, for example, a mouse or a keyboard. The display 908 and the input device 909 are both connected to the CPU 901 by using an input/output controller 910 connected to the system bus 905. The basic I/O system 906 may further include the input/output controller 910 for receiving and processing inputs from multiple other devices such as a keyboard, a mouse, or an electronic stylus. Similarly, the input/output controller 910 further provides an output to a display screen, a printer, or an output device of another type.

The large-capacity storage device 907 is connected to the CPU 901 by using a large-capacity storage controller (not shown) connected to the system bus 905. The large-capacity storage device 907 and computer readable media associated with the large-capacity storage device 907 provide non-volatile storage for the server 900. That is, the large-capacity storage device 907 may include computer readable media (not shown) such as a hard disk or a CD-ROM drive.

Without loss of generality, the computer readable media may include computer storage media and communications media. The computer storage media include volatile and non-volatile, movable and non-movable media implemented by any method for technology for storing information, for example, a computer readable instruction, a data structure, a program module, or other data. The computer storage media include an RAM, an ROM, an EPROM, an EEPROM, a flash memory, or other solid-state memory technologies, a CD-ROM, a DVD, or other optical storage, a cassette, a magnetic tape, a disk storage or other magnetic storage devices. Certainly, a person skilled in the art can learn that the computer storage media are not limited to the foregoing types. The foregoing system memory 904 and the large-capacity storage device 907 may be generally referred to as memories.

According to the various embodiments of the present disclosure, the server 900 may alternatively be connected to a remote computer on a network by using a network such as the Internet, for operation. That is, the server 900 may be connected to a network 912 by using a communications component 911 connected to the system bus 905, or in other words, the server 900 may be connected to a network of another type or a remote computer system (not shown) by using the communications component 911.

The memory further includes one or more programs, which are stored in the memory; the one or more programs contain instructions, which are executed by the server and are used for implementing the methods for obtaining a health consultation service according to the embodiments of the present disclosure.

A person of ordinary skill in the art may understand that all or some of the steps in the methods for obtaining a health consultation service in the foregoing embodiments may be performed by a program instructing relevant hardware. The program may be stored in a computer readable storage medium. The storage medium may be an ROM, an RAM, a magnetic disk, an optical disc, or the like.

Figure 10:
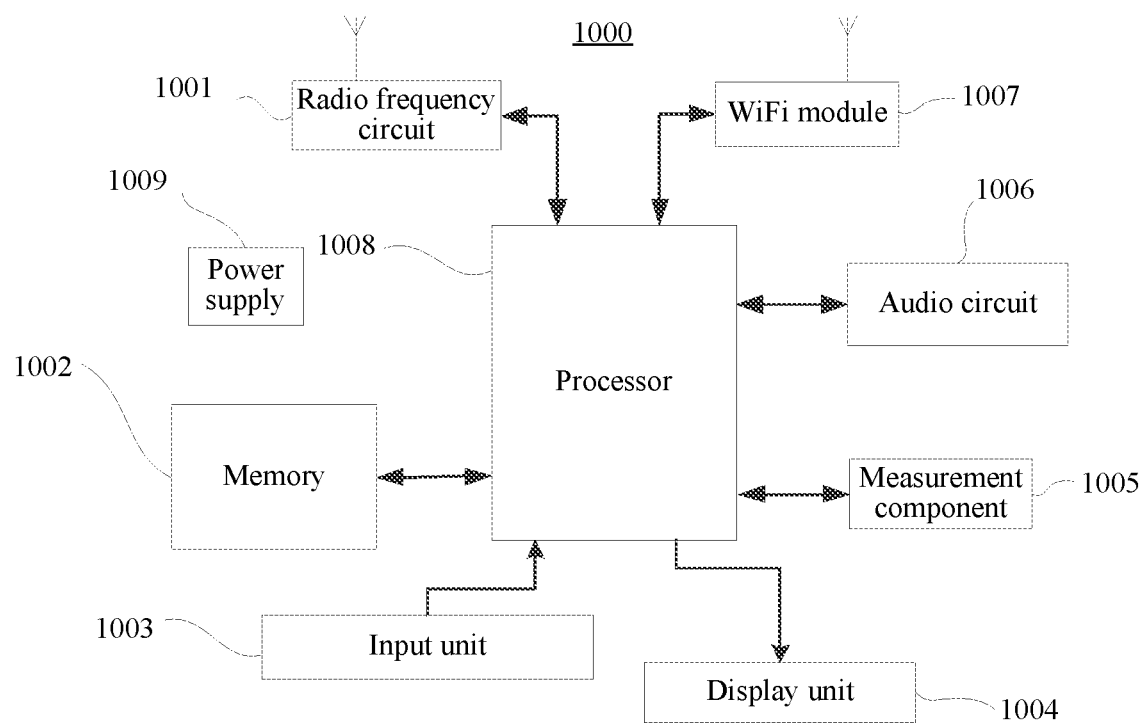
FIG. 10 is a structural block diagram of a health monitoring device according to another embodiment of the present disclosure.

Referring to FIG. 10, FIG. 10 is a block diagram of a health monitoring device 1000 according to an embodiment of the present disclosure. The health monitoring device may include components such as a radio frequency (RF) circuit 1001, a memory 1002 including one or more computer readable storage media, an input unit 1003, a display unit 1004, a measurement component 1005, an audio circuit 1006, a WiFi module 1007, a processing 1008 including one or more processing cores, and a power supply 1009. A person skilled in the art may understand that the structure of the health monitoring device shown in FIG. 10 does not constitute a limitation to the health monitoring device, and the health monitoring device may include more components or fewer components than those shown in the figure, or some components may be combined, or a different component deployment may be used. The foregoing RF circuit and/or WiFi module may also be generally referred to as communications components.

The RF circuit 1001 may be configured to receive and send signals during an information receiving and sending process or a call process. Particularly, the RF circuit 1001 receives downlink information from a base station, then delivers the downlink information to one or more processors 1008 for processing, and sends related uplink data to the base station. Generally, the RF circuit 1001 includes, but is not limited to, an antenna, at least one amplifier, a tuner, one or more oscillators, a subscriber identity module (SIM) card, a transceiver, a coupler, a low noise amplifier (LNA), and a duplexer. In addition, the RF circuit 1001 may also communicate with a network and another device by wireless communication. The wireless communication may use any communications standard or protocol, which includes, but is not limited to, Global System for Mobile communications (GSM), General Packet Radio Service (GPRS), Code Division Multiple Access (CDMA), Wideband Code Division Multiple Access (WCDMA), Long Term Evolution (LTE), email, Short Messaging Service (SMS), and the like.

The memory 1002 may be configured to store a software program and module. The processor 1008 runs the software program and module stored in the memory 1002, to implement various functional applications and data processing. The memory 1002 may mainly include a program storage area and a data storage area. The program storage area may store an operating system, an application program required by at least one function (such as a sound playback function and an image display function), and the like. The data storage area may store data (such as audio data and an address book) created according to use of the health monitoring device, and the like. In addition, the memory 1002 may include a high speed random access memory, and may also include a non-volatile memory, such as at least one magnetic disk storage device, a flash memory, or another volatile solid-state storage device. Correspondingly, the memory 120 may further include a memory controller, so as to provide access of the processor 180 and the input unit 130 to the memory 120. Correspondingly, the memory 1002 may further include a memory controller, so as to facilitate access of the processor 1008 and the input unit 1003 to the memory 1002.

The input unit 1003 may be configured to receive input digit or character information, and generate a keyboard, mouse, joystick, optical, or track ball signal input related to the user setting and function control. Specifically, in a specific embodiment, the input unit 1003 may include a touch-sensitive surface and another input device. The touch-sensitive surface, which may also be referred to as a touchscreen or a touch panel, may collect a touch operation of a user on or near the touch-sensitive surface (such as an operation of a user on or near the touch-sensitive surface by using any suitable object or accessory, such as a finger or a stylus), and drive a corresponding connection apparatus according to a preset program. Optionally, the touch-sensitive surface may include two parts: a touch detection apparatus and a touch controller. The touch detection apparatus detects a touch position of the user, detects a signal generated by the touch operation, and transfers the signal to the touch controller. The touch controller receives the touch signal from the touch detection apparatus, converts the touch signal into touch point coordinates, and sends the touch point coordinates to the processor 1008. Moreover, the touch controller can receive and execute a command sent from the processor 1008. In addition, the touch-sensitive surface may be may be a resistive, capacitive, infrared, or surface sound wave type touch-sensitive surface. In addition to the touch-sensitive surface, the input unit 1003 may further include other input device. Specifically, other input devices may include, but is not limited to, one or more of a physical keyboard, a functional key (such as a volume control key or a switch key), a track ball, a mouse, and a joystick.

The display unit 1004 may be configured to display information input by the user or information provided for the user, and various graphical user interfaces of the health monitoring device. The graphical user interfaces may be formed by a graph, a text, an icon, a video, or any combination thereof. The display unit 1004 may include a display panel. Optionally, the display panel may be configured by using a liquid crystal display (LCD), an organic light-emitting diode (OLED), or the like. Further, the touch-sensitive surface may cover the display panel. After detecting a touch operation on or near the touch-sensitive surface, the touch-sensitive surface transfers the touch operation to the processor 1008, so as to determine the type of the touch event. Then, the processor 1008 provides a corresponding visual output on the display panel according to the type of the touch event. Although, in FIG. 10, the touch-sensitive surface and the display panel are used as two separate parts to implement input and output functions, in some embodiments, the touch-sensitive surface and the display panel may be integrated to implement the input and output functions.

The health monitoring device may further include a measurement component 1005, which is a component configured to convert information on a test strip into an electric signal. For example, the measurement component 1005 is a component that converts blood glucose information on a blood glucose test strip contaminated with blood into an electric signal. In different health monitoring devices, functions of the measurement component 1005 are different.

Optionally, the health monitoring device may further include at least one sensor such as an optical sensor, a motion sensor, and other sensors. Specifically, the optical sensor may include an ambient light sensor and a proximity sensor. The ambient light sensor may adjust luminance of the display panel according to brightness of the ambient light. The proximity sensor may switch off the display panel and/or backlight when the health monitoring device is moved to the ear. As one type of motion sensor, a gravity acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, and an infrared sensor, which may be configured in the health monitoring device, are not further described herein.

The audio circuit 1006, a speaker, and a microphone may provide audio interfaces between the user and the health monitoring device. The audio circuit 1006 may convert received audio data into an electric signal and transmit the electric signal to the speaker. The speaker converts the electric signal into a sound signal for output. On the other hand, the microphone converts a collected sound signal into an electric signal. The audio circuit 1006 receives the electric signal and converts the electric signal into audio data, and outputs the audio data to the processor 1008 for processing. Then, the processor 1008 sends the audio data to, for example, another health monitoring device by using the RF circuit 1001, or outputs the audio data to the memory 1002 for further processing. The audio circuit 1006 may further include an earplug jack, so as to provide communication between a peripheral earphone and the health monitoring device.

WiFi is a short distance wireless transmission technology. The health monitoring device may help, by using the WiFi module 1007, the user to receive and send emails, browse a web page, access streaming media, and so on, which provides wireless broadband Internet access for the user. Although FIG. 10 shows the WiFi module 1007, it may be understood that the WiFi module 1007 is not a necessary component of the health monitoring device, and when required, the health monitoring device may be omitted as long as the scope of the essence of the present disclosure is not changed.

The processor 1008 is the control center of the health monitoring device, and is connected to various parts of the mobile phone by using various interfaces and lines. By running or executing the software program and/or module stored in the memory 1002, and invoking data stored in the memory 1002, the processor 1008 performs various functions and data processing of the health monitoring device, thereby performing overall monitoring on the mobile phone. Optionally, the processor 1008 may include one or more processing cores. Preferably, the processor 1008 may integrate an application processor and a modem. The application processor mainly processes an operating system, a user interface, an application program, and the like. The modem mainly processes wireless communication. It may be understood that the foregoing modem may either not be integrated into the processor 1008.

The health monitoring device further includes the power supply 1009 (such as a battery) for supplying power to the components. Preferably, the power supply may be logically connected to the processor 1008 by using a power management system, thereby implementing functions such as charging, discharging and power consumption management by using the power management system. The power supply 1009 may further include one or more of a direct current or alternating current power supply, a re-charging system, a power failure detection circuit, a power supply converter or inverter, a power supply state indicator, and any other components.

Although not shown in the figure, the health monitoring device may further include a camera, a Bluetooth module, and the like, which are not further described herein. Specifically, in this embodiment, the processor 1008 in the health monitoring device runs one or more program instructions stored in the memory 1002, so as to implement the methods for obtaining a health consultation service according to the foregoing various method embodiments.

A person of ordinary skill in the art may understand that all or some of the steps in the methods for obtaining a health consultation service in the foregoing embodiments may be performed by a program instructing relevant hardware. The program may be stored in a computer readable storage medium. The storage medium may be an ROM, an RAM, a magnetic disk, an optical disc, or the like.

An embodiment of the present disclosure further provides a system for obtaining a health consultation service. The system includes a first apparatus and a second apparatus. The first apparatus is the apparatus for obtaining a health consultation service shown in FIG. 6 or FIG. 7, and the second apparatus is the apparatus for obtaining a health consultation service shown in FIG. 8. Alternatively, an embodiment of the present disclosure further provides a system for obtaining a health consultation service. The system includes a server and a health monitoring device. The server is the server shown in FIG. 9, and the health monitoring device is the health monitoring device shown in FIG. 10.

After a health consultation request is received, a contact method of a doctor who provides a consultation service to a patient is obtained, and then the health consultation request is forwarded to a doctor terminal according to the contact method of the doctor. The health consultation request is used to request the doctor to provide a health consultation service to the patient according to the contact method of the patient. In this way, the problem in the prior art that a patient can obtain a health consultation service only after the patient performs registration in hospital, resulting in low efficiency of obtaining the health consultation service is resolved, and the effect of improving the efficiency of obtaining, by the patient, the health consultation service can be achieved.

Based on the above, according to the system for obtaining a health consultation service according to this embodiment, after a health consultation request is received, a contact method of a doctor who provides a consultation service to a patient is obtained, and then a health consultation request is forwarded to a doctor terminal according to the contact method of the doctor; the health consultation request is used to request the doctor to provide a health consultation service to the patient according to a contact method of the patient. In this way, the problem in the prior art that a patient can obtain a health consultation service only after the patient performs registration in hospital, resulting in low efficiency of obtaining the health consultation service is resolved, and the effect of improving the efficiency of obtaining, by the patient, the health consultation service can be achieved.

The sequence numbers of the foregoing embodiments of the present disclosure are merely for the convenience of description, and do not imply the preference among the embodiments.

A person of ordinary skill in the art may understand that all or some of the steps of the foregoing embodiments may be performed by using hardware, or may be implemented by a program instructing relevant hardware. The program may be stored in a computer readable storage medium. The storage medium may be an ROM, a magnetic disk, an optical disc, or the like.

The foregoing descriptions are merely preferred embodiments of the present disclosure, but are not intended to limit the present disclosure. Any modification, equivalent replacement, or improvement made within the spirit and principle of the present disclosure shall fall within the protection scope of the present disclosure.

Figure 11:
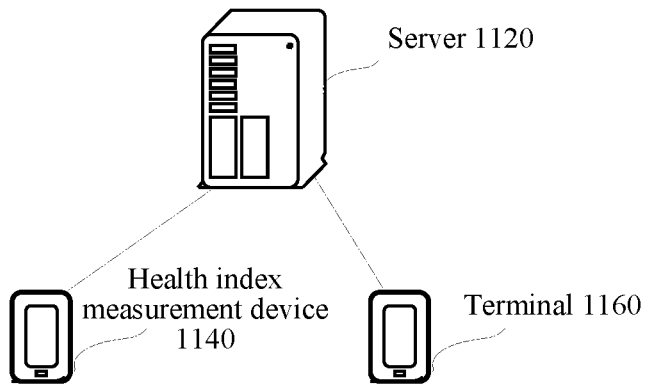
FIG. 11 is a schematic structural diagram of an implementation environment according to an embodiment of the present disclosure.

Referring to FIG. 11, FIG. 11 is a schematic structural diagram of an implementation environment according to an embodiment of the present disclosure. The implementation environment includes a server 1120, a health index measurement device 1140, and a terminal 1160. The health index measurement device 1140, as used herein, may also be referred as health management apparatus.

A connection is established between the server 1120 and the health index measurement device 1140 by using a wireless network or a wired network. Information issued by the health index measurement device 1140 is processed by the server 1120, and then is sent to a communications application program that runs in the terminal 1160.

The server 1120 is a background server of the communications application program. The server 1120 may be one server, a server cluster formed by multiple servers, or a cloud computing center.

The health index measurement device 1140 may be a blood glucose meter, a sphygmomanometer, a fat meter, a skin detector, a traditional Chinese medical meridian detector, or the like. Optionally, as the health index measurement device 1140 becomes smaller and portable, the health index measurement device 1140 is a portable health index measurement device, or a household health index measurement device. That is, the use range of the health index measurement device 1140 is more in a family environment, rather than a hospital, a clinic, or a pharmacy. In the following embodiments, description is made by using that the health index measurement device 1140 is a portable blood glucose meter as an example.

The terminal 1160 may be a mobile phone, a tablet computer, an ebook reader, a Moving Picture Experts Group Audio Layer III (MP3) player, a Moving Picture Experts Group Audio Layer IV (MP4) player, a laptop computer, a desktop computer, or the like. A communications application program is installed in the terminal 1160. The communications application program may be an application program having social attributes, such as an instant messaging program, a video communications program, or a voice communications program. A user communicates with other users in the communications application program by using a social account. For example, the communications application program is an instant messaging program, such as QQ, a microblog, or WeChat.

A connection is established between the terminal 1160 and the server 1120 by using a wireless network or a wired network.

Figure 12:
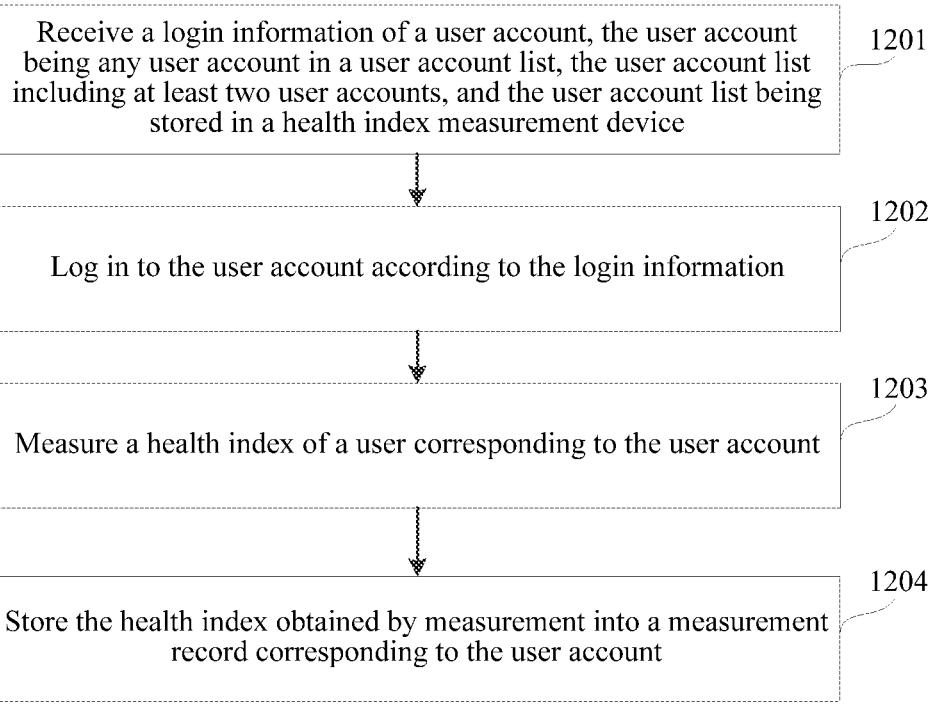
FIG. 12 is a method flowchart of a health index measurement method according to an embodiment of the present disclosure.

Referring to FIG. 12, FIG. 12 is a method flowchart of a health index measurement method according to an embodiment of the present disclosure. This embodiment is described by using that the health index measurement method is applied to the health index measurement device shown in FIG. 11 as an example. The method includes:

Step 1201: Receive login information of a user account, the user account being any user account in a user account list, the user account list including at least two user accounts, and the user account list being stored in a health index measurement device.

The health index measurement device receives login information of a user account, and the login information is used to log in to the user account in the health index measurement device.

Step 1202: Log in to the user account according to the login information.

The health index measurement device logs in to the user account corresponding to login information in the health index measurement device according to the received login information.

Step 1203: Measure a health index of a user corresponding to the user account. The heath index, as used herein, may be also referred as physiological data of the user.

After login of the user account succeeds, the health index measurement device performs health index measurement on a user corresponding to the user account.

Step 1204: Store the health index obtained by measurement into a measurement record corresponding to the user account.

The health index measurement device stores a health index obtained by the measurement into a measurement account corresponding to the user account.

The measurement record may be recording table in an electronic form. Each user account corresponds to one recording table, in which a health index corresponding to the user account is recorded.

Optionally, a measurement time of the health index of the user account and/or a result of comparison between the health index obtained by the measurement and a normal index are also recorded in the measurement record.

In some embodiments, the method may include: storing, by the health index measurement device 1140, a user account list comprising multiple user accounts, and profiles corresponding to the multiple use accounts, each of the profiles including: login information corresponding to each of the multiple user accounts, a medical record corresponding to each of the multiple user accounts, and contact information of a remote terminal corresponding to each of the multiple user accounts; displaying, by a graphical interface, the user account list; receiving, from the graphical interface, a selection of the first user account; and after receiving the login information of the first user account, obtaining the profile corresponding to the first user account.

Based on the above, according to the health index measurement method provided in this embodiment, a user account mechanism is provided in a health index measurement device, so that the problem that a user has to manually record a health index onto a recording card of the corresponding user after measurement of each time is completed, resulting in easy occurrence of obfuscated data is resolved, and when multiple family members use a same health index measurement device, the health index measurement device automatically stores health indexes of the family members into corresponding measurement records, thereby implementing automatic aggregation management on health indexes of the family members.

Because health index measurement devices are disposed in hospitals, clinics, and pharmacies in the past for use by multiple users. The users incidentally and randomly use the health index measurement devices, and therefore the problem of dedicated use is not considered during conventional designs. In addition, the design intention of a health index measurement device is to measure a health index of a user, rather than human-computer interaction between the health index measurement device and the user. In conventional thoughts of a person skilled in the art, the health index measurement device does not need a user account. However, in an optional implementation of this embodiment of the present disclosure, it is hoped that the health index measurement device is popularized into a household health index measurement device for use by a limited number of family members. The family members use the health index measurement device for a long term, and therefore a user account mechanism is provided in the health index measurement device of this embodiment of the present disclosure, to implement classified aggregation and long-term recording of health indexes of the family members.

Figure 13A:
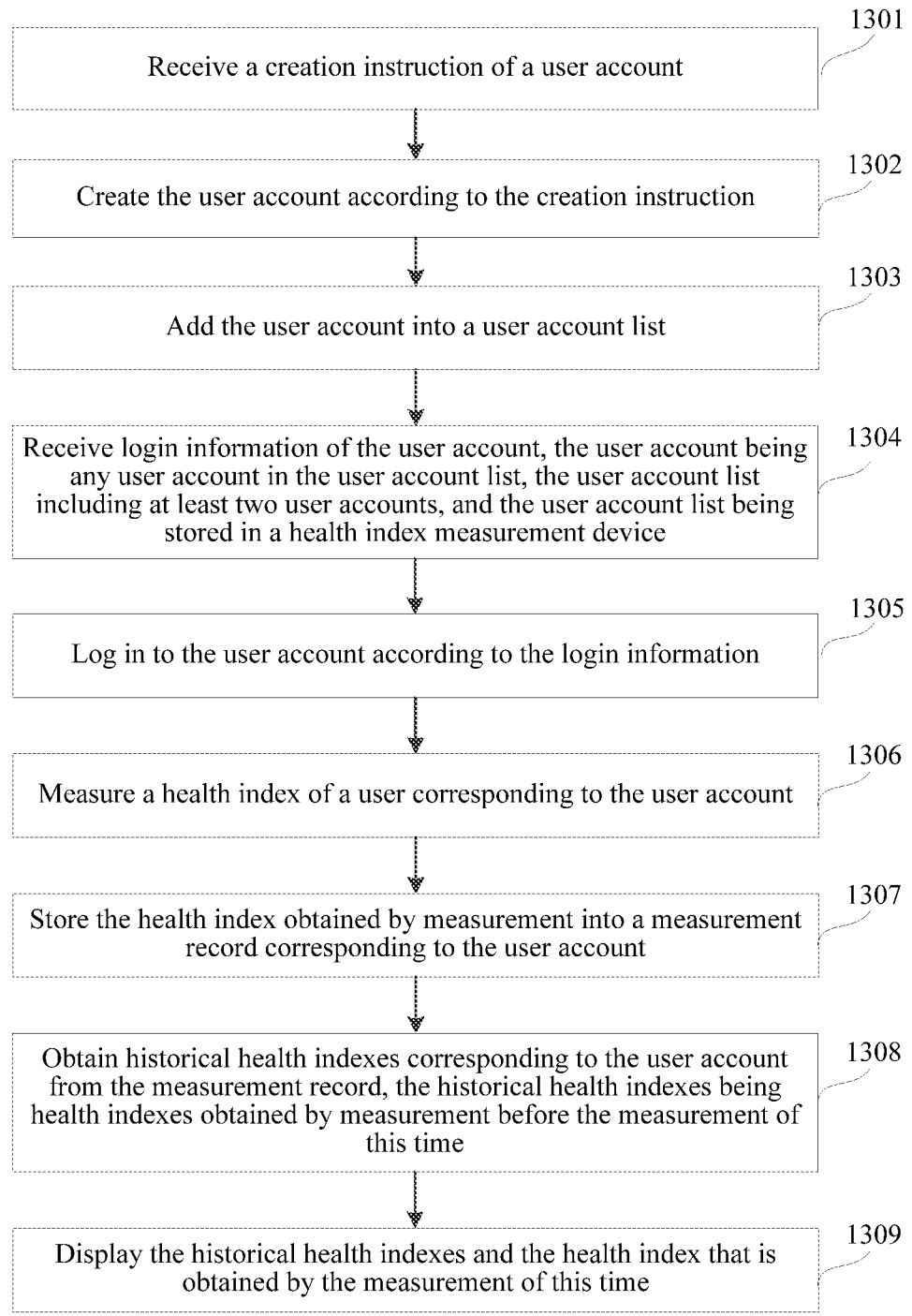
FIG. 13A is a method flowchart of a health index measurement method according to another embodiment of the present disclosure.

Referring to FIG. 13A, FIG. 13A is a method flowchart of a health index measurement method according to another embodiment of the present disclosure. This embodiment is described by using that the health index measurement method is applied to the implementation environment shown in FIG. 11 as an example. The method includes:

Step 1301: Receive a creation instruction of a user account.

When a user needs to use a same health index measurement device, the user first clicks "create a user account" in the health index measurement device.

Correspondingly, the health index measurement device receives a creation instruction of a user account. The creation instruction of the user account is used to create the user account in the health index measurement device, so that the user performs health index measurement by using the health index measurement device.

Step 1302: Create the user account according to the creation instruction.

The creation instruction is an instruction for creating a user account. The user account includes a user account number and a password.

After receiving the creation instruction, the health index measurement device obtains the user account carried in the creation instruction, and creates the corresponding user account for the user according to the obtained user account.

Figure 13B:
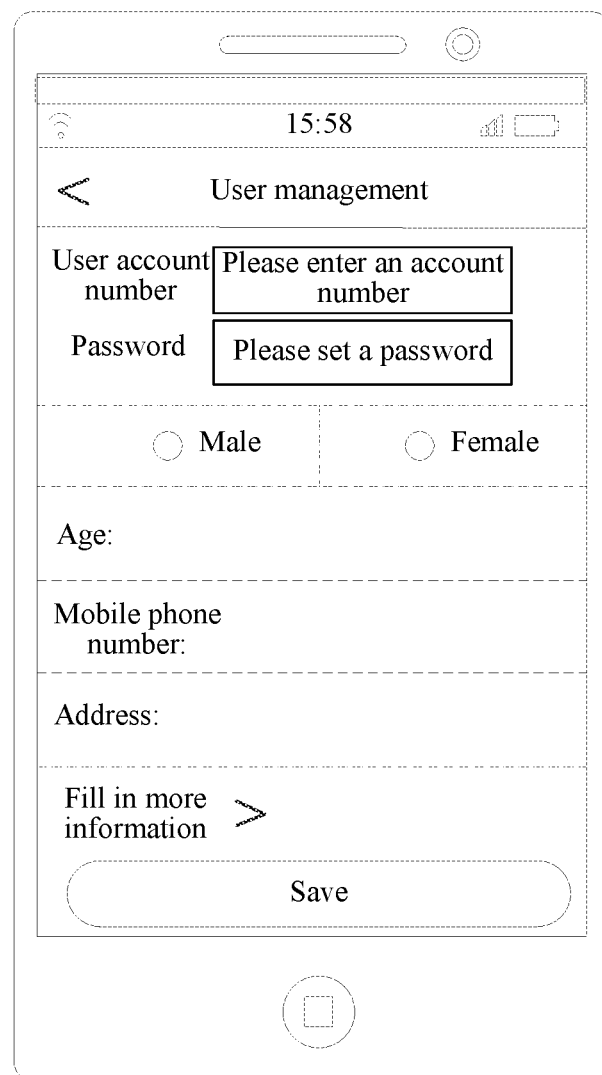
FIG. 13B is a schematic diagram of an interface of user account creation according to an embodiment of the present disclosure.

When the user account is created, a user account number and a password of the user account need to be input. Optionally, user information further needs to be input. The user information includes information such as: gender, age, body weight, a mobile phone number, and a contact address, as shown in FIG. 13B.

Step 1303: Add the user account into a user account list.

After creating the user account, the health index measurement device adds the created user account into a user account list, so as to directly select the user account for login next time.

Figure 14A:
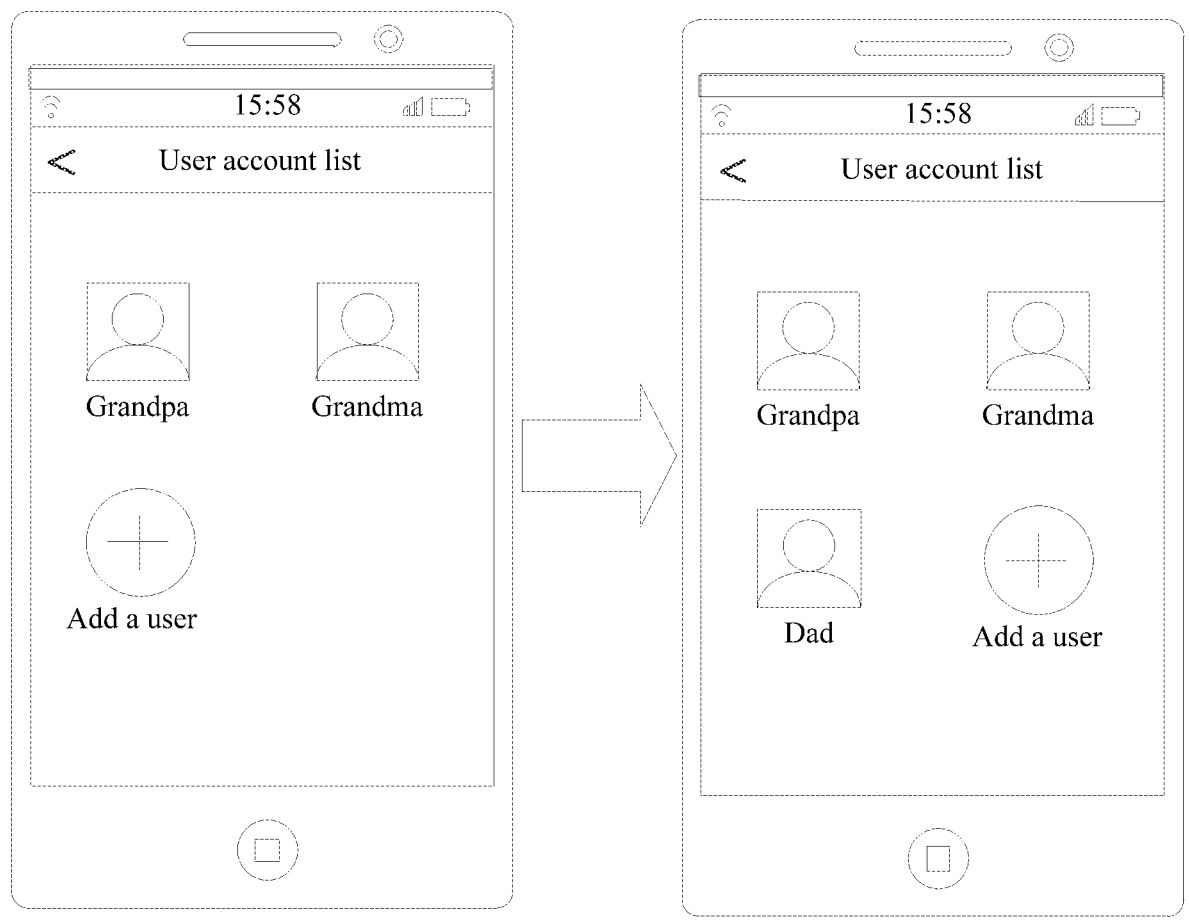
FIG. 14A is a schematic diagram of an interface showing a varied quantity of user accounts in a user account list according to an embodiment of the present disclosure.

For example, the user account list stored in the health index measurement device originally stores a user account "grandpa" and a user account "grandma". To monitor health indexes of family members, dad hopes to create a user account "dad". Then dad clicks an instruction of creating a user account "dad" in the health index measurement device. After receiving the instruction, the health index measurement device creates a user account "dad" according to "dad" carried in the instruction, and simultaneously adds the created user account into the user account list. In this case, three user accounts, which are respectively "grandpa", "grandma", and "dad" are stored in the user account list. Changes in the user account list are shown in FIG. 14A.

Step 1304: Receive login information of the user account, the user account being any user account in the user account list, the user account list including at least two user accounts, and the user account list being stored in a health index measurement device.

According to the related information that is input when the user account is created in step 1302, during login of the user account, the user account and password input in a login information input box are received, and are determined as login information of the user account.

Figure 14B:
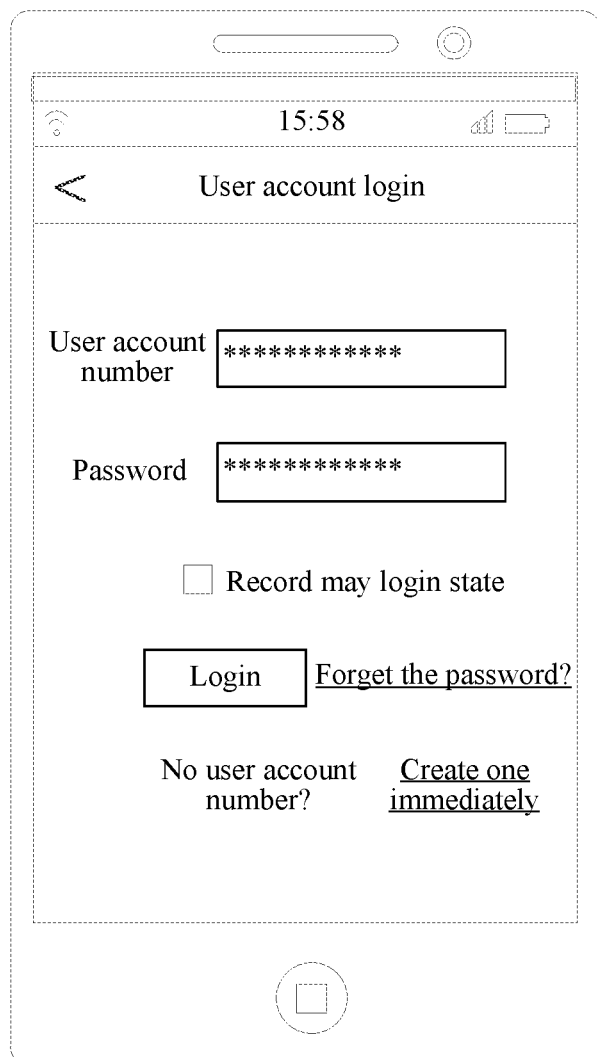
FIG. 14B is a schematic diagram of an interface of login information of a user account according to an embodiment of the present disclosure.

When needing to log in to the health index measurement device, the user selects an account login interface in the health index measurement device, in which the login information input box appears, and the user enters the corresponding user account and password in the login information input box, and the health index measurement device determines the input user account and password as the login information of the corresponding user account, as shown in FIG. 14B.

If a user needing measurement is a member in the user account list, the user directly selects a user account corresponding to himself/herself from the user account list, and clicks login in the health index measurement device. If the user needing measurement is not a member in the user account list, step 1301 needs to be first performed.

Correspondingly, the health index measurement device receives the login information of the user account. The login information is used to log in to the user account in the health index measurement device. The user account may be any user account in the user account list. The user account list includes at least two user accounts.

The user account list is pre-stored in the health index measurement device, and the user may query in the health index measurement device when selecting the corresponding user account.

Optionally, if there is only one user account in the user account list, after the health index measurement device is started, the user account is automatically selected for login.

Step 1305: Log in to the user account according to the login information.

The health index measurement device logs in to the user account carried in the login information in the health index measurement device according to the received login information.

Step 1306: Measure a health index of a user corresponding to the user account.

Figure 14C:
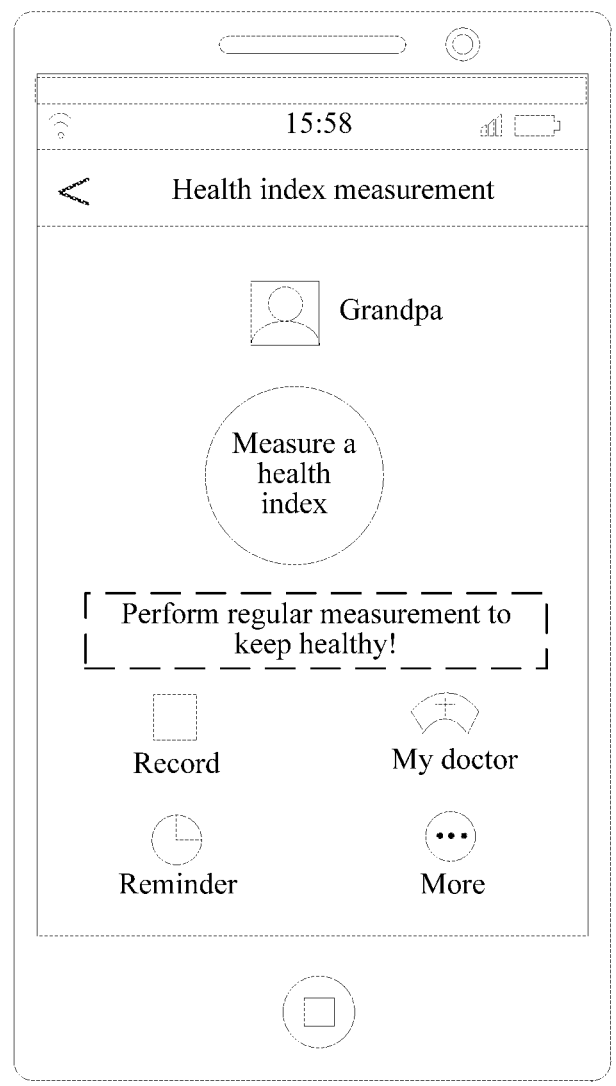
FIG. 14C is a schematic diagram of an interface of health index measurement according to an embodiment of the present disclosure.

After login of the user account succeeds, the health index measurement device performs health index measurement on the user corresponding to the user account, as shown in FIG. 14C. The "my doctor" icon on the graphical interface may be used to trigger a health consultation request according to the embodiments described in FIGS. 2-4B.

Step 1307: Store the health index obtained by measurement into a measurement record corresponding to the user account. The measurement record, as used herein, may also be referred as medical record.

The health index measurement device stores a health index obtained by the measurement into a measurement account corresponding to the user account.

The measurement record may be recording table. Each user account corresponds to one recording table, in which a health index corresponding to the user account is recorded.

Optionally, a measurement time of the health index of the user account and/or a result of comparison between the health index obtained by the measurement and a normal index are also recorded in the measurement record.

Figure 14D:
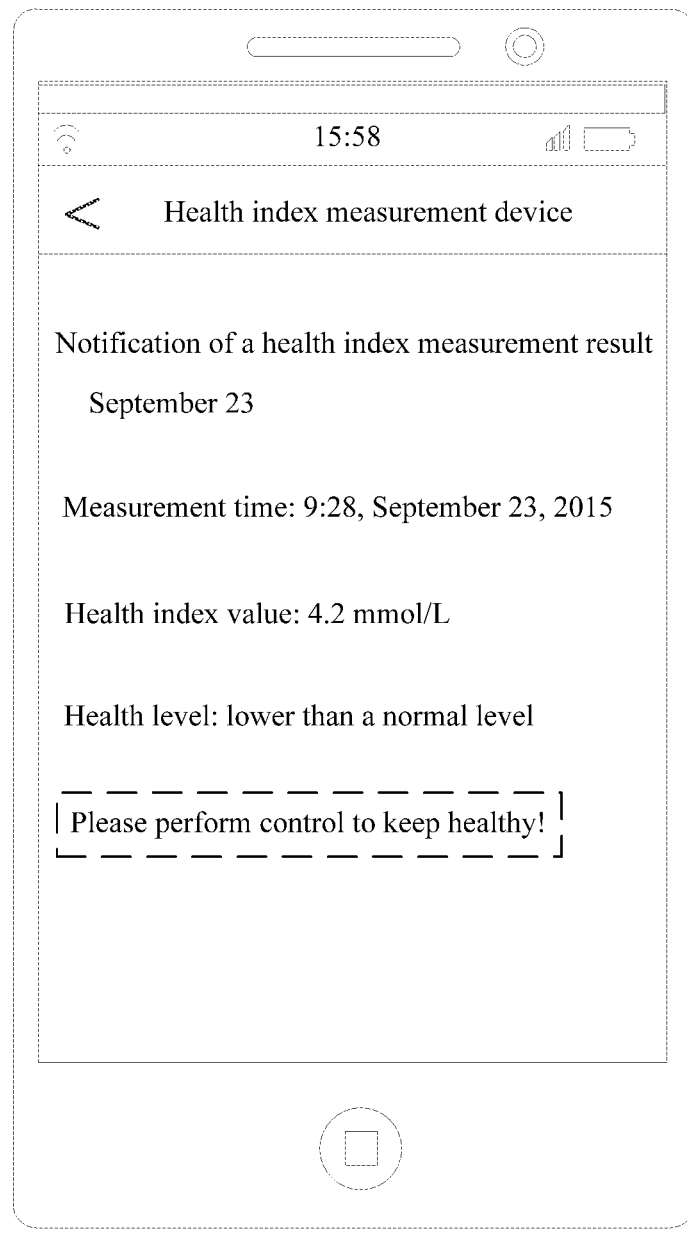
FIG. 14D is a schematic diagram of an interface of notification of a health index measurement result according to an embodiment of the present disclosure.

For example, on September 123, grandpa measures his health index by using the health index measurement device, and a measurement result is notified as: measurement time: 19:28, Sep. 123, 12015; health index value: 14.2 mmol/L; health level: lower than a normal level, as shown in FIG. 14D.

Step 1308: Obtain historical health indexes corresponding to the user account from the measurement record, the historical health indexes being health indexes obtained by measurement before the measurement of this time.

After the health index measurement is completed, the user may query historical health indexes corresponding to the user account from the measurement record according to the user account. The historical health indexes carry a quantity of times of measurement of the user account, and separately provide a quantity of times of detection of a normal health index, a quantity of times of detection of a health index higher than a normal level, and a quantity of times of detection of a health index lower than the normal level, and time of measurement each time, and a health index corresponding to the measurement each time.

Step 1309: Display the historical health indexes and the health index that is obtained by the measurement of this time.

The health index measurement device displays, at a display position, the obtained historical health indexes corresponding to the user account and a health index that is obtained by measurement of this time.

Figure 14E:
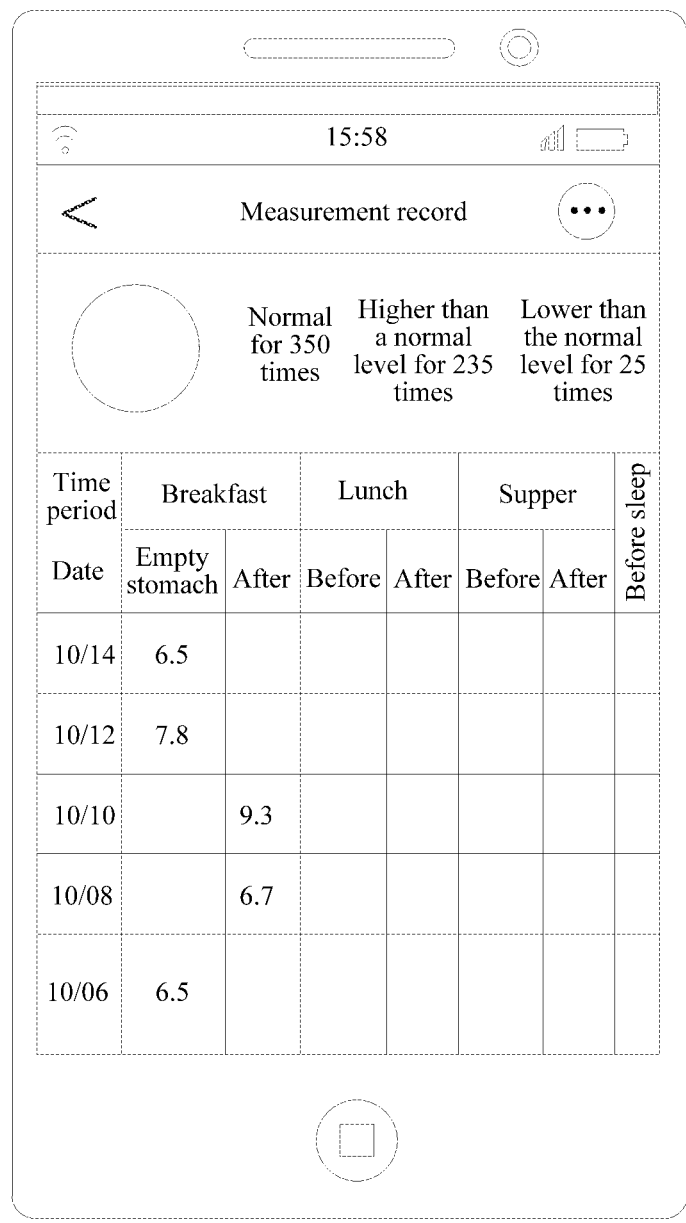
FIG. 14E is a schematic diagram of an interface of a health index measurement record according to an embodiment of the present disclosure.

The quantity of times of measurement of the user account, the quantity of times of detection of a normal health index, the quantity of times of detection of a health index higher than a normal level, the quantity of times of detection of a health index lower than the normal level, and health indexes obtained by measurement of latest several times and corresponding time are displayed on a display interface of the health index measurement device, as shown in FIG. 14E.

Figure 15A:
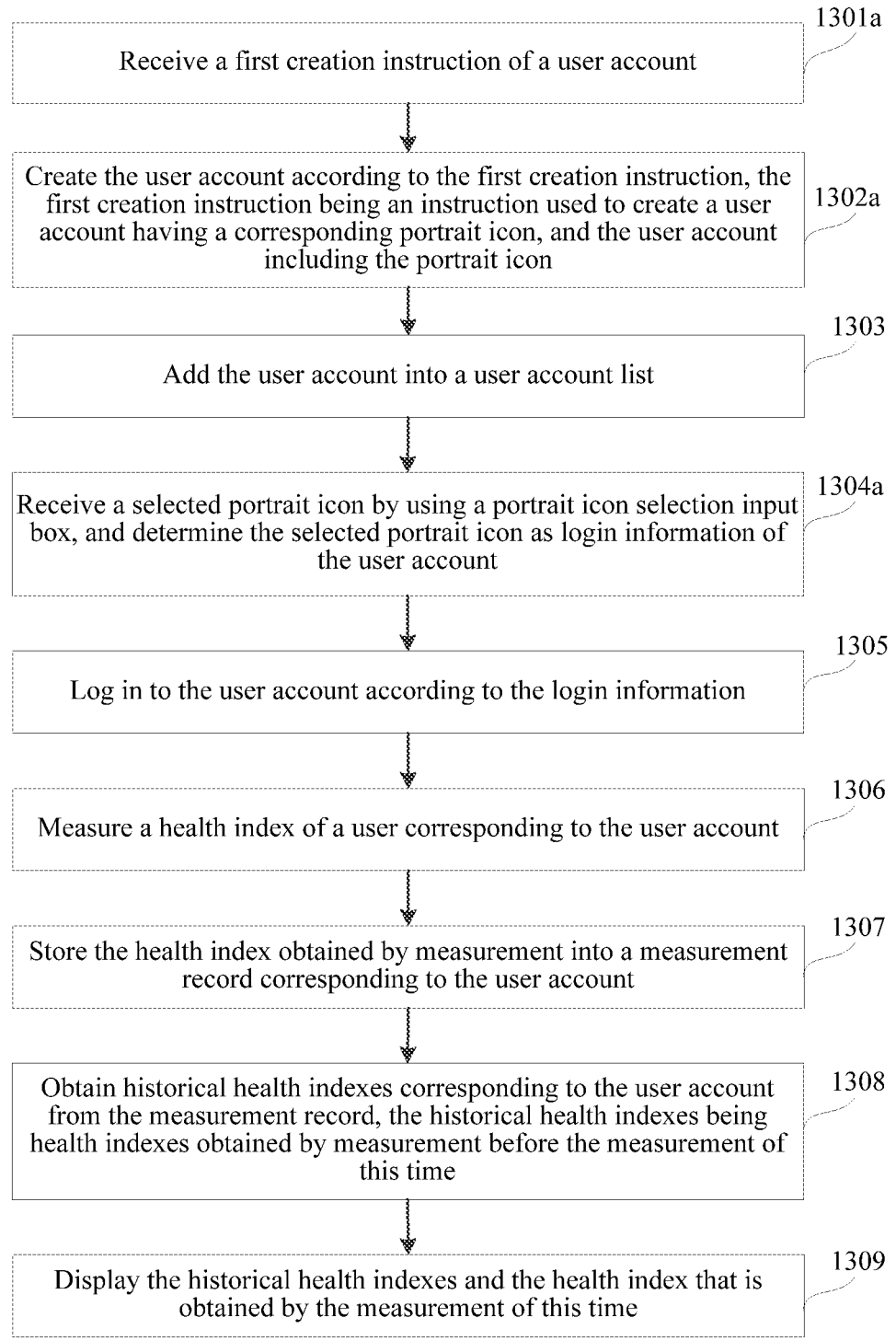
FIG. 15A is a method flowchart of a health index measurement method according to an embodiment of the present disclosure.

In the embodiment of FIG. 13A, the user account and password are determined as the login information of the user account. Optionally, in a first possible implementation, the foregoing step 1301, step 1302, and step 1304 can be replaced for implementation into step 1301*a*, step 1302*a*, and step 1304*a*, as shown in FIG. 15A:

Step 1301*a*: Receive a first creation instruction of a user account.

Step 1302*a*: Create the user account according to the first creation instruction, the first creation instruction being an instruction used to create a user account having a corresponding portrait icon, and the user account including the portrait icon.

After receiving a first creation instruction, a health index measurement device obtains a portrait icon corresponding to a user account carried in the first creation instruction, and creates the corresponding user account for a user according to the obtained portrait icon corresponding to the user account.

Optionally, the health index measurement device pre-stores multiple different portrait icons. When a user account is created, different user accounts are created by selecting different portrait icons. In other words, at least two preset user accounts are provided in the health index measurement device, and each preset user account corresponds to a portrait icon of a preset family role, for example, a portrait icon of grandpa, grandma, dad, mom, son, daughter, grandfather, grandmother, default user 11, or default user 12. The preset user account is a user account that is provided by the health index measurement device in default, and does not need to be created by the user himself/herself, and the user can directly use the preset user account after switch-on.

Optionally, the preset user account corresponds to default user information. The user can modify the user information by himself/herself after using the preset user account. The user information includes information such as: gender, age, body weight, a mobile phone number, and a contact address.

When a family member uses the health index measurement device for the first time, the family member selects a user account from the preset user accounts for use according to a family role that the family member belongs without creating a user account by himself/herself.

Step 1304*a*: Receive a selected portrait icon by using a portrait icon selection input box, and determine the selected portrait icon as login information of the user account.

Figure 15B:
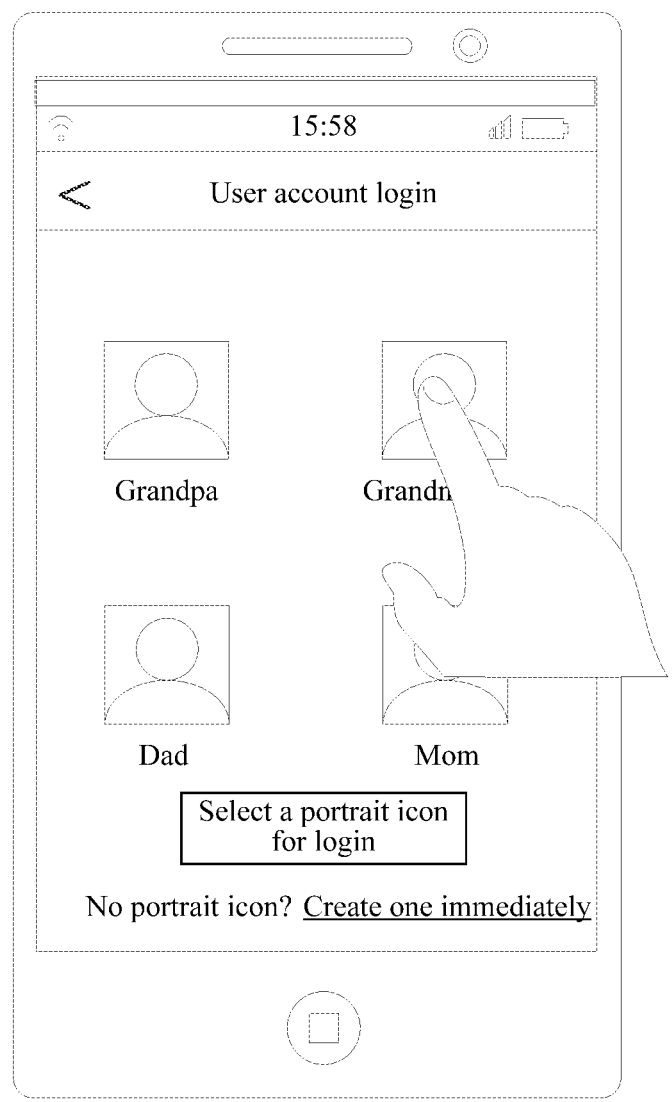
FIG. 15B is a schematic diagram of an interface of login information of a user account according to an embodiment of the present disclosure.

When needing to log in to the health index measurement device, the user selects an account login interface in the health index measurement device, and a portrait icon selection input box appears on the account login interface; that is, a series of portrait ions appear on the login interface; the user clicks a portrait icon corresponding to the user in the portrait icons that appear, and the health index measurement device determines the clicked portrait icon as login information of the user account, as shown in FIG. 15B.

Optionally, the portrait icon selection input box includes at least two portrait icons of preset family roles. The at least two portrait icons of preset family roles are portrait icons owned by the preset user accounts provided, in default, by the health index measurement device.

Based on the above, according to the health index measurement method provided in this embodiment, a health index measurement device creates corresponding user accounts according to different portrait icons, and determines a selected portrait icon as login information of a user account, so as to avoid operation of inputting complex information when determining a user account number and a password as the login information of the user account, thereby achieving the effect of creating a user account and logging in to the user account more easily.

According to the health index measurement method provided in this embodiment, the health index measurement device provides preset user accounts, and a user directly uses a preset user account according to a family role without creating a user account by himself/herself, so that users with poor operating capacities such as old people and patients can also conveniently use the health index measurement device.

Figure 15C:
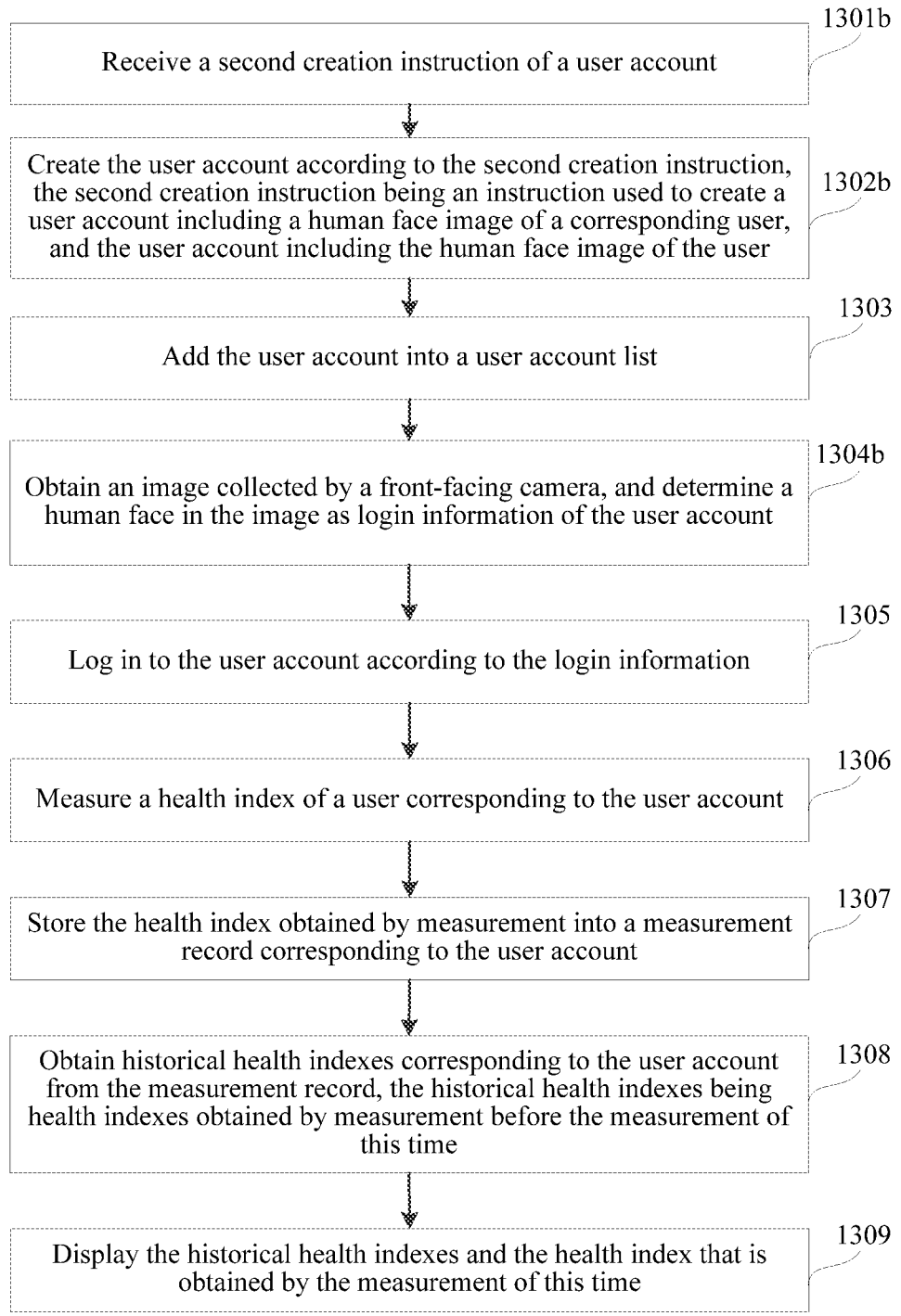
FIG. 15C is a method flowchart of a health index measurement method according to another embodiment of the present disclosure.

In a second possible implementation, the foregoing step 1301, step 1302, and step 1304 can be replaced for implementation into step 1301*b*, step 1302*b*, and step 1304*b*, as shown in FIG. 15C:

Step 1301*b*: Receive a second creation instruction of a user account.

Step 1302*b*: Create the user account according to the second creation instruction, the second creation instruction being an instruction used to create a user account including a human face image of a corresponding user, and the user account including the human face image of the user.

After receiving a second creation instruction, a health index measurement device collects a human face image of a user by using a front-facing camera, extracts human face features from a human face in the human face image, and creates a corresponding user account for the user according to the extracted human face features.

Step 1304*b*: Obtain an image collected by a front-facing camera, and determine a human face in the image as login information of the user account.

When needing to log in to the health index measurement device, a user selects a login interface in the health index measurement device. In this case, the health index measurement device starts a front-facing camera, collects the image of the user, and extracts the human face from the image. The health index measurement device determines the human face in the image collected by the front-facing camera as login information of the user account.

Schematically, when the human face in the collected image satisfies the human face features of the user account, the health index measurement device logs in to the user account.

Based on the above, according to the health index measurement method provided in this embodiment, a health index measurement device creates a corresponding user account by collecting a human face image of a user by using a front-facing camera, and determines a human face in the collected image as login information of the user account, so as to avoid operation of inputting complex information when determining a user account number and a password as the login information of the user account, thereby achieving the effect of creating a user account and logging in to the user account more easily.

Figure 15D:
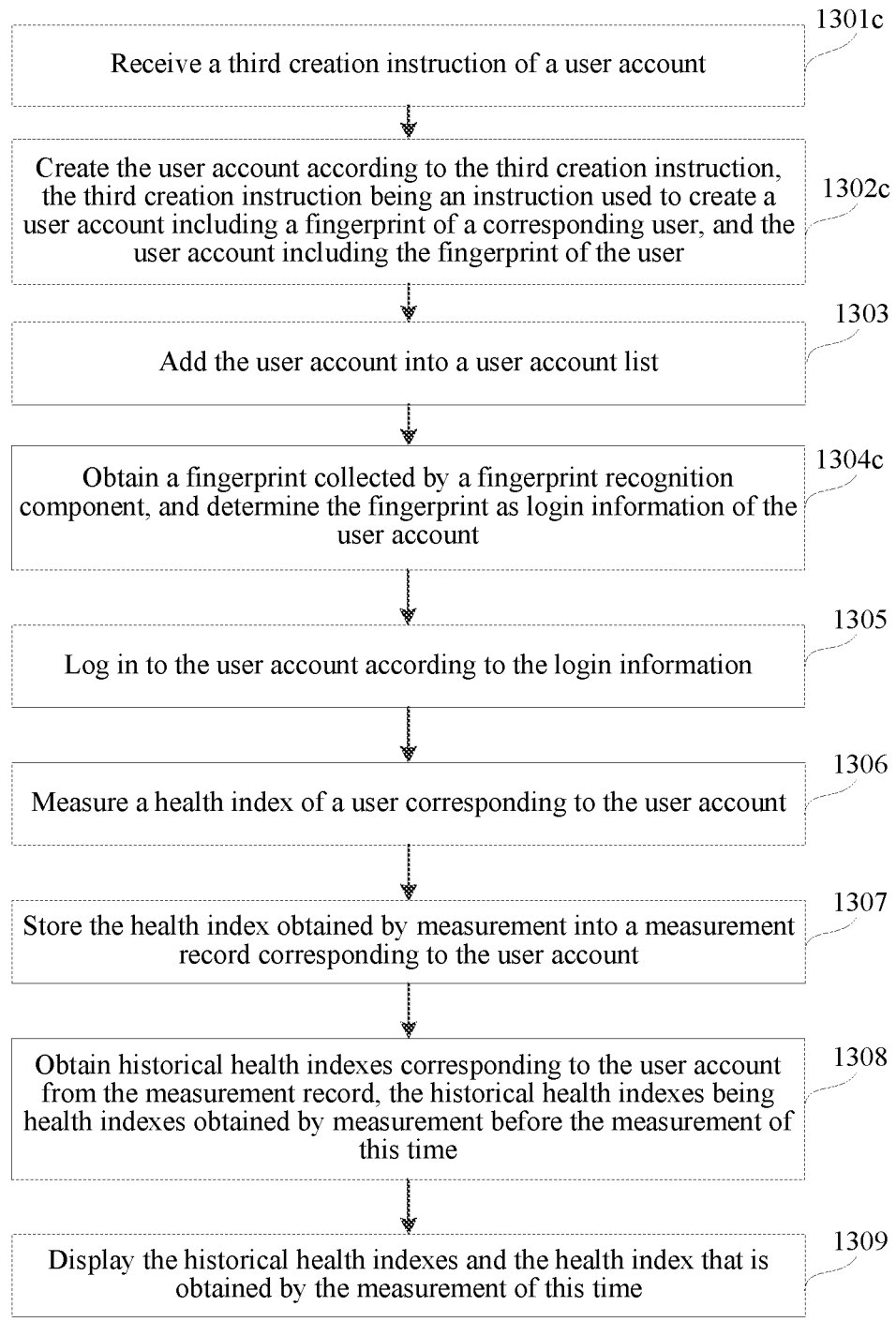
FIG. 15D is a method flowchart of a health index measurement method according to another embodiment of the present disclosure.

In a third possible implementation, the foregoing step 1301, step 1302, and step 1304 can be replaced for implementation into step 1301*c*, step 1302*c*, and step 1304*c*, as shown in FIG. 15D:

Step 1301*c*: Receive a third creation instruction of a user account.

Step 1302*c*: Create the user account according to the third creation instruction, the third creation instruction being an instruction used to create a user account including a fingerprint of a corresponding user, and the user account including the fingerprint of the user.

After receiving a third creation instruction, a health index measurement device collects a fingerprint of a user by using a fingerprint recognition component, extracts fingerprint features in the fingerprint of the user, and creates a corresponding user account for the user according to the fingerprint features.

Step 1304*c*: Obtain a fingerprint collected by a fingerprint recognition component, and determine the fingerprint as login information of the user account.

Figure 15E:
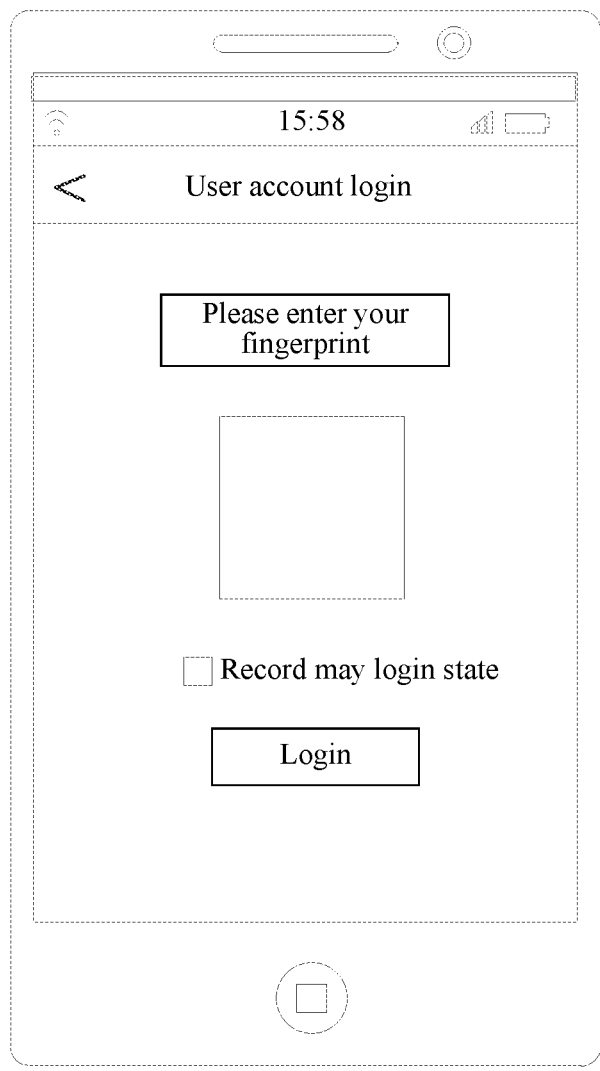
FIG. 15E is a schematic diagram of an interface of login information of a user account according to another embodiment of the present disclosure.

When needing to log in to the health index measurement device, the user selects an account login interface in the health index measurement device; information "please input your fingerprint" appears on the account login interface; in this case, the user only needs to input corresponding fingerprint interface at a specified position, and the health index measurement device determines a fingerprint collected by a fingerprint recognition component as login information of the user account, as shown in FIG. 15E.

Schematically, when the collected fingerprint matches the fingerprint features of the user account, the health index measurement device logs in to the user account.

Based on the above, according to the health index measurement method provided in this embodiment, a health index measurement device creates a corresponding user account by collecting a fingerprint of a user by using a fingerprint recognition component, and determines the collected fingerprint as login information of the user account, so as to avoid operation of inputting complex information when determining a user account number and a password as the login information of the user account, thereby achieving the effect of creating a user account and logging in to the user account more easily.

Figure 15F:
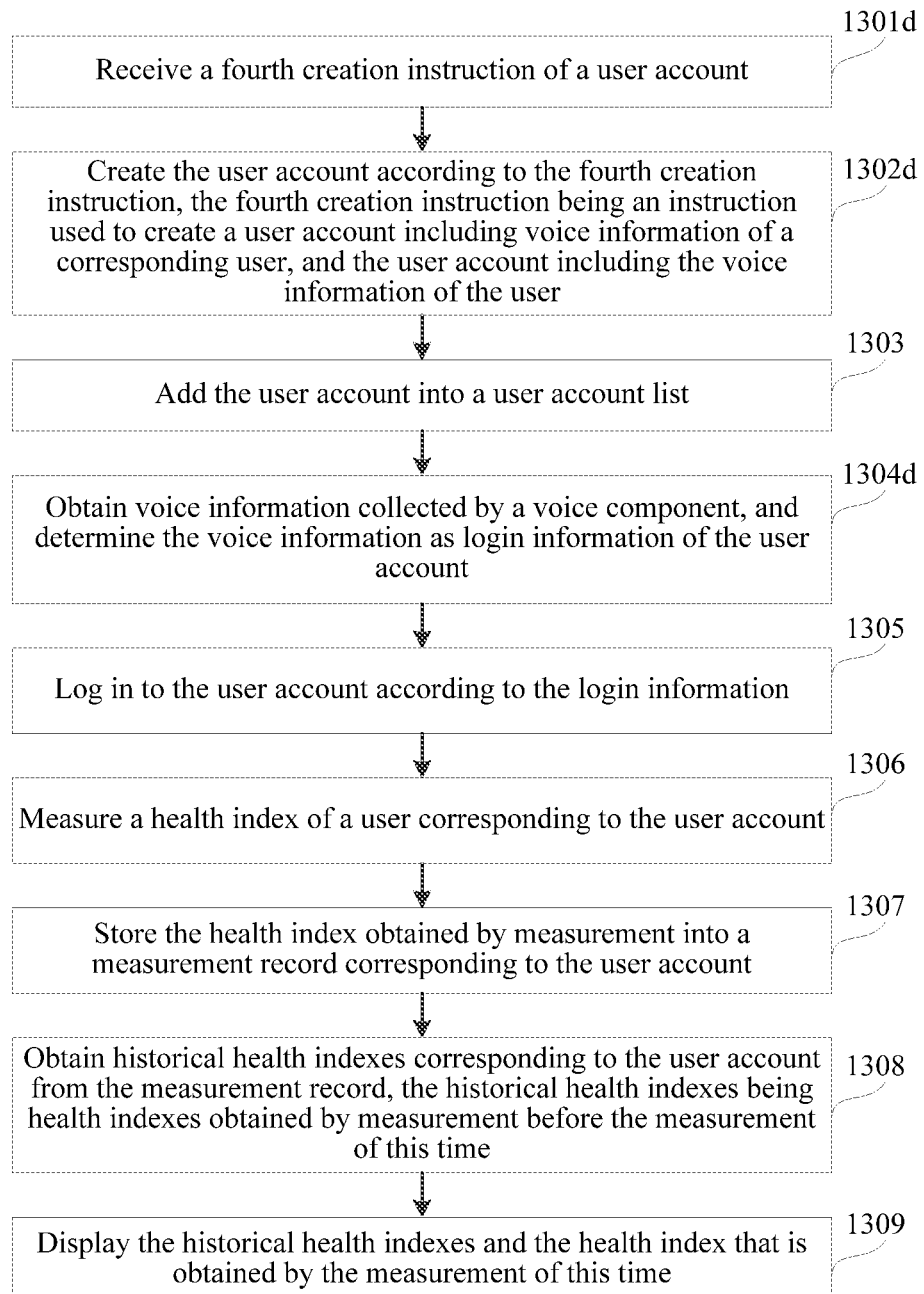
FIG. 15F is a method flowchart of a health index measurement method according to another embodiment of the present disclosure.

In a fourth possible implementation, the foregoing step 1301, step 1302, and step 1304 can be replaced for implementation into step 1301*d*, step 1302*d*, and step 1304*d*, as shown in FIG. 15F:

Step 1301*d*: Receive a fourth creation instruction of a user account.

Step 1302*d*: Create the user account according to the fourth creation instruction, the fourth creation instruction being an instruction used to create a user account including voice information of a corresponding user, and the user account including the voice information of the user.

After receiving a fourth creation instruction, a health index measurement device collects voice information of a user by using a voice component, extracts voiceprint features in the voice information, and creates a corresponding user account for the user according to the voiceprint features.

Step 1304*d*: Obtain voice information collected by a voice component, and determine the voice information as login information of the user account.

When needing to log in to the health index measurement device, the user selects an account login interface in the health index measurement device. In this case, the health index measurement device starts a voice function, and the user only needs to speak for a period in front of the health index measurement device, which determines voice information collected by a voice component as login information of the user account.

Schematically, when the collected voice information satisfies the voiceprint features of the user account, the health index measurement device logs in to the user account.

Based on the above, according to the health index measurement method provided in this embodiment, a health index measurement device creates a corresponding user account by collecting voice information of a user by using a voice component, and determines the collected voice information as login information of the user account, so as to avoid operation of inputting complex information when determining a user account number and a password as the login information of the user account, and implement automation of user account creation and login, thereby achieving the effect of creating a user account and logging in to the user account more easily.

Figure 15G:
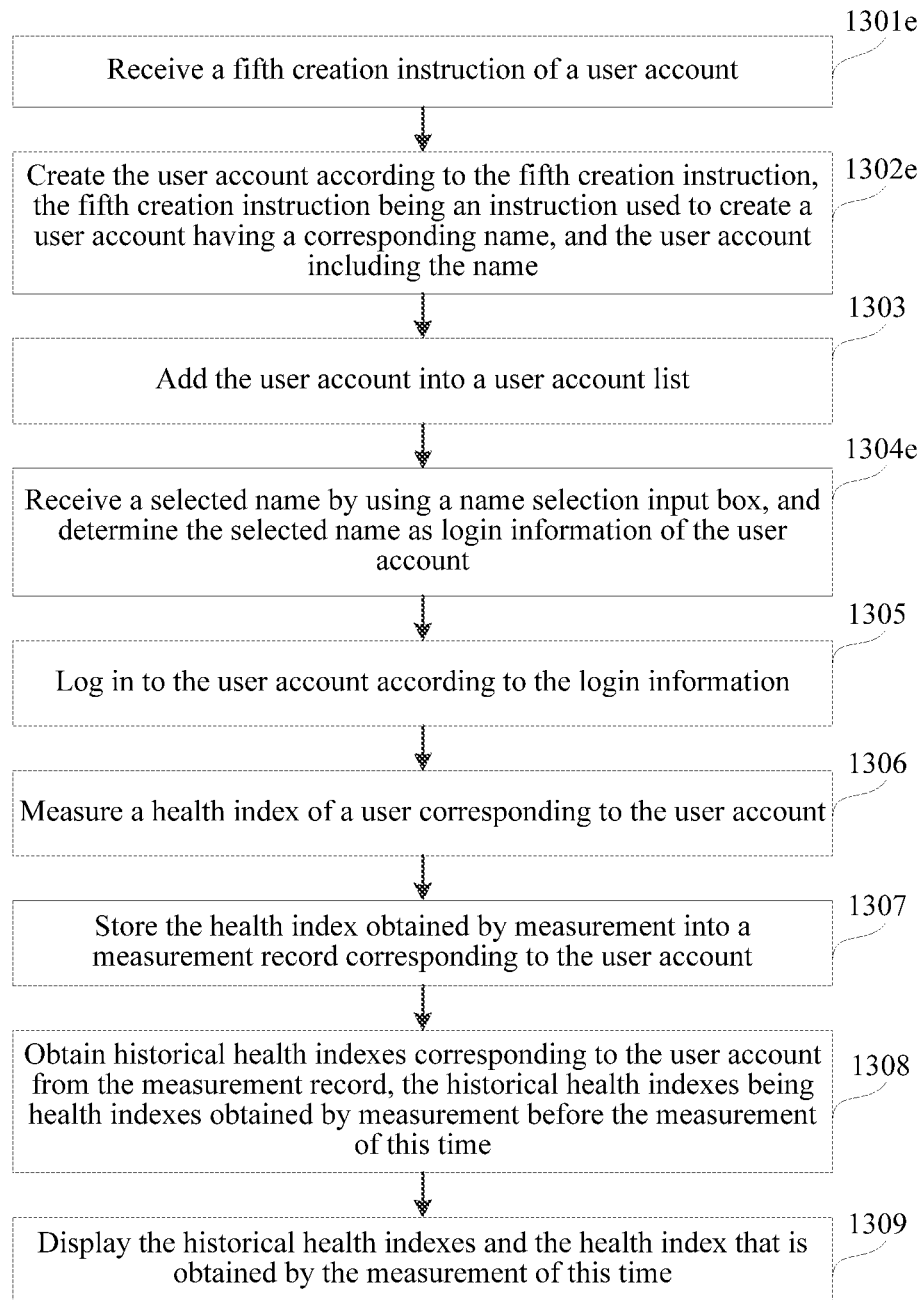
FIG. 15G is a method flowchart of a health index measurement method according to still another embodiment of the present disclosure.
Figure 15H:
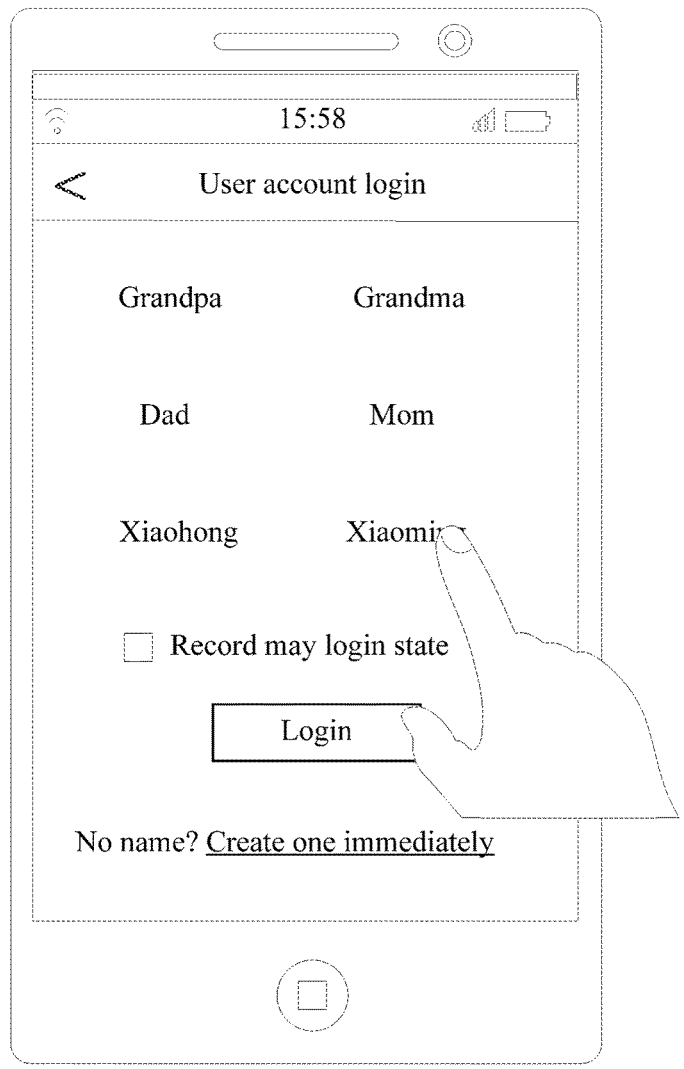
FIG. 15H is a schematic diagram of an interface of login information of a user account according to yet another embodiment of the present disclosure.

In a fifth possible implementation, the foregoing step 1301, step 1302, and step 1304 can be replaced for implementation into step 1301*e*, step 1302*e*, and step 1304*e*, as shown in FIG. 15G:

Step 1301*e*: Receive a fifth creation instruction of a user account.

Step 1302*e*: Create the user account according to the fifth creation instruction, the fifth creation instruction being an instruction used to create a user account having a corresponding name, and the user account including the name.

After receiving a fifth creation instruction, a health index measurement device obtains a name of a user account carried in the fifth creation instruction, and creates the corresponding user account for a user according to the obtained name.

In an optional embodiment, the health index measurement device is a health index measurement device suitable for a family, and at least two preset user accounts are provided in the health index measurement device. Each preset user account corresponds to a name of a preset family role, for example, a name of grandpa, grandma, dad, mom, son, daughter, grandfather, grandmother, default user 11, or default user 12. The preset user account is a user account that is provided by the health index measurement device in default, and does not need to be created by the user himself/herself, and the user can directly use the preset user account after switch-on.

Optionally, the preset user account corresponds to default user information. The user can modify the user information by himself/herself after using the preset user account. The user information includes information such as: gender, age, body weight, a mobile phone number, and a contact address.

When a family member uses the health index measurement device for the first time, the family member selects a user account from the preset user accounts for use according to a family role that the family member belongs without creating a user account by himself/herself.

Step 1304*e*: Receive a selected name by using a name selection input box, and determine the selected name as login information of the user account.

When needing to log in to the health index measurement device, the user selects an account login interface in the health index measurement device, and a name selection input box appears on the account login interface. That is, a series of names appear on the interface. The user selects a name corresponding to the user in the names that appear, and the health index measurement device determines the selected name as login information of the user account.

Optionally, the name selection input box includes at least two names of preset family roles. The at least two names of preset family roles are names owned by the preset user accounts provided, in default, by the health index measurement device.

For example, names "grandpa", "grandma", "dad", "mom", "Xiaoming", and "Xiaohong" are displayed on the login interface. When Xiaoming needs to measure a health index by using the health index measurement device, he clicks a name displayed in the health index measurement device for login, and only needs to select the name "Xiaoming" corresponding to himself from the displayed six names, as shown in FIG. 5H. For another example, names "grandpa", "grandma", "dad", "mom", "Xiaoming", and "Xiaohong" are displayed on the login interface. When grandpa needs to measure a health index by using the health index measurement device, he only needs to select the name "grandpa" corresponding to himself from the displayed six names.

Based on the above, according to the health index measurement method provided in this embodiment, a health index measurement device creates corresponding user accounts according to different names, and determines a selected name as login information of a user account, so as to avoid operation of inputting complex information when determining a user account number and a password as the login information of the user account, thereby achieving the effect of creating a user account and logging in to the user account more easily.

According to the health index measurement method provided in this embodiment, the health index measurement device provides preset user accounts, and a user directly uses a preset user account according to a family role without creating a user account by himself/herself, so that users with poor operating capacities such as old people and patients can also normally use the health index measurement device.

Figure 16A:
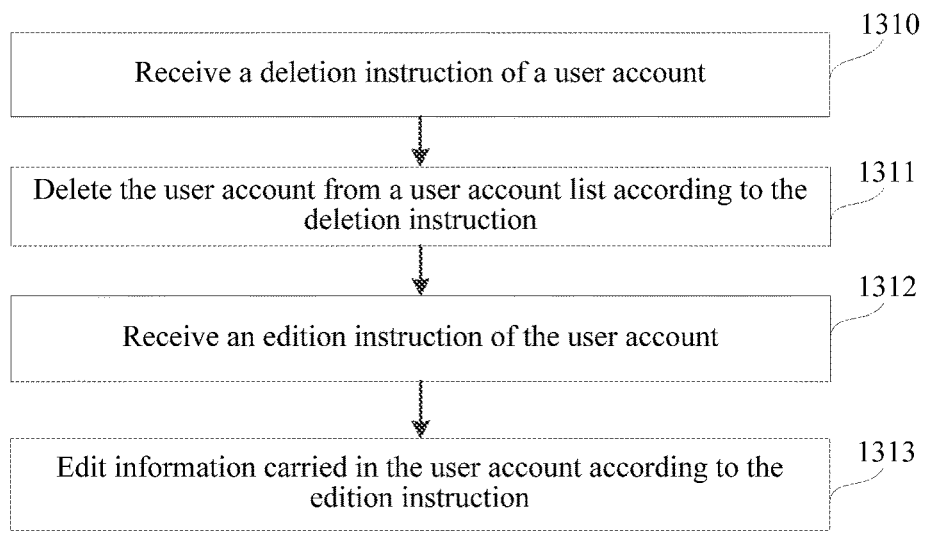
FIG. 16A is a method flowchart of a user account management method according to an embodiment of the present disclosure.

In optional embodiments of the embodiment of FIG. 13A, a user account may further be managed. For example, the user account is deleted or information in the user account is edited. Refer to the following steps shown in FIG. 16A:

Step 1310: Receive a deletion instruction of a user account.

A user may hope to change a user account when using a health index measurement device, or the user needs to delete a user account that is not used in a user account list when the health index measurement device is no longer used. Then the user clicks a user deletion key in the health index measurement device to perform deletion management on user accounts in the user account list.

Correspondingly, the health index measurement device receives a deletion instruction of the user account.

Step 1311: Delete the user account from a user account list according to the deletion instruction.

The health index measurement device deletes the user account from the user account list according to the received deletion instruction of the user account.

Step 1312: Receive an edition instruction of the user account.

The user may hope to change information in his/her user account when using the health index measurement device, and then clicks a user edition key in the health index measurement device to manage the user accounts in the user account list.

Step 1313: Edit information corresponding to the user account according to the edition instruction.

The health index measurement device edits the information corresponding to the user account according to a received edition instruction of the user account.

The information corresponding to the user account includes a name, gender, age, a mobile phone number, an address, and the like corresponding to the user account.

It should be noted that in this embodiment, the sequence between "step 1310 to step 1313" and "step 1301 to step 1309" is not specifically limited, and the sequence between "step 1310 to step 1311" and "step 1312 to step 1313" is either not specifically limited.

Figure 16B:
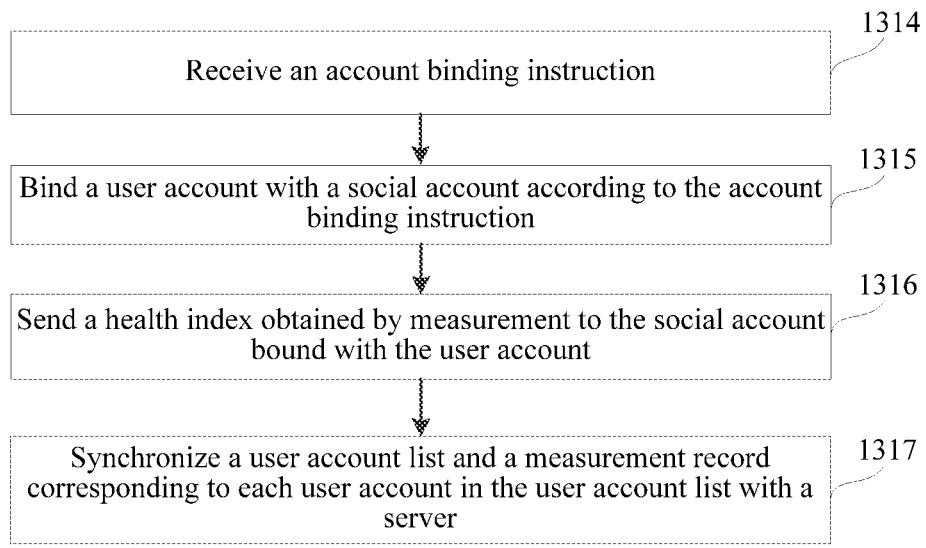
FIG. 16B is a method flowchart of a health index measurement method according to another embodiment of the present disclosure.

In the health index measurement method provided in the embodiment of FIG. 13A, a health index obtained by measurement is stored in a database of a health index measurement device itself. As another implementation, a user account in a health index measurement device may be bound with a social account, and a health index obtained by measurement is synchronized into a server. Refer to the following steps shown in FIG. 16B:

Step 1314: Receive an account binding instruction.

A user hopes to send a health index measured by himself/herself to a social account of himself/herself when using a health index measurement device. Then the user clicks a binding key in the health index measurement device, and binds a user account in the health index measurement device with the social account of himself/herself.

Step 1315: Bind a user account with a social account according to the account binding instruction.

The health index measurement device binds the user account in the health index measurement device with the social account of the user according to a received account binding instruction, so as to send a health index obtained by measurement to the bound social account. The social account may be a social networking account of an instant messaging application.

Step 1316: Send a health index obtained by measurement to the social account bound with the user account.

After measurement of each time, the health index measurement device obtains the social account corresponding to the user account according to the user account, and sends the health index obtained by measurement to the corresponding social account, to monitor a health condition of the user corresponding to the user account at any time.

Schematically, the health index measurement device is a blood glucose meter, and pre-binds a user account "grandpa" with a social account "123455" of a grandson. After blood glucose measurement of the user account "grandpa" is performed, the blood glucose meter sends a blood glucose measurement result to the social account "123455" of the grandson in a form of an instant messaging message, a web page message and/or an audio/video message. The message contains the health index measurement result and corresponding user account (e.g., grandpa).

Step 1317: Synchronize a user account list and a measurement record corresponding to each user account in the user account list with a server.

The health index measurement device may further be connected to the server, and stores a user account list in the health index measurement device and a measurement record corresponding to each user account in the user account list into the server, to implement storage synchronous with the server.

Optionally, the health index measurement device performs synchronization with the server at preset time intervals. Optionally, the health index measurement device performs synchronization with the server after measurement of each time.

Based on the above, a health index measurement device can send a health index obtained by measurement to a bound social account, so that relatives or friends of a user can also automatically learn the health index of the current user in time, so as to urge or remind the user to frequently perform measurement.

It should be noted that in this embodiment, the sequence between step 1314 to step 1317 and step 1301 to step 1313 is not specifically limited.

Apparatus embodiments of the present disclosure are described below. Refer to the foregoing method embodiments having one-to-one correspondence to the apparatus embodiments for details that are not described in detail in the apparatus embodiments.

Figure 17:
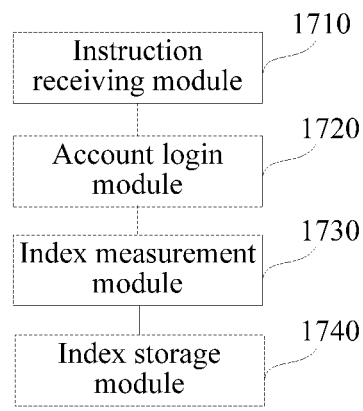
FIG. 17 is a structural block diagram of a health index measurement apparatus according to an embodiment of the present disclosure.

Referring to FIG. 17, FIG. 17 is a structural block diagram of a health index measurement apparatus according to an embodiment of the present disclosure. The health index measurement apparatus provided in this embodiment may be implemented as all or a part of a health index measurement device by software, hardware, or a combination thereof. The apparatus includes: an instruction receiving module 1710, configured to receive login information of a user account, the user account being any user account in a user account list, the user account list including at least two user accounts, and the user account list being stored in a health index measurement device; an account login module 1720, configured to log in to the user account according to the login information; an index measurement module 1730, configured to measure a health index of a user corresponding to the user account; and an index storage module 1740, configured to store the health index obtained by measurement into a measurement record corresponding to the user account.

Figure 18:
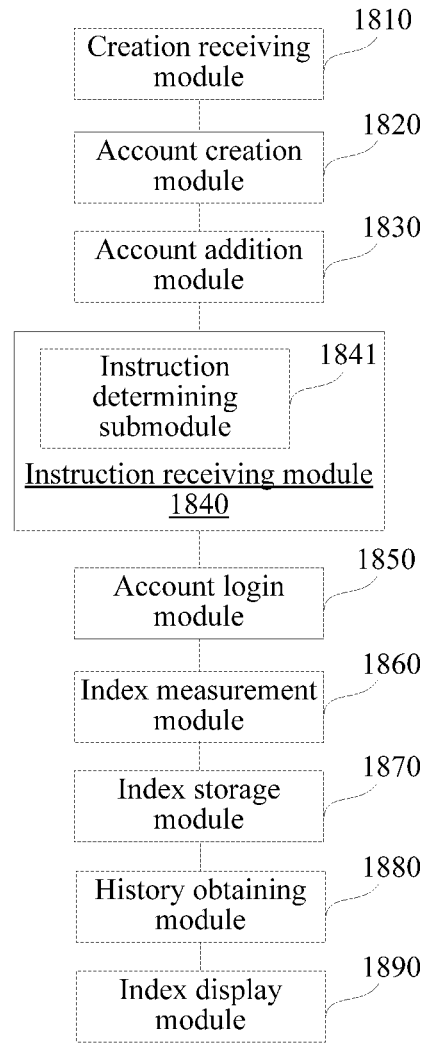
FIG. 18 is a structural block diagram of a health index measurement apparatus according to another embodiment of the present disclosure.

Referring to FIG. 18, FIG. 18 is a structural block diagram of a health index measurement apparatus according to another embodiment of the present disclosure. The health index measurement apparatus provided in this embodiment may be implemented as all or a part of a health index measurement device by software, hardware, or a combination thereof. The apparatus includes program modules stored in a memory and to be executed by a processor, including: a creation receiving module 1810, an account creation module 1820, an account addition module 1830, an instruction receiving module 1840, an account login module 1850, an index measurement module 1860, an index storage module 1870, a history obtaining module 1880, and an index display module 1890.

The creation receiving module 1810 is configured to receive a creation instruction of a user account.

The account creation module 1820 is configured to create the user account according to the creation instruction.

The account addition module 1830 is configured to add the user account into a user account list.

The instruction receiving module 1840 is configured to receive login information of the user account, the user account being any user account in the user account list, the user account list including at least two user accounts, and the user account list being stored in a health index measurement device.

Optionally, the instruction receiving module 1840 may include the following submodule: an instruction determining submodule 1841, configured to receive a user account number and a password input in a login information input box, and determine the user account number and the password as the login information of the user account.

Optionally, the instruction determining submodule 1841 is further configured to receive a selected portrait icon by using a portrait icon selection input box, and determine the selected portrait icon as the login information of the user account.

Optionally, the instruction determining submodule 1841 is further configured to obtain an image collected by a front-facing camera, and determine a human face in the image as the login information of the user account.

Optionally, the instruction determining submodule 1841 is further configured to obtain a fingerprint collected by a fingerprint recognition component, and determine the fingerprint as the login information of the user account.

Optionally, the instruction determining submodule 1841 is further configured to obtain voice information collected by a voice component, and determine the voice information as the login information of the user account.

Optionally, the instruction determining submodule 1841 is further configured to receive a selected name by using a name selection input box, and determine the selected name as the login information of the user account.

The account login module 1850 is configured to log in to the user account according to the login information.

The index measurement module 1860 is configured to measure a health index of a user corresponding to the user account.

The index storage module 1870 is configured to store the health index obtained by measurement into a measurement record corresponding to the user account.

The history obtaining module 1880 is configured to obtain historical health indexes corresponding to the user account from the measurement record, the historical health indexes being health indexes obtained by measurement before the measurement of this time.

The index display module 1890 is configured to display the historical health indexes and the health index that is obtained by the measurement of this time.

Figure 19:
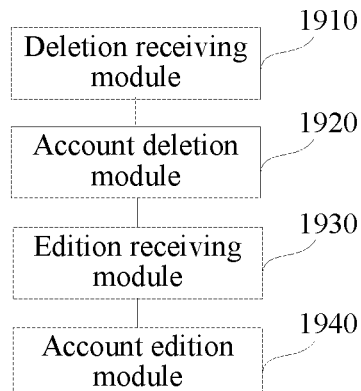
FIG. 19 is a structural block diagram of user account management according to an embodiment of the present disclosure.

As an implementable manner, as shown in FIG. 19, the health index measurement apparatus shown in the embodiment of FIG. 18 may further include the following modules: a deletion receiving module 1910, configured to receive a deletion instruction of the user account; an account deletion module 1920, configured to delete the user account from the user account list according to the deletion instruction; an edition receiving module 1930, configured to receive an edition instruction of the user account; and an account edition module 1940, configured to edit information corresponding to the user account according to the edition instruction.

Figure 20:
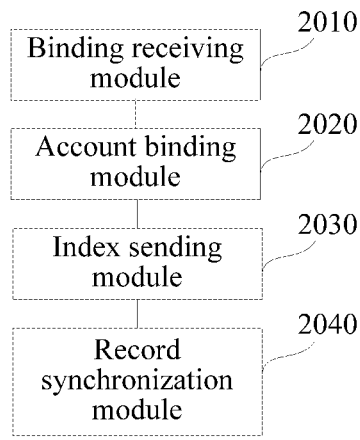
FIG. 20 is a structural block diagram of a health index measurement apparatus according to another embodiment of the present disclosure.

As another implementable manner, as shown in FIG. 20, the health index measurement apparatus shown in the embodiment of FIG. 18 may further include the following modules: a binding receiving module 2010, configured to receive an account binding instruction; an account binding module 2020, configured to bind the user account with a social account according to the account binding instruction; an index sending module 2030, configured to send the health index obtained by the measurement to the corresponding social account; and a record synchronization module 2040: configured to synchronize a user account list and a measurement record corresponding to each user account in the user account list with a server.

Figure 21:
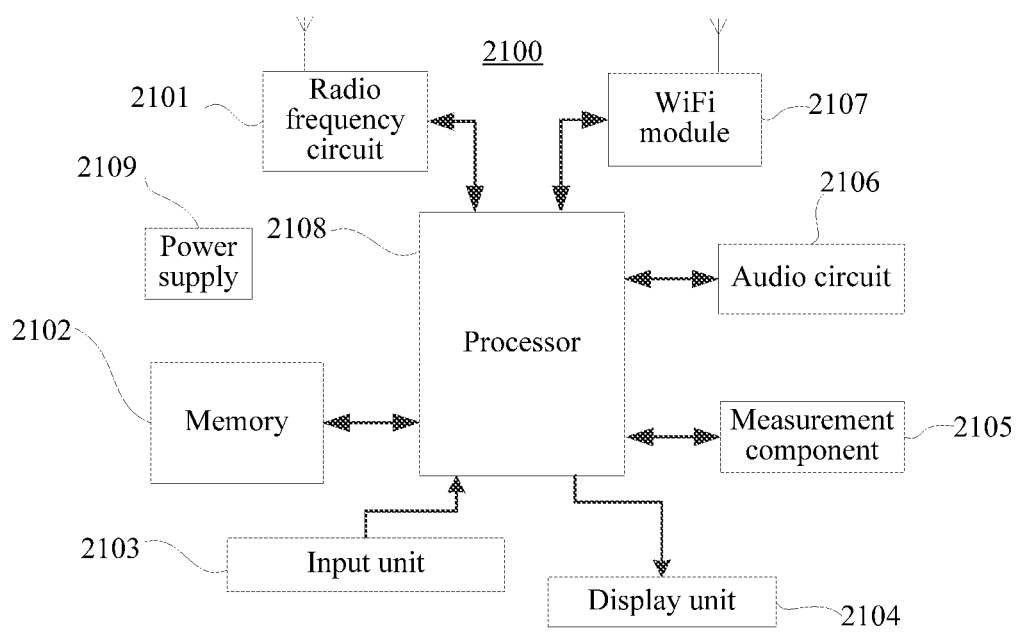
FIG. 21 is a schematic structural diagram of a health index measurement device according to an embodiment of the present disclosure.

Referring to FIG. 21, FIG. 21 is a block diagram of a health index measurement device 2100 according to an embodiment of the present disclosure. The health index measurement device may include components such as a radio frequency (RF) circuit 2101, a memory 2102 including one or more computer readable storage media, an input unit 2103, a display unit 2104, a measurement component 2105, an audio circuit 2106, a Wireless Fidelity (WiFi) module 2107, a processor 2108 including one or more processing cores, and a power supply 2109. A person skilled in the art may understand that the structure of the health index measurement device shown in FIG. 21 does not constitute a limitation to the health index measurement device, and the health index measurement device may include more components or fewer components than those shown in the figure, or some components may be combined, or a different component deployment may be used. The foregoing RF circuit and/or WiFi module may also be generally referred to as communications components.

The RF circuit 2101 may be configured to receive and send signals during an information receiving and sending process or a call process. Particularly, the RF circuit 2101 receives downlink information from a base station, then delivers the downlink information to one or more processors 2108 for processing, and sends related uplink data to the base station. Generally, the RF circuit 2101 includes, but is not limited to, an antenna, at least one amplifier, a tuner, one or more oscillators, a subscriber identity module (SIM) card, a transceiver, a coupler, a low noise amplifier (LNA), and a duplexer. In addition, the RF circuit 2101 may also communicate with a network and another device by wireless communication. The wireless communication may use any communications standard or protocol, which includes, but is not limited to, Global System for Mobile communications (GSM), General Packet Radio Service (GPRS), Code Division Multiple Access (CDMA), Wideband Code Division Multiple Access (WCDMA), Long Term Evolution (LTE), email, Short Messaging Service (SMS), and the like.

The memory 2102 may be configured to store a software program and module. The processor 2108 runs the software program and module stored in the memory 2102, to implement various functional applications and data processing. The memory 2102 may mainly include a program storage area and a data storage area. The program storage area may store an operating system, an application program required by at least one function (such as a sound playback function and an image display function), and the like. The data storage area may store data (such as audio data and an address book) created according to use of the health index measurement device, and the like. In addition, the memory 2102 may include a high speed random access memory, and may also include a non-volatile memory, such as at least one magnetic disk storage device, a flash memory, or another volatile solid-state storage device. Correspondingly, the memory 2102 may further include a memory controller, so as to facilitate access of the processor 2108 and the input unit 2103 to the memory 2102.

The input unit 2103 may be configured to receive input digit or character information, and generate a keyboard, mouse, joystick, optical, or track ball signal input related to the user setting and function control. Specifically, in a specific embodiment, the input unit 2103 may include a touch-sensitive surface and another input device. The touch-sensitive surface, which may also be referred to as a touch-screen or a touch panel, may collect a touch operation of a user on or near the touch-sensitive surface (such as an operation of a user on or near the touch-sensitive surface by using any suitable object or accessory, such as a finger or a stylus), and drive a corresponding connection apparatus according to a preset program. Optionally, the touch-sensitive surface may include two parts: a touch detection apparatus and a touch controller. The touch detection apparatus detects a touch position of the user, detects a signal generated by the touch operation, and transfers the signal to the touch controller. The touch controller receives the touch signal from the touch detection apparatus, converts the touch signal into touch point coordinates, and sends the touch point coordinates to the processor 2108. Moreover, the touch controller can receive and execute a command sent from the processor 2108. In addition, the touch-sensitive surface may be may be a resistive, capacitive, infrared, or surface sound wave type touch-sensitive surface. In addition to the touch-sensitive surface, the input unit 2103 may further include other input device. Specifically, the other input device may include, but is not limited to, one or more of a physical keyboard, a functional key (such as a volume control key or a switch key), a track ball, a mouse, and a joystick.

The display unit 2104 may be configured to display information input by the user or information provided for the user, and various graphical user interfaces of the health index measurement device. The graphical user interfaces may be formed by a graph, a text, an icon, a video, or any combination thereof. The display unit 2104 may include a display panel. Optionally, the display panel may be configured by using a liquid crystal display (LCD), an organic light-emitting diode (OLED), or the like. Further, the touch-sensitive surface may cover the display panel. After detecting a touch operation on or near the touch-sensitive surface, the touch-sensitive surface transfers the touch operation to the processor 2108, so as to determine the type of the touch event. Then, the processor 2108 provides a corresponding visual output on the display panel according to the type of the touch event. Although, in FIG. 21, the touch-sensitive surface and the display panel are used as two separate parts to implement input and output functions, in some embodiments, the touch-sensitive surface and the display panel may be integrated to implement the input and output functions.

The health index measurement device may further include a measurement component 2105, which is a component configured to convert information on a test strip into an electric signal. For example, the measurement component 2105 is a component that converts blood glucose information on a blood glucose test strip contaminated with blood into an electric signal. In different health index measurement devices, functions of the measurement component 2105 are different.

Optionally, the health index measurement device may further include at least one sensor such as an optical sensor, a motion sensor, and other sensors. Specifically, the optical sensor may include an ambient light sensor and a proximity sensor. The ambient light sensor may adjust luminance of the display panel according to brightness of the ambient light. The proximity sensor may switch off the display panel and/or backlight when the health index measurement device is moved to the ear. As one type of motion sensor, a gravity acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, an infrared sensor, and a fingerprint collection component, which may be configured in the health index measurement device, are not further described herein.

The audio circuit 2106, a speaker, and a microphone may provide audio interfaces between the user and the health index measurement device. The audio circuit 2106 may convert received audio data into an electric signal and transmit the electric signal to the speaker. The speaker converts the electric signal into a sound signal for output. On the other hand, the microphone converts a collected sound signal into an electric signal. The audio circuit 2106 receives the electric signal and converts the electric signal into audio data, and outputs the audio data to the processor 2108 for processing. Then, the processor 2108 sends the audio data to, for example, another health index measurement device by using the RF circuit 2101, or outputs the audio data to the memory 2102 for further processing. The audio circuit 2106 may further include an earplug jack, so as to provide communication between a peripheral earphone and the health index measurement device. The audio circuit 2106 and the microphone may also be referred to as voice components.

WiFi is a short distance wireless transmission technology. The health index measurement device may help, by using the WiFi module 2107, the user to receive and send emails, browse a web page, access streaming media, and so on, which provides wireless broadband Internet access for the user. Although FIG. 21 shows the WiFi module 2107, it may be understood that the WiFi module 2107 is not a necessary component of the health index measurement device, and when required, the health index measurement device may be omitted as long as the scope of the essence of the present disclosure is not changed.

The processor 2108 is the control center of the health index measurement device, and is connected to various parts of the mobile phone by using various interfaces and lines. By running or executing the software program and/or module stored in the memory 2102, and invoking data stored in the memory 2102, the processor 2108 performs various functions and data processing of the health index measurement device, thereby performing overall monitoring on the mobile phone. Optionally, the processor 2108 may include one or more processing cores. Preferably, the processor 2108 may integrate an application processor and a modem. The application processor mainly processes an operating system, a user interface, an application program, and the like. The modem mainly processes wireless communication. It may be understood that the foregoing modem may either not be integrated into the processor 2108.

The health index measurement device further includes the power supply 2109 (such as a battery) for supplying power to the components. Preferably, the power supply may be logically connected to the processor 2108 by using a power management system, thereby implementing functions such as charging, discharging and power consumption management by using the power management system. The power supply 2109 may further include one or more of a direct current or alternating current power supply, a re-charging system, a power failure detection circuit, a power supply converter or inverter, a power supply state indicator, and any other components.

Although not shown in the figure, the health index measurement device may further include a camera, a Bluetooth module, and the like, which are not further described herein. Specifically, in this embodiment, the processor 2108 in the health index measurement device runs one or more program instructions stored in the memory 2102, so as to implement health index measurement methods according to the foregoing various method embodiments.

Beneficial effects brought by the technical solutions provided in the embodiments of the present invention are as follows: a user account mechanism is provided in a health index measurement device, so that the problem that a user has to manually record a health index onto a recording card of the corresponding user after measurement of each time is completed, resulting in easy occurrence of obfuscated data is resolved, and when multiple family members use a same health index measurement device, the health index measurement device automatically stores health indexes of the family members into corresponding measurement records, thereby implementing automatic aggregation management on health indexes of the family members.

A person of ordinary skill in the art may understand that all or some of the steps in the health index measurement methods in the foregoing embodiments may be performed by a program instructing relevant hardware. The program may be stored in a computer readable storage medium. The storage medium may be a read only memory (ROM), a random access memory (RAM), a magnetic disk, an optical disc, or the like.

It should be noted that the above functional modules are only described for exemplary purposes when the health index measurement apparatus provided by the foregoing embodiments measures a health index. In actual applications, the functions may be allocated to different functional modules according to specific needs, which means that the internal structure of the device is divided to different functional modules to complete all or some of the above described functions. In addition, the health index measurement apparatus provided by the foregoing embodiments is based on the same concept as the health index measurement method in the foregoing embodiments. For the specific implementation process, refer to the method embodiments, and the details are not described herein again.

Referring to FIG. 22, FIG. 22 is a schematic diagram of an implementation scenario involved in test-paper-based measurement methods according to various embodiments of the present disclosure. As shown in FIG. 22, the implementation scenario includes a test strip analysis device 2220 and a test strip bottle 2240 that is configured to accommodate/store test strips. The test strip analysis device 2220, as used herein, may be referred as health management apparatus.

A port 2220a for insertion of a test strip is disposed in the test strip analysis device 2220. A test strip 2240a matching the test strip analysis device 2220 for use is disposed in the test strip bottle 2240. The test strip analysis device 2220 may be a blood glucose meter, and correspondingly, the test strip 2240a may be a blood glucose test strip. Certainly, during actual implementation, the test strip analysis device 2220 may alternatively be another device such as a starch monitoring device, a phenolphthalein monitoring device, or a temperature monitoring device. The corresponding test strip 2240a is a test strip corresponding to the other monitoring device. This embodiment does not make a limitation to this.

A surface of the test strip bottle 2240 is provided with a calibration information identifier 2240b configured to represent a calibration information of the test strip in the test strip bottle 2240. The calibration information identifier 2240b may be at least one of a color, a number, a pattern, or a graphic code. For example, if the calibration information identifier 2240b is a color, red may be used to represent being higher than a normal level by 2% to 5%, and yellow may be used to represent being lower than the normal level by 5% to 7%. For another example, if the calibration information identifier 2240b is a number, 01 represents compensation information of a first batch of produced test strips, and 02 represents compensation information of a second batch of produced test strips.

Optionally, the implementation scenario may further include a server 2260. The test strip analysis device 2220 is connected to the server 2260 by using a network. The network may be a Wireless-Fidelity (WiFi), 2-Generation wireless telephone technology (2G), 3G, or 4G network.

Optionally, the foregoing wireless network or wired network uses a standard communications technology and/or protocol. The network is usually the Internet, or may be any network, including but not limited to a local area network (LAN), a metropolitan area network (MAN), a wide area network (WAN), or any combination of a mobile, wired, or wireless network, a private network, or a virtual private network (VPN). In some embodiments, technologies and/or formats including Hypertext Markup Language (HTML), Extensible Markup Language (XML), and the like are used to represent data exchanged by using the network. In addition, conventional encryption technologies such as Secure Sockets Layer (SSL), Transport Layer Security (TLS), VPN, and Internet Protocol Security (IPsec) are used to encrypt all or some links.

Figure 23:
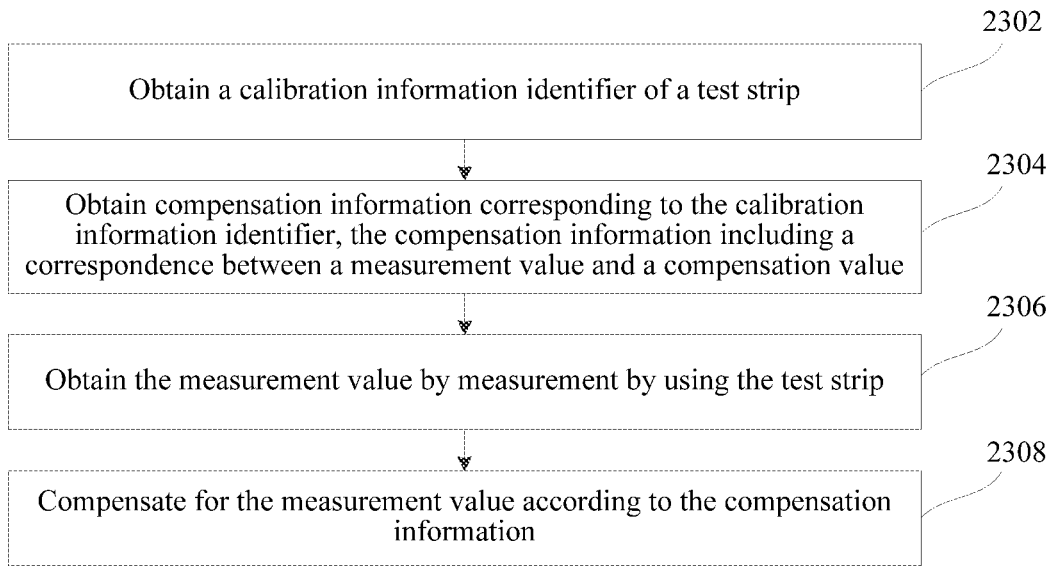
FIG. 23 is a flowchart of a test-paper-based measurement method according to an embodiment of the present disclosure.

Referring to FIG. 23, FIG. 23 is a flowchart of a test-paper-based measurement method according to an embodiment of the present disclosure. This embodiment is described by using that the measurement method is used in the test strip analysis device 2220 shown in FIG. 22 as an example. As shown in FIG. 23, the test-paper-based measurement method may include the following steps: step 2302: Obtain a calibration information identifier of a test strip; step 2304: Obtain compensation information corresponding to the calibration information identifier, the compensation information including a correspondence between a measurement value and a compensation value; step 2306: Obtain the measurement value by measurement by using the test strip; and step 2308: Compensate for the measurement value according to the compensation information. The physiological data may be obtained and recorded based on the compensated value.

Based on the above, according to the test-paper-based measurement method provided in this embodiment, corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

It should be supplemented that because compensation information may be locally stored, or may be stored in a server, step 2304 may include the following two possible implementations.

First, if the compensation information is locally stored, the compensation information corresponding to the calibration information identifier is queried according to the correspondence between the calibration information identifier and the compensation information.

Second, if the compensation information is stored in the server, an information obtaining request is sent to the server, and compensation information fed back by the server is received. The compensation information is information queried and fed back by the server according to the correspondence between the calibration information identifier and the compensation information.

Therefore, the foregoing two cases will be introduced in detail below in two different embodiments.

Figure 24A:
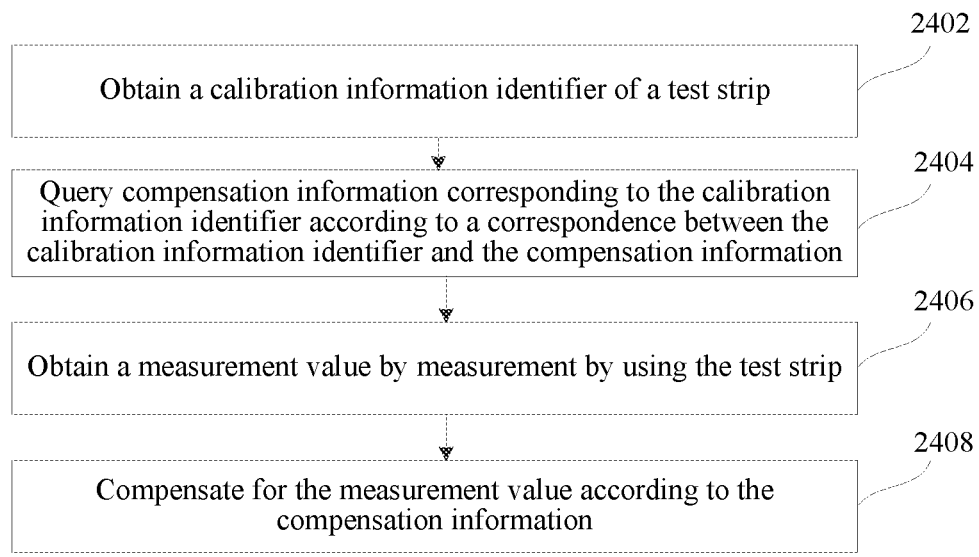
FIG. 24A is a flowchart of a test-paper-based measurement method according to another embodiment of the present disclosure.

Referring to FIG. 24A, FIG. 24A is a flowchart of a test-paper-based measurement method according to another embodiment of the present disclosure. This embodiment is described by using that the measurement method is used in the test strip analysis device 2220 shown in FIG. 22, and compensation information is obtained by using the foregoing first obtaining method as an example. As shown in FIG. 24A, the test-paper-based measurement method may include the following steps:

Step 2402: Obtain a calibration information identifier of a test strip.

This embodiment is described by using that the test strip analysis device is a blood glucose meter, and a test strip is a blood glucose test strip as an example. Moreover, a calibration information identifier in this embodiment is used to identify an error range of a blood glucose value obtained by measurement by using the blood glucose test strip. Each calibration information identifier corresponds to a group of compensation information. Optionally, the compensation information includes a correspondence between a measurement value and a compensation value. For example, when the measurement value is 2220, the compensation value is +2. For another example, when the measurement value is 2240, the compensation value is +3.

The calibration information identifier may be at least one of a color, a number, a pattern, or a graphic code. For example, if the calibration information identifier is a color, red may be used to represent being higher than a normal level by 2% to 5%, and yellow may be used to represent being lower than the normal level by 5% to 7%.

Optionally, step 2402 includes any one of the following three implementations. A graphical interface may be presented to provide multiple options for entering the calibration information identifier.

First, a test strip analysis device receives a setting instruction for setting the calibration information identifier and obtains the calibration information identifier set by the setting instruction, the calibration information identifier being an identifier carried in the test strip and/or a package of the test strip.

Figure 24B:
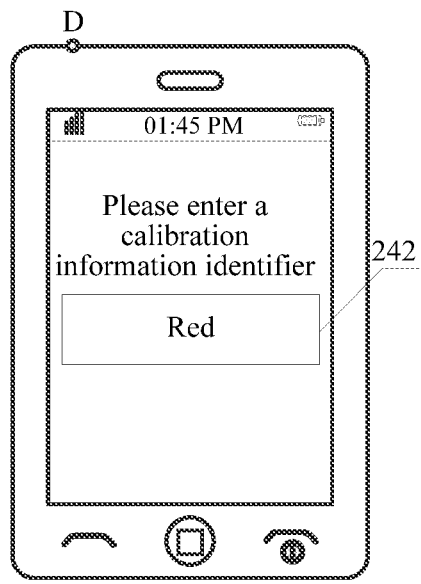
FIG. 24B is a schematic diagram of an interface when a calibration information identifier of a test strip is obtained according to an embodiment of the present disclosure.

Optionally, the test strip analysis device displays an input box, and receives an input instruction of a user for inputting the calibration information identifier in the input box. Description is made by using that the calibration information identifier is a color, and the color is disposed in a test strip bottle of the blood glucose test strip as an example. Referring to FIG. 24B, after the user starts the blood glucose meter, the blood glucose meter may display an interface shown in FIG. 24B. The interface includes the input box 242 for inputting a color.

After viewing the color in the test strip bottle for accommodating the blood glucose test strip, the user enters the corresponding color in the input box 242. Correspondingly, the blood glucose meter may receive an input instruction of the user for inputting a color.

Alternatively, the test strip analysis device displays an interface including various candidate calibration information identifiers, and receives a selection instruction for selecting one calibration information identifier among the candidate calibration information identifiers. The interface is a user interface (UI).

Figure 24C:
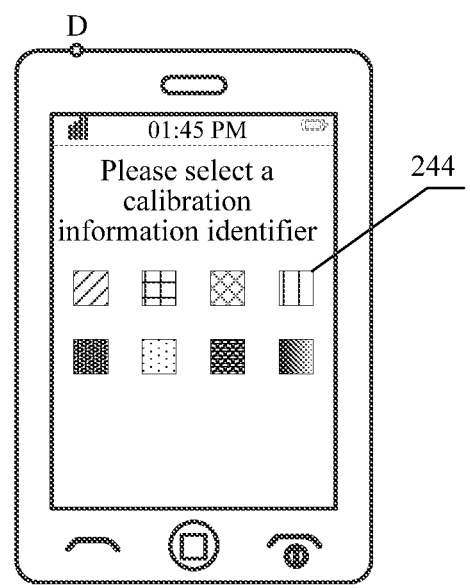
FIG. 24C is a schematic diagram of another interface when the calibration information identifier of the test strip is obtained according to an embodiment of the present disclosure.
Figure 24D:
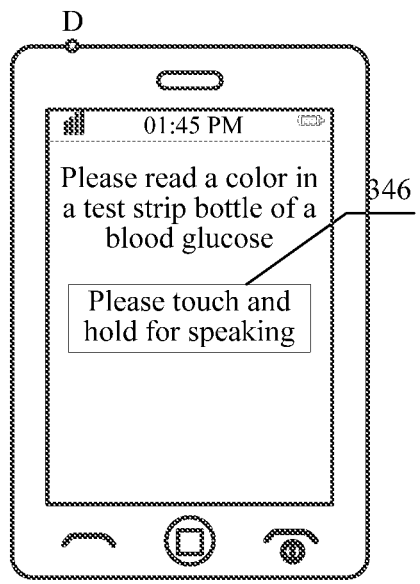
FIG. 24D is a schematic diagram of still another interface when the calibration information identifier of the test strip is obtained according to an embodiment of the present disclosure.

Referring to FIG. 24C, various candidate colors are displayed in FIG. 24C (In FIG. 24C, description is made by using that different patterns represent different colors as an example). For example, an identifier 244 in FIG. 24C represents a color candidate. In this way, after the blood glucose meter is switched on, a user can select, on the interface, a color in a test strip bottle of the blood glucose test strip. Correspondingly, the blood glucose meter receives a selection instruction of the user for selecting a candidate color.

Second, a voice instruction is received, and the calibration information identifier carried in the voice instruction is extracted, the calibration information identifier being an identifier carried in the test strip and/or a package of the test strip.

A user may notify the blood glucose meter of the calibration information identifier of the blood glucose test strip in a manner of a voice. For example, after the blood glucose meter is started, the blood glucose meter displays an interface shown in FIG. 24D. According to a prompt "please read the color in the test strip bottle of the blood glucose test strip" on the interface, the user reads a color "red" corresponding to the calibration information identifier after touching and holding a control 246. After receiving the voice instruction of the user, the blood glucose meter performs voice recognition and voice analysis on the voice instruction, and extracts the color, corresponding to the blood glucose test strip, carried in the voice instruction.

Third, a graphic code carried in the test strip and/or a package of the test strip is scanned, and the calibration information identifier carried in the graphic code is obtained.

If a graphic code is disposed in the blood glucose test strip or a test strip bottle, after the blood glucose meter is started, a user may further scan the graphic code carried in the blood glucose test strip and/or a package of the blood glucose test strip by using the blood glucose meter. The graphic code may be a barcode or a two-dimensional code, and carries the calibration information identifier of the blood glucose test strip.

Step 2404: Query compensation information corresponding to the calibration information identifier according to a correspondence between the calibration information identifier and the compensation information.

A correspondence between the calibration information identifier and compensation information may be locally stored in the blood glucose meter. The correspondence may be burned into the blood glucose meter when the blood glucose meter is at delivery, or may be pre-downloaded from a server by the blood glucose meter.

After obtaining the calibration information identifier, the blood glucose meter queries the compensation information corresponding to the obtained calibration information identifier according to the locally stored correspondence.

For example, referring to the following table, which shows a possible correspondence stored in the blood glucose meter. As shown in the following table, when a color obtained by the blood glucose meter is red, the blood glucose meter can obtain corresponding compensation information according to a correspondence in the following table.

| Calibration information identifier | Compensation information |
| --- | --- |
| Red (representing being higher than a normal level by 2% to 5%) | Measurement value 70-79 compensation value −9<br>Measurement value 80-89 compensation value −8<br>Measurement value 90-99 compensation value −7<br>. . . |
| Yellow (representing being lower than the normal level by 5% to 7%) | Measurement value 70-79 compensation value +10<br>Measurement value 80-89 compensation value +9<br>Measurement value 90-99 compensation value +8<br>. . . |

Step 2406: Obtain a measurement value by measurement by using the test strip.

When needing to measure his/her blood glucose, the user may insert a test strip contaminated with a test liquid into the blood glucose meter. Optionally, the test liquid is blood. A corresponding measurement value is obtained by measurement by using the blood glucose meter.

Step 2408: Compensate for the measurement value according to the compensation information.

After obtaining the measurement value by measurement, the blood glucose meter can query the obtained compensation information, so as to obtain a compensation value corresponding to the measurement value, and compensate for the measurement value according to the obtained compensation value.

For example, if the measurement value is 87, after querying the compensation information, the blood glucose meter can determine that the compensation value is −8, and in this case, a blood glucose value finally determined by the blood glucose meter is 87−8=79.

Based on the above, according to the test-paper-based measurement method provided in this embodiment, corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

Compensation information corresponding to each calibration information identifier is locally stored, so that when getting offline, a blood glucose meter can also compensate, according to the locally stored compensation information, for a blood glucose value obtained by measurement, thereby ensuring the accuracy of the measurement.

It should further be noted that a large quantity of users of blood glucose meters are elderly users, and the elderly users have difficulty in completing relatively complex operations when using a blood glucose meter. Therefore, for the elderly users, the operating difficulty in operating the blood glucose meter can be effectively reduced by using a color, a pattern, a number, or a graphic code as a calibration information identifier and by using a manner of inputting a voice, selecting a candidate calibration information identifier, or scanning a graphic code as an input mode, thereby avoiding the problem that the elderly users cannot smoothly complete the test strip measurement process due to the excessively high operating difficulty.

Figure 25A:
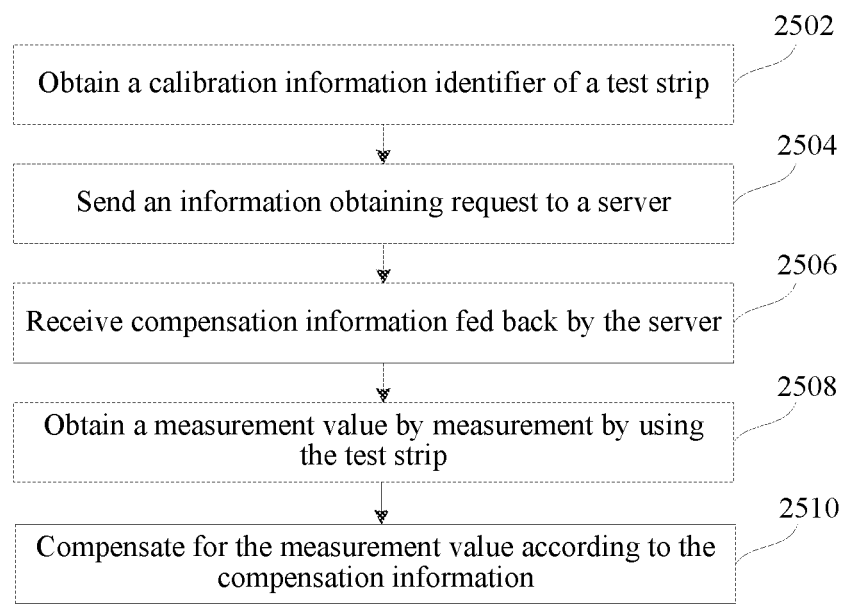
FIG. 25A is a flowchart of a test-paper-based measurement method according to still another embodiment of the present disclosure.

Referring to FIG. 25A, FIG. 25A is a flowchart of a test-paper-based measurement method according to still another embodiment of the present disclosure. This embodiment is described by using that the measurement method is used in the test strip analysis device shown in FIG. 22, and compensation information is obtained by using the foregoing second obtaining method as an example. As shown in FIG. 25A, the test-paper-based measurement method may include the following steps:

Step 2502: Obtain a calibration information identifier of a test strip.

This step is similar to step 2402 in the foregoing embodiment, and details are not described herein again.

Step 2504: Send an information obtaining request to a server.

A blood glucose meter can send an information obtaining request to a server, the information obtaining request including a calibration information identifier of a blood glucose test strip.

After receiving the information obtaining request, the server queries, according to a stored correspondence between the calibration information identifier and the compensation information, compensation information corresponding to the calibration information identifier carried in the information obtaining request, and feeds back the found compensation information to the blood glucose meter.

Step 2506: Receive compensation information fed back by the server.

Optionally, after receiving the compensation information fed back by the server, the blood glucose meter can store the received compensation information and a corresponding color in a corresponding manner.

Step 2508: Obtain a measurement value by measurement by using the test strip.

Step 2510: Compensate, according to the compensation information, for the measurement value obtained by the measurement.

Step 2508 and step 2510 are similar to step 2406 and step 2408 in the foregoing embodiment, and details are not described herein again.

Figure 25B:
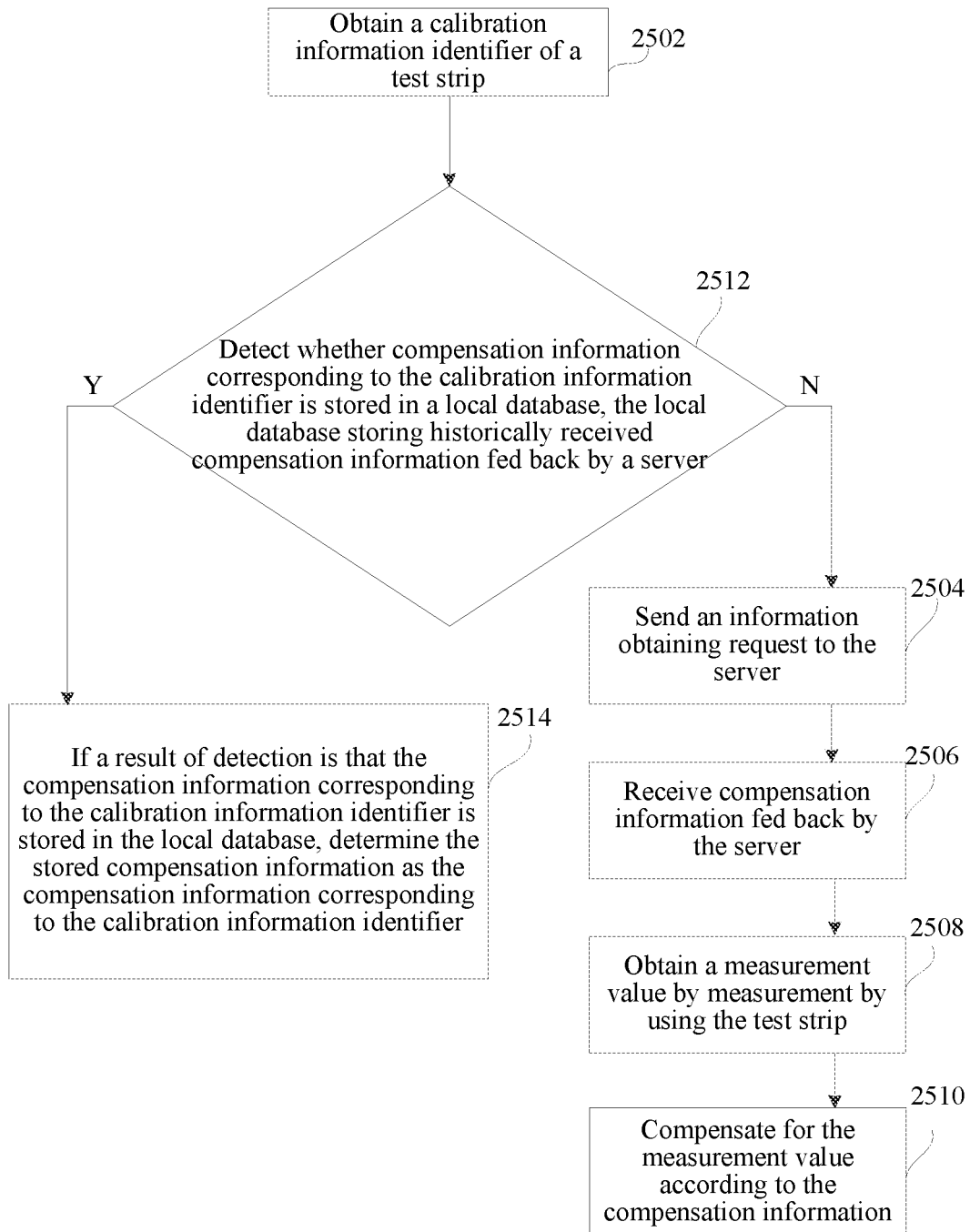
FIG. 25B is a flowchart of the test-paper-based measurement method according to the still another embodiment of the present disclosure.

It should be supplemented that referring to FIG. 25B, before step 2504, the following steps may further be performed.

Step 2512: Detect whether compensation information corresponding to the calibration information identifier is stored in a local database, the local database storing historically received compensation information fed back by a server.

Step 2514: If a result of detection is that the compensation information corresponding to the calibration information identifier is stored in the local database, determine the stored compensation information as the compensation information corresponding to the calibration information identifier.

However, if the result of the detection is that the compensation information corresponding to the calibration information identifier is not stored in the local database, step 2504 is performed.

Based on the above, according to the test-paper-based measurement method provided in this embodiment, corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

In addition, compensation information is stored in a server, so that on one hand, a storage space of a test strip analysis device can be reduced, and on the other hand, a compensation range of the test strip analysis device can be updated in real time according to an error during test strip production, and therefore accurate compensation can also be implemented when a test strip error change is excessively large or data is incorrect due to a use environment.

It should be supplemented that calibration informations of a same test strip may be different when the test strip is used in different regions. Therefore, when designing compensation information, a designer may set different compensation information for a test strip having a same calibration information in a same region in consideration of different regions. In this case, the step of compensating, according to the compensation information, for the measurement value in the foregoing embodiment may include:

First, obtain a region in which the test strip is located.

Description is made still by using that the test strip analysis device is the blood glucose meter, and the test strip is the blood glucose test strip as an example. The blood glucose meter can send a trigger request to the server by using a network, and the server determines, according to the trigger request, a region, to which the network used by the blood glucose meter belongs, determines the region as a current region of the blood glucose meter, and feeds back the determined region to the blood glucose meter.

For example, the blood glucose meter sends the trigger request to the server by using a wired broadband of a city XX, and the server can feed back a region "city XX" to the blood glucose meter.

Second, obtain compensation information corresponding to the region from the obtained compensation information.

Optionally, the compensation information obtained by the blood glucose meter includes compensation information corresponding to each region. After obtaining the region in which the blood glucose meter is located, the blood glucose meter selects compensation information corresponding to the region in which the blood glucose meter is located from the compensation information corresponding to each region.

Third, compensate for the measurement value according to the selected compensation information.

Apparatus embodiments of the present disclosure are described below, and can be used to execute the method embodiments of the present disclosure. Refer to the method embodiments of the present disclosure for details that are not disclosed in the apparatus embodiments of the present disclosure.

Figure 26:
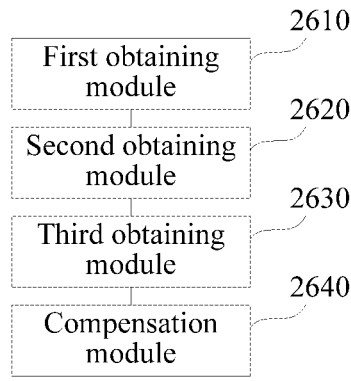
FIG. 26 is a block diagram of a test-paper-based measurement apparatus according to an embodiment of the present disclosure.

Referring to FIG. 26, FIG. 26 is a block diagram of a test-paper-based measurement apparatus according to an embodiment of the present disclosure. The test-paper-based measurement apparatus may include a first obtaining module 2610, a second obtaining module 2620, a third obtaining module 2630, and a compensation module 2640.

The first obtaining module 2610 is configured to obtain a calibration information identifier of a test strip.

The second obtaining module 2620 is configured to obtain compensation information corresponding to the calibration information identifier obtained by the first obtaining module 2610, the compensation information including a correspondence between a measurement value and a compensation value.

The third obtaining module 2630 is configured to obtain the measurement value by measurement by using the test strip.

The compensation module 2640 is configured to compensate, according to the compensation information obtained by the second obtaining module 2620, for the measurement value obtained by the third obtaining module 2630.

Based on the above, according to the test-paper-based measurement apparatus provided in this embodiment, corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

Figure 27:
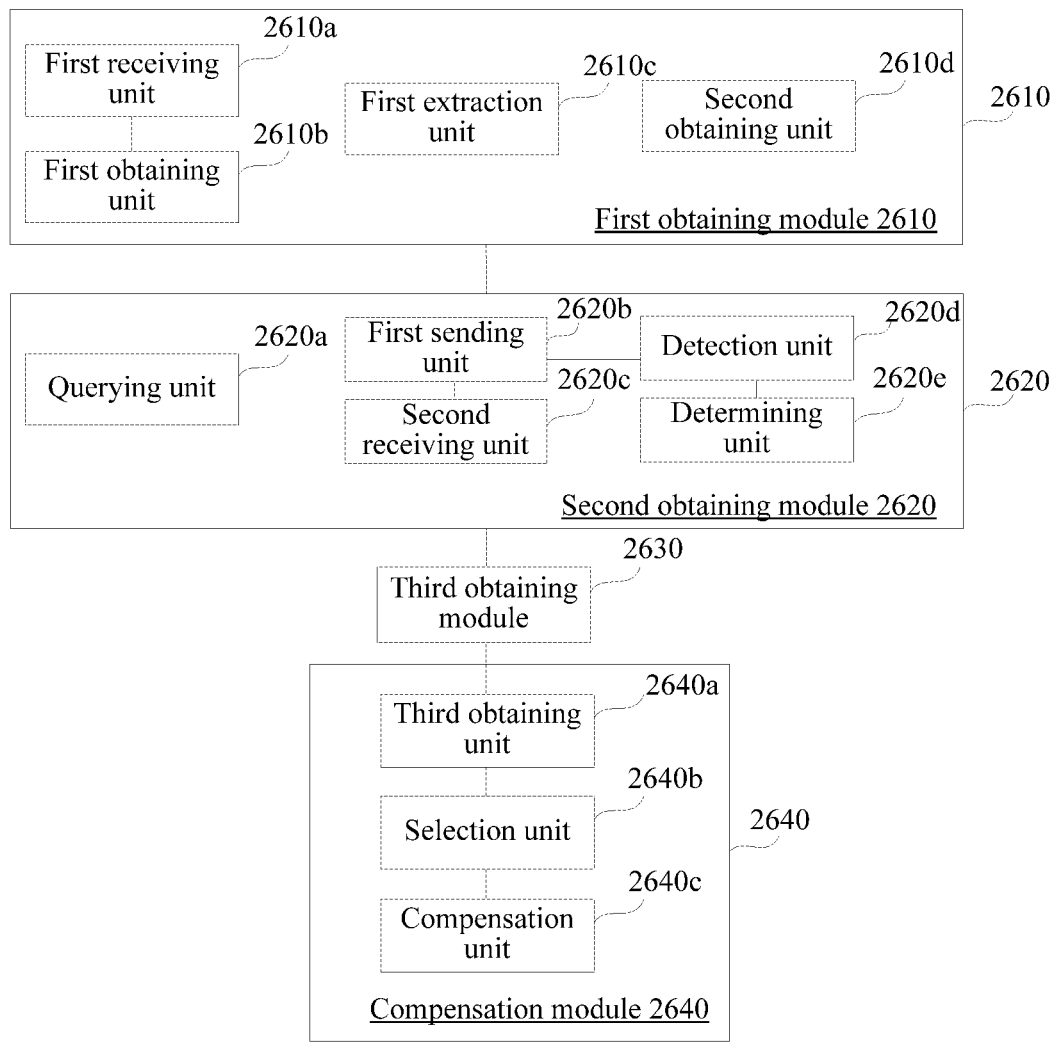
FIG. 27 is a block diagram of a test-paper-based measurement apparatus according to another embodiment of the present disclosure.

Referring to FIG. 27, FIG. 27 is a block diagram of a test-paper-based measurement apparatus according to another embodiment of the present disclosure. The bit rate control apparatus may include a first obtaining module 2610, a second obtaining module 2620, a third obtaining module 2630, and a compensation module 2640.

The first obtaining module 2610 is configured to obtain a calibration information identifier of a test strip.

The second obtaining module 2620 is configured to obtain compensation information corresponding to the calibration information identifier obtained by the first obtaining module 2610, the compensation information including a correspondence between a measurement value and a compensation value.

The third obtaining module 2630 is configured to obtain the measurement value by measurement by using the test strip.

The compensation module 2640 is configured to compensate, according to the compensation information obtained by the second obtaining module 2620, for the measurement value obtained by the third obtaining module 2630.

Optionally, the first obtaining module 2610 includes a first receiving unit 2610*a*, a first obtaining unit 2610*b*, or a first extraction unit 2610*c*, or a second obtaining unit 2610*d*.

The first receiving unit 2610*a* is configured to receive a setting instruction for setting the calibration information identifier. The first obtaining unit 2610*b* is configured to obtain the calibration information identifier set by the setting instruction, the calibration information identifier being an identifier carried in the test strip and/or a package of the test strip.

The first extraction unit 2610*c* is configured to: receive a voice instruction, and extract the calibration information identifier carried in the voice instruction, the calibration information identifier being an identifier carried in the test strip and/or the package of the test strip.

The second obtaining unit 2610*d* is configured to: scan a graphic code carried in the test strip and/or the package of the test strip, and obtain the calibration information identifier carried in the graphic code.

In a possible implementation, the calibration information identifier may be at least one of a color, a number, or a pattern. The first receiving unit 2610*a* is specifically configured to: display an input box, and receive an input instruction for inputting the calibration information identifier in the input box; or the first receiving unit 2610*a* is specifically configured to: display an interface including various candidate calibration information identifiers, and receive a selection instruction for selecting one identifier among the candidate calibration information identifiers.

Optionally, the second obtaining module 2620 may include a querying unit 2620*a*.

The querying unit 2620*a* is configured to query the compensation information corresponding to the calibration information identifier according to a correspondence between the calibration information identifier and the compensation information.

Optionally, the second obtaining module 2620 may further include a first sending unit 2620*b* and a second receiving unit 2620*c*.

The first sending unit 2620*b* is configured to send an information obtaining request to a server.

The second receiving unit 2620*c* is configured to receive the compensation information fed back by the server, the compensation information being information queried and fed back by the server according to the correspondence between the calibration information identifier and the compensation information.

Optionally, the second obtaining module 2620 further includes a detection unit 2620*d* and a determining unit 2620*e*.

The detection unit 2620*d* is configured to detect whether the compensation information corresponding to the calibration information identifier is stored in a local database, the local database storing historically received compensation information fed back by the server.

The determining unit 2620*e* is configured to: if a result of detection by the detection unit is that the compensation information corresponding to the calibration information identifier is stored in the local database, determine the stored compensation information as the compensation information corresponding to the calibration information identifier.

Optionally, the compensation module 2640 may include a third obtaining unit 2640*a*, a selection unit 2640*b*, and a compensation unit 2640*c*.

The third obtaining unit 2640*a* is configured to obtain a region in which the paper-based measurement apparatus is located.

The selection unit 2640*b* is configured to obtain compensation information corresponding to the region from the obtained compensation information.

The compensation unit 2640*c* is configured to compensate for the measurement value according to the selected compensation information.

Based on the above, according to the test-paper-based measurement apparatus provided in this embodiment, corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

In addition, compensation information is stored in a server, so that on one hand, a storage space of a blood glucose meter can be reduced, and on the other hand, a compensation range of the blood glucose meter can be updated in real time according to an error during blood glucose test strip production, and therefore compensation can also be implemented when a test strip error change is excessively large or data is incorrect due to a use environment.

It should further be noted that a large quantity of users of blood glucose meters are elderly users, and the elderly users have difficulty in completing relatively complex operations when using a blood glucose meter. Therefore, for the elderly users, the operating difficulty in operating the blood glucose meter can be effectively reduced by using a color, a pattern, a number, or a graphic code as a calibration information identifier and by using a manner of selecting a candidate calibration information identifier, inputting a voice, or scanning a graphic code as an input mode, thereby avoiding the problem that the elderly users cannot smoothly complete the test strip measurement process due to the excessively high operating difficulty.

It should be noted that according to the test-paper-based measurement apparatuses provided by the foregoing embodiments, the above functional modules are only described for exemplary purposes. In actual applications, the functions may be allocated to different functional modules according to specific needs, which means that the internal structure of the apparatus is divided to different functional modules to complete all or some of the above described functions. In addition, the test-paper-based measurement apparatuses provided by the foregoing embodiments are based on the same concept as the test-paper-based measurement methods in the foregoing embodiments. For the specific implementation process, refer to the method embodiments, and the details are not described herein again.

Figure 28:
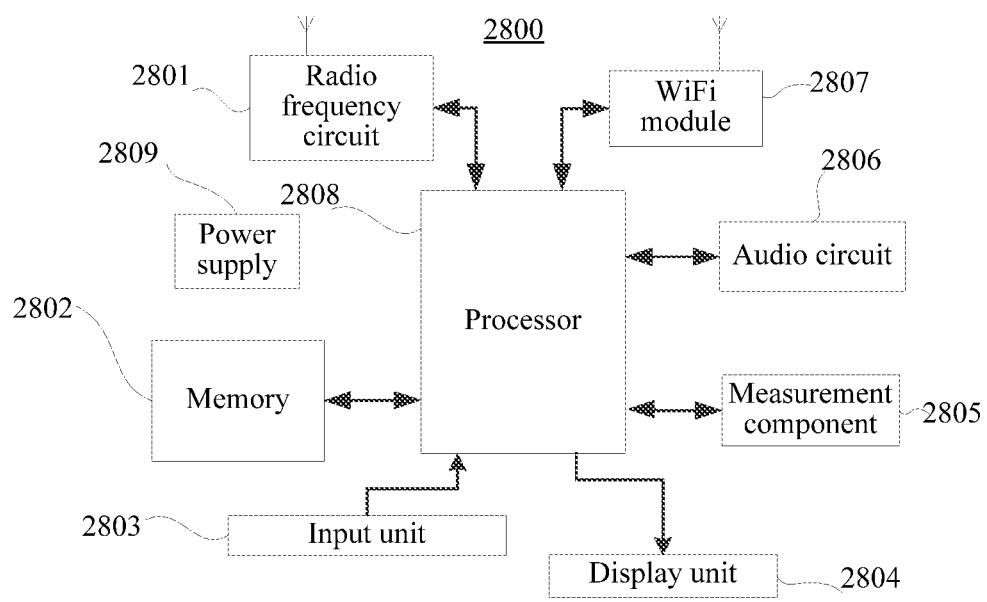
FIG. 28 is a block diagram of a test strip analysis device according to an embodiment of the present disclosure.

Referring to FIG. 28, FIG. 28 is a block diagram of a test strip analysis device 2800 according to an embodiment of the present disclosure. The test strip analysis device may include components such as a radio frequency (RF) circuit 2801, a memory 2802 including one or more computer readable storage media, an input unit 2803, a display unit 2804, a measurement component 2805, an audio circuit 2806, a WiFi module 2807, a processor 2808 including one or more processing cores, and a power supply 2809. A person skilled in the art may understand that the structure of the test strip analysis device shown in FIG. 28 does not constitute a limitation to the test strip analysis device, and the test strip analysis device may include more components or fewer components than those shown in the figure, or some components may be combined, or a different component deployment may be used. The foregoing RF circuit and/or WiFi module may also be generally referred to as communications components.

The RF circuit 2801 may be configured to receive and send signals during an information receiving and sending process or a call process. Particularly, the RF circuit 2801 receives downlink information from a base station, then delivers the downlink information to one or more processors 2808 for processing, and sends related uplink data to the base station. Generally, the RF circuit 2801 includes, but is not limited to, an antenna, at least one amplifier, a tuner, one or more oscillators, a subscriber identity module (SIM) card, a transceiver, a coupler, a low noise amplifier (LNA), and a duplexer. In addition, the RF circuit 2801 may also communicate with a network and another device by wireless communication. The wireless communication may use any communications standard or protocol, which includes, but is not limited to, Global System for Mobile communications (GSM), General Packet Radio Service (GPRS), Code Division Multiple Access (CDMA), Wideband Code Division Multiple Access (WCDMA), Long Term Evolution (LTE), email, Short Messaging Service (SMS), and the like.

The memory 2802 may be configured to store a software program and module. The processor 2808 runs the software program and module stored in the memory 2802, to implement various functional applications and data processing. The memory 2802 may mainly include a program storage area and a data storage area. The program storage area may store an operating system, an application program required by at least one function (such as a sound playback function and an image display function), and the like. The data storage area may store data (such as audio data and an address book) created according to use of the test strip analysis device, and the like. In addition, the memory 2802 may include a high speed random access memory, and may also include a non-volatile memory, such as at least one magnetic disk storage device, a flash memory, or another volatile solid-state storage device. Correspondingly, the memory 2802 may further include a memory controller, so as to facilitate access of the processor 2808 and the input unit 2803 to the memory 2802.

The input unit 2803 may be configured to receive input digit or character information, and generate a keyboard, mouse, joystick, optical, or track ball signal input related to the user setting and function control. Specifically, in a specific embodiment, the input unit 2803 may include a touch-sensitive surface and another input device. The touch-sensitive surface, which may also be referred to as a touch-screen or a touch panel, may collect a touch operation of a user on or near the touch-sensitive surface (such as an operation of a user on or near the touch-sensitive surface by using any suitable object or accessory, such as a finger or a stylus), and drive a corresponding connection apparatus according to a preset program. Optionally, the touch-sensitive surface may include two parts: a touch detection apparatus and a touch controller. The touch detection apparatus detects a touch position of the user, detects a signal generated by the touch operation, and transfers the signal to the touch controller. The touch controller receives the touch signal from the touch detection apparatus, converts the touch signal into touch point coordinates, and sends the touch point coordinates to the processor 2808. Moreover, the touch controller can receive and execute a command sent from the processor 2808. In addition, the touch-sensitive surface may be may be a resistive, capacitive, infrared, or surface sound wave type touch-sensitive surface. In addition to the touch-sensitive surface, the input unit 2803 may further include other input device. Specifically, the other input device may include, but is not limited to, one or more of a physical keyboard, a functional key (such as a volume control key or a switch key), a track ball, a mouse, and a joystick.

The display unit 2804 may be configured to display information input by the user or information provided for the user, and various graphical user interfaces of the test strip analysis device. The graphical user interfaces may be formed by a graph, a text, an icon, a video, or any combination thereof. The display unit 2804 may include a display panel. Optionally, the display panel may be configured by using a liquid crystal display (LCD), an organic light-emitting diode (OLED), or the like. Further, the touch-sensitive surface may cover the display panel. After detecting a touch operation on or near the touch-sensitive surface, the touch-sensitive surface transfers the touch operation to the processor 2808, so as to determine the type of the touch event. Then, the processor 2808 provides a corresponding visual output on the display panel according to the type of the touch event. Although, in FIG. 28, the touch-sensitive surface and the display panel are used as two separate parts to implement input and output functions, in some embodiments, the touch-sensitive surface and the display panel may be integrated to implement the input and output functions.

The test strip analysis device may further include a measurement component 2805, which is a component configured to convert information on a test strip into an electric signal. For example, the measurement component 2805 is a component that converts blood glucose information on a blood glucose test strip contaminated with blood into an electric signal. In different test strip analysis devices, functions of the measurement component 2805 are different.

Optionally, the test strip analysis device may further include at least one sensor such as an optical sensor, a motion sensor, and other sensors. Specifically, the optical sensor may include an ambient light sensor and a proximity sensor. The ambient light sensor may adjust luminance of the display panel according to brightness of the ambient light. The proximity sensor may switch off the display panel and/or backlight when the test strip analysis device is moved to the ear. As one type of motion sensor, a gravity acceleration sensor can detect magnitude of accelerations in various directions (generally on three axes), may detect magnitude and a direction of the gravity when static, and may be applied to an application that recognizes the attitude of the mobile phone (for example, switching between landscape orientation and portrait orientation, a related game, and magnetometer attitude calibration), a function related to vibration recognition (such as a pedometer and a knock), and the like. Other sensors, such as a gyroscope, a barometer, a hygrometer, a thermometer, and an infrared sensor, which may be configured in the test strip analysis device, are not further described herein.

The audio circuit 2806, a speaker, and a microphone may provide audio interfaces between the user and the test strip analysis device. The audio circuit 2806 may convert received audio data into an electric signal and transmit the electric signal to the speaker. The speaker converts the electric signal into a sound signal for output. On the other hand, the microphone converts a collected sound signal into an electric signal. The audio circuit 2806 receives the electric signal and converts the electric signal into audio data, and outputs the audio data to the processor 2808 for processing. Then, the processor 2808 sends the audio data to, for example, another test strip analysis device by using the RF circuit 2801, or outputs the audio data to the memory 2802 for further processing. The audio circuit 2806 may further include an earplug jack, so as to provide communication between a peripheral earphone and the test strip analysis device.

WiFi is a short distance wireless transmission technology. The test strip analysis device may help, by using the WiFi module 2807, the user to receive and send emails, browse a web page, access streaming media, and so on, which provides wireless broadband Internet access for the user. Although FIG. 28 shows the WiFi module 2807, it may be understood that the WiFi module 2807 is not a necessary component of the test strip analysis device, and when required, the WiFi module 2807 may be omitted as long as the scope of the essence of the present disclosure is not changed.

The processor 2808 is the control center of the test strip analysis device, and is connected to various parts of the mobile phone by using various interfaces and lines. By running or executing the software program and/or module stored in the memory 2802, and invoking data stored in the memory 2802, the processor 2808 performs various functions and data processing of the test strip analysis device, thereby performing overall monitoring on the mobile phone. Optionally, the processor 2808 may include one or more processing cores. Preferably, the processor 2808 may integrate an application processor and a modem. The application processor mainly processes an operating system, a user interface, an application program, and the like. The modem mainly processes wireless communication. It may be understood that the foregoing modem may either not be integrated into the processor 2808.

The test strip analysis device further includes the power supply 2809 (such as a battery) for supplying power to the components. Preferably, the power supply may be logically connected to the processor 2808 by using a power management system, thereby implementing functions such as charging, discharging and power consumption management by using the power management system. The power supply 2809 may further include one or more of a direct current or alternating current power supply, a re-charging system, a power failure detection circuit, a power supply converter or inverter, a power supply state indicator, and any other components.

Although not shown in the figure, the test strip analysis device may further include a camera, a Bluetooth module, and the like, which are not further described herein. Specifically, in this embodiment, the processor 2808 in the test strip analysis device runs one or more program instructions stored in the memory 2802, so as to implement test-paper-based measurement methods according to the foregoing various method embodiments.

Beneficial effects brought by the technical solutions provided in the embodiments of the present invention include: corresponding compensation information is obtained by obtaining a calibration information identifier of a test strip, and then compensation is performed, according to the obtained compensation information, for a measurement value obtained by measurement performed by a user, so that the problem of low accuracy of a blood glucose value obtained by the measurement performed by the user due to a calibration information existing in a blood glucose test strip in the foregoing prior art is resolved, thereby achieving the effect of improving the accuracy of a measurement value obtained by measurement by using a test strip.

A person of ordinary skill in the art may understand that all or some of the steps in the test-paper-based measurement methods in the foregoing embodiments may be performed by a program instructing relevant hardware. The program may be stored in a computer readable storage medium. The storage medium may be a read only memory (ROM), a random access memory (RAM), a magnetic disk, an optical disc, or the like.

It should be understood that unless the context clearly indicates otherwise, the singular form "one" ("a", "an", and "the") used herein aims to include plural forms as well. It should also be understood that as used herein, the term "and/or" refers to any and all combinations of the associated listed items.

The sequence numbers of the foregoing embodiments of the present disclosure are merely for the convenience of description, and do not imply the preference among the embodiments.

A person of ordinary skill in the art may understand that all or some of the steps of the foregoing embodiments may be implemented by using hardware, or may be implemented by a program instructing relevant hardware. The program may be stored in a computer readable storage medium. The storage medium may be a read-only memory, a magnetic disk, an optical disc, or the like.

The foregoing descriptions are merely preferred embodiments of the present disclosure, but are not intended to limit the present disclosure. Any modification, equivalent replacement, or improvement made within the spirit and principle of the present disclosure shall fall within the protection scope of the present disclosure.

Figure 29:
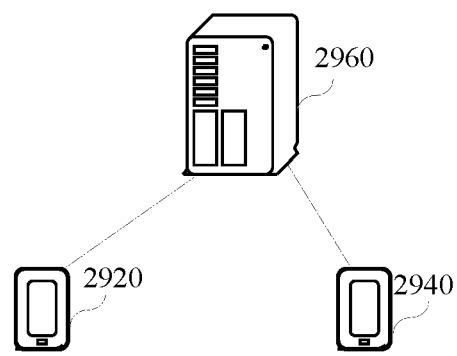
FIG. 29 is a schematic structural diagram of an implementation environment according to an embodiment of the present disclosure.

Referring to FIG. 29, FIG. 29 is a schematic structural diagram of an implementation environment according to an embodiment of the present disclosure. The implementation environment includes: a first device 2920, a second device 2940, and a server 2960.

The first device 2920 may be a health data measurement device having a data transmission function, such as a blood glucose meter, a sphygmomanometer, or a fat meter. The first device 2920, as used herein, may also be referred as a health management apparatus.

The second device 2940 may be an intelligent device, on which a third-party application program is installed, such as a mobile phone, a tablet computer, or a personal computer.

Optionally, the third-party application program is a communications application program, such as WeChat, a microblog, or QQ.

The server 2960 is a background server of a third-party application program. The server 2960 may be one server, a server cluster formed by multiple servers, or a cloud computing center.

The first device 2920 is connected to the second device 2940 by using a wireless network or a wired network. A measurement result of the first device 2920 is processed by the server 2960, and then is sent, by the server 2960, to the third-party application program that runs in the second device 2940.

Figure 30:
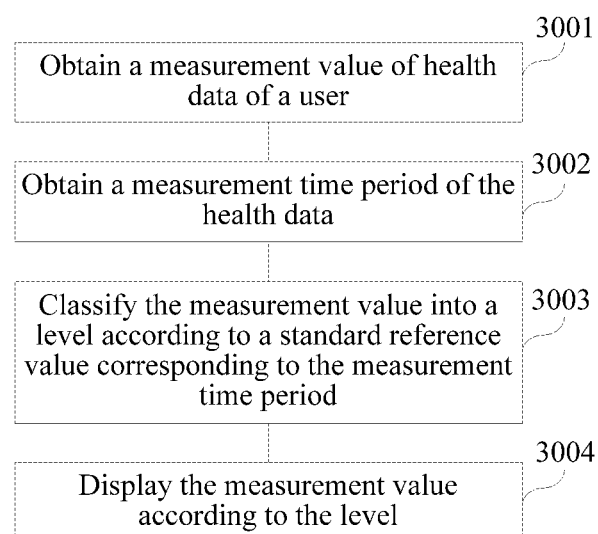
FIG. 30 is a method flowchart of a method for displaying health data according to an embodiment of the present disclosure.

Referring to FIG. 30, FIG. 30 is a flowchart of a method for displaying health data according to an exemplary embodiment of the present disclosure. This embodiment is described by using that the method for displaying health data is applied to the first device shown in FIG. 29 as an example. The method for displaying health data includes step 3001 to step 3004.

In step 3001, a measurement value of health data of a user is obtained. The health data, as used herein, may also be referred as physiological data.

A health data measurement device obtains a measurement value of health data of a user.

Optionally, the measurement value of the health data is a measurement result that is represented in a numerical form and obtained by measurement for an index of the user by using the health data measurement device by the user, such as a blood glucose value, a blood pressure value, or a body fat rate.

In step 3002, a measurement time period of the health data is obtained.

The health data measurement device obtains a measurement time period of the health data.

Optionally, the measurement time period of the health data is a time range, to which a moment for health data measurement belongs.

In step 3003, the measurement value is classified into a level according to a standard reference value corresponding to the measurement time period.

The health data measurement device classifies the measurement result into a level according to a standard reference value corresponding to the measurement time period.

Optionally, the standard reference value is a standard value or a data range obtained by measurement by a person skilled in the art.

In step 3004, the measurement value is displayed according to the level.

The health data measurement device displays the measurement value on a display interface according to the level corresponding to the measurement value.

Based on the above, according to the method for displaying health data provided in this embodiment, by obtaining a measurement time period of health data, classifying the measurement value into a level according to a standard reference value corresponding to the measurement time period, and displaying the measurement value according to the level, the problem that a user cannot determine health data in a numerical form and a suitable standard reference value because the health data in the numerical standard form is excessively professional is resolved, thereby achieving the effect of enabling the user to determine a level of current health data more easily, so that the user can learn the current health condition more intuitively, so as to avoid affecting related nursing or treatment time.

Figure 31:
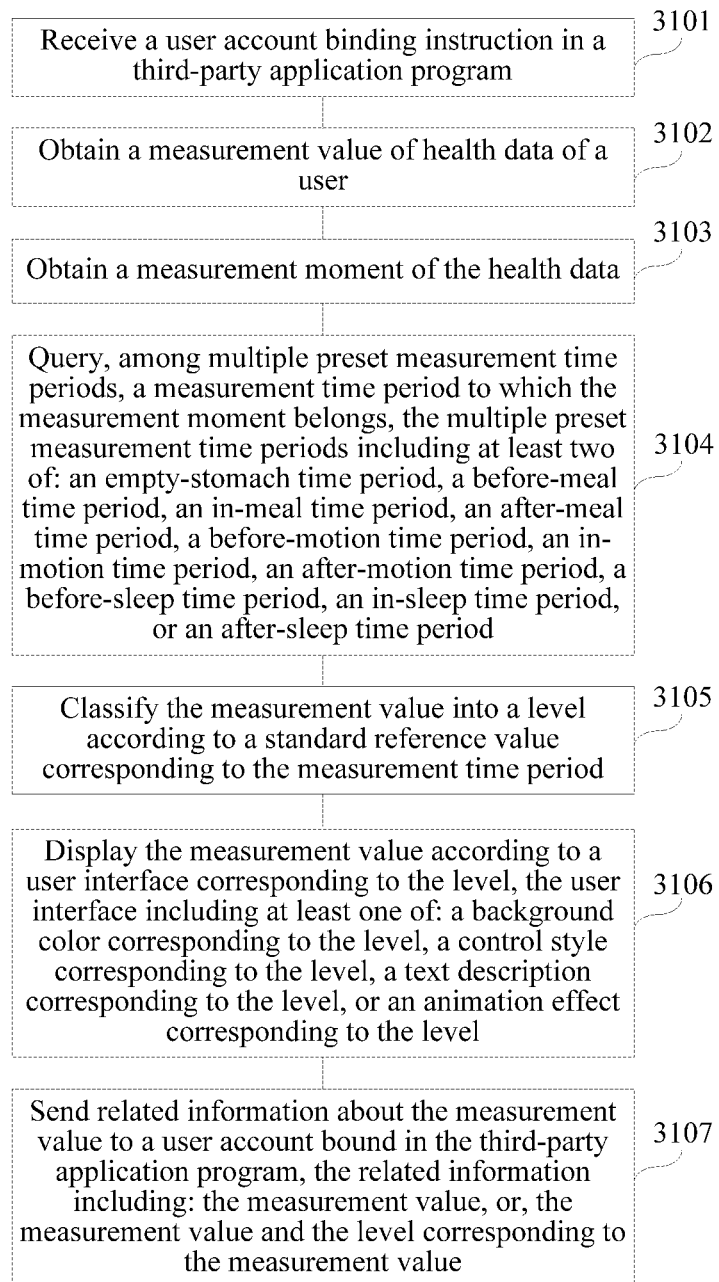
FIG. 31 is a method flowchart of a method for displaying health data according to another embodiment of the present disclosure.

Referring to FIG. 31, FIG. 31 is a flowchart of a method for displaying health data according to another exemplary embodiment of the present disclosure. This embodiment is described by using that the method for displaying health data is applied to the first device shown in FIG. 29 as an example. The method for displaying health data includes step 3101 to step 3107.

In step 3101, a user account binding instruction in a third-party application program is received.

Before receiving a measurement result sent by a health data measurement device, a user account of a third-party application program needs to first complete binding to the health data measurement device.

Correspondingly, the health data measurement device receives a user binding instruction of the third-party application program, and completes the user binding instruction of the third-party application program, to facilitate sending related information about a measurement value.

In step 3102, a measurement value of health data of a user is obtained.

A user measures an index of himself/herself by using the health data measurement device, and the health data measurement device obtains the measurement value of health data of the user.

For example, the user measures his/her blood glucose by using a blood glucose meter, and the blood glucose meter obtains a blood glucose value of the user.

In step 3103, a measurement moment of the health data is obtained.

The health data measurement device obtains a moment for health data measurement of the user.

In step 3104, a measurement time period to which the measurement moment belongs is queried in multiple preset/candidate measurement time periods, the peset measurement time periods including at least two of: an empty-stomach time period, a before-meal time period, an in-meal time period, an after-meal time period, a before-motion (or before-exercise) time period, an in-motion time period, an after-motion time period, a before-sleep time period, an in-sleep time period, or an after-sleep time period.

Time for health data measurement performed by the user is usually a moment, but the user cannot ensure that measurement of each time is performed at a same moment, and a reference standard value of the health data does not greatly change. Therefore, a measurement time period to which a measurement moment of the health data belongs can be queried according to the measurement moment of the health data, and the health data obtained by measurement is analyzed.

Optionally, the measurement time period is a default time period of a system or a time period set by the user himself/herself according to life habits. Starting and ending time of each time period can be freely changed, and there is at least one measurement time period.

For example, the user measures blood glucose at home by using the blood glucose meter. There are 7 time periods for system initialization of the blood glucose meter. Starting and ending time of each time period is shown in the following table:

TABLE 2

| Name of time period | Time range |
| --- | --- |
| Empty-stomach time period | 00:00 to 8:00 |
| After-breakfast time period | 08:00 to 10:00 |
| Before-lunch time period | 10:00 to 12:00 |
| After-lunch time period | 12:00 to 16:00 |
| Before-supper time period | 16:00 to 18:00 |
| After-supper time period | 18:00 to 20:00 |
| Before-sleep time period | 20:00 to 00:00 |

The empty-stomach time period is 00:00 to 8:00; the after-breakfast time period is 08:00 to 10:00; the before-lunch time period is 10:00 to 12:00; the after-lunch time period is 12:00 to 16:00; the before-supper time period is 16:00 to 18:00; the after-supper time period is 18:00 to 20:00; the before-sleep time period is 20:00 to 00:00. Generally, the empty-stomach time period specifically refers to a before-breakfast time period, and non-empty-stomach time periods generally refer to the after-breakfast time period, the before-lunch time period, the after-lunch time period, the before-supper time period, the after-supper time period, and the before-sleep time period. Moreover, a blood glucose value of the empty-stomach time period is greatly different from blood glucose values of other non-empty-stomach time periods. In addition, because blood glucose in meals is in an elevated stage, and is unstable, a measured blood glucose value lacks reference value. Optionally, in-meal time periods for blood glucose measurement are not set.

The user performs blood glucose measurement at 13:30 one day. A result of the blood glucose measurement is 8.9 mmol/L, and a blood glucose measurement moment obtained by the blood glucose meter is 13:30. The blood glucose meter queries, according to three preset measurement time periods, a measurement time period to which 13:30 belongs, and finds that the measurement time period to which 13:30 belongs is the after-lunch time period, that is, a non-empty-stomach time period.

In step 3105, the measurement value is classified into a level according to standard reference values corresponding to the measurement time period.

The health data measurement device compares the measurement value with the standard reference values corresponding to the measurement time period, and classifies the measurement value into a level according to a result of the comparison.

By using blood glucose measurement as an example, a correspondence between time periods for blood glucose measurement and standard reference values is shown in the following table:

TABLE 3

| Measurement time period | Standard reference value |
| --- | --- |
| Empty-stomach time period | 4.3 to 7.2 (mmol/L) |
| Non-empty-stomach time period | 4.3 to 10 (mmol/L) |

The standard reference value of the empty-stomach time period is 4.3 to 7.2 mmol/L, and the standard reference value of the non-empty-stomach time period is 4.3 to 10 mmol/L.

A level relationship corresponding to the result of the comparison between the blood glucose measurement value and the standard reference value is shown in the following table:

TABLE 4

| Comparison result (blood glucose value is X mmol/L) | Level |
| --- | --- |
| $X < 4.3$ | Lower than a normal level |
| $4.3 \leq X \leq 10$ | Normal (non-empty-stomach time period) |
| $X > 10$ | Higher than the normal level (non-empty-stomach time period) |
| $4.3 \leq X \leq 7.2$ | Normal (empty-stomach time period) |
| $X > 7.2$ | Higher than the normal level (empty-stomach time period) |

As shown in Table 4, according to different measurement time periods, when the blood glucose value is less than 4.3 mmol/L, the blood glucose level is lower than the normal level; when the blood glucose value is greater than 10 mmol/L in the non-empty-stomach time period or the blood glucose value is greater than 7.2 mmol/L in the empty-stomach time period, the blood glucose level is higher than the normal level; when the blood glucose value is greater than or equal to 4.3 mmol/L and less than or equal to 10 mmol/L in the non-empty-stomach time period, or the blood glucose value is greater than or equal to 4.3 mmol/L and less than or equal to 7.2 mmol/L in the empty-stomach time period, the blood glucose level is normal.

For example, the user measures blood glucose at 13:30 and obtains that the blood glucose value is 8.9 mmol/L, and the measurement time period is the after-lunch time period, that is, the non-empty-stomach time period, according to the blood glucose standard reference value of the non-empty-stomach time period, it is learned that the blood glucose level is normal.

In step 3106, the measurement value is displayed according to a user interface corresponding to the level, the user interface including at least one of: a background color corresponding to the level, a control style corresponding to the level, a text description corresponding to the level, or an animation effect corresponding to the level. In some embodiments, the measured blood glucose value, the corresponding level, and the measurement time period may be all displayed on the graphical interface. Further, the standard reference values corresponding to the measurement time period may also be displayed.

The health data measurement device displays the measurement value according to a user interface corresponding to the level of the measurement value.

Optionally, for different levels, the user interface displays different background colors, different space styles, different text descriptions, and different animation effects.

For example, by using the blood glucose meter as an example, different levels of measured blood glucose values correspond to different background colors of the user interface of the user interface: being lower than the normal level corresponds to yellow; being normal corresponds to blue; being higher than the normal level corresponds to red; when the measurement level is continuously higher than the normal level, a background color, corresponding to the level of being higher than the normal level, of the user display interface may be deepened.

Optionally, for different levels, the user interface may display background colors and text descriptions corresponding to the levels. For example, when the level of the blood glucose value of the user is higher than the normal level, the background color of the user interface is red, and the text description is "Blood glucose is higher than a normal level. Please seek professional advice from a doctor", and the like.

In step 3107, related information about the measurement value is sent to a user account bound in the third-party application program, the related information including: the measurement value, or, the measurement value and the level corresponding to the measurement value.

The step specifically includes: uploading the related information about the measurement value to a background server of the third-party application program, the background server being configured to send the related information about the measurement value to the user account bound in the third-party application program.

After completing measurement on the health data, the health data measurement device uploads the related information about the measurement value to the background server of the third-party application program, and the background server sends the related information about the measurement value to the user account bound in the third-party application program.

Optionally, the third-party application program displays the measurement value according to the related information, sent by the server, about the measurement value.

Optionally, the information sent by the server includes the measurement value and the level corresponding to the measurement value, and then the display interface of the third-party application program also displays the measurement value and the level corresponding to the measurement value.

For example, a user measures blood glucose at 13:30 and obtains that the blood glucose value is 7.9 mmol/L, and the blood glucose level is normal. The user account bound in the third-party application program receives related information about the measurement value. There are text descriptions such as "blood glucose value: 7.9 mmol/L" and "blood glucose level: normal" on the display interface of the third-party application program.

It should be noted that in this embodiment, a binding relationship may be established with the user account in the third-party application program at any moment before the related information about the measurement value is sent, and therefore a sequence for performing step 3101 is not particularly limited in this embodiment of the present disclosure.

Based on the above, according to the method for displaying health data provided in this embodiment, by obtaining a measurement time period of health data, classifying the measurement value into a level according to a standard reference value corresponding to the measurement time period, and displaying the measurement value according to the level, the problem that a user cannot determine health data in a numerical form and a suitable standard reference value because the health data in the numerical standard form is excessively professional is resolved, thereby achieving the effect of enabling the user to determine a level of current health data more easily, so that the user can learn the current health condition more intuitively, so as to avoid affecting related nursing or treatment time.

In addition, according to the method for displaying health data provided in this embodiment, status information in a social account of the user may further be obtained, and a measurement time period is determined according to the status information, thereby achieving the effect of diversifying manners of obtaining the measurement time period of the health data.

In addition, according to the method for displaying health data provided in this embodiment, related information about a measurement value may alternatively be sent to an account, bound in the third-party application program, of a relative of the user, so that the relative of the user corresponding to the health data can learn the health condition of the user more timely, thereby warning the measurement result more comprehensively.

Figure 32:
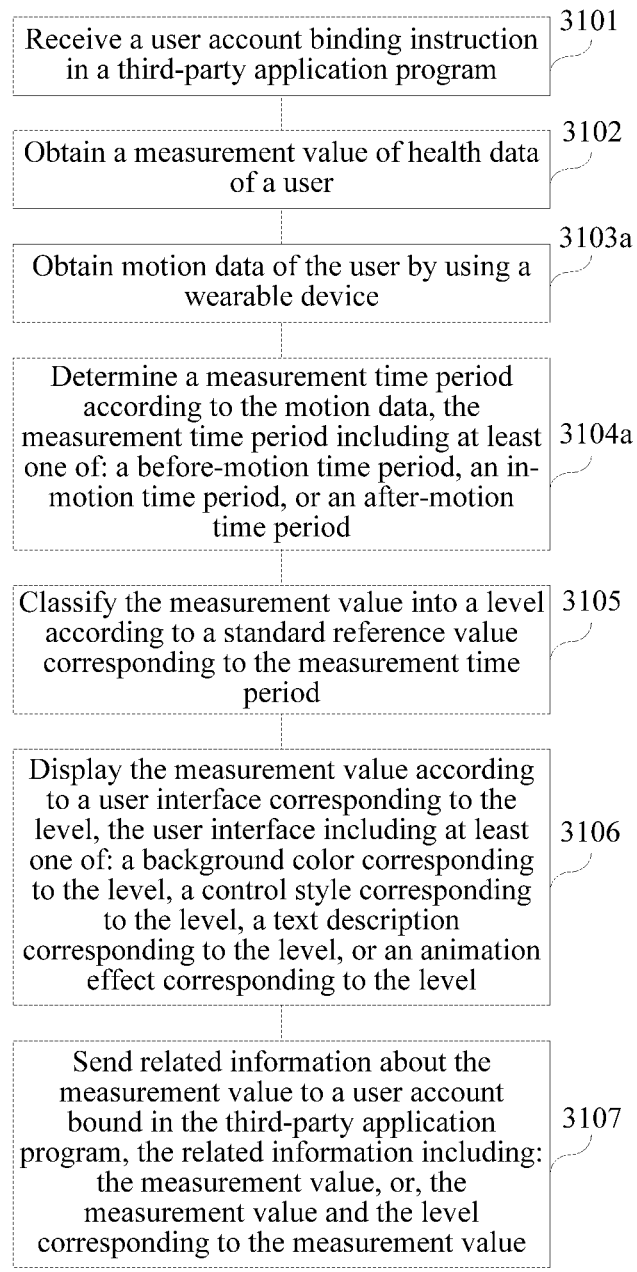
FIG. 32 is a method flowchart of a method for displaying health data according to another embodiment of the present disclosure.

Based on the optional embodiment shown in FIG. 31, the measurement time period of the health data may further be obtained by using a wearable device. That is, step 3103 may be replaced for implementation into step 3103a, and step 3104 may be replaced for implementation into step 3104a, as shown in FIG. 32.

In step 3103a, motion data of the user is obtained by using a wearable device.

Optionally, the wearable device can record motion data of the user, such as motion time, a motion amount, and a motion manner.

Optionally, the wearable device is a portable device that is directly worn on body, or is integrated into clothes or accessories of the user, and is a device having a data interaction function, such as an intelligent hand loop or intelligent glasses.

In step 3104a, a measurement time period is determined according to the motion data, the measurement time period including at least one of: a before-motion time period, an in-motion time period, or an after-motion time period.

The health data measurement device determines the measurement time period according to the motion data, obtained by the wearable device, of the user.

Figure 33:
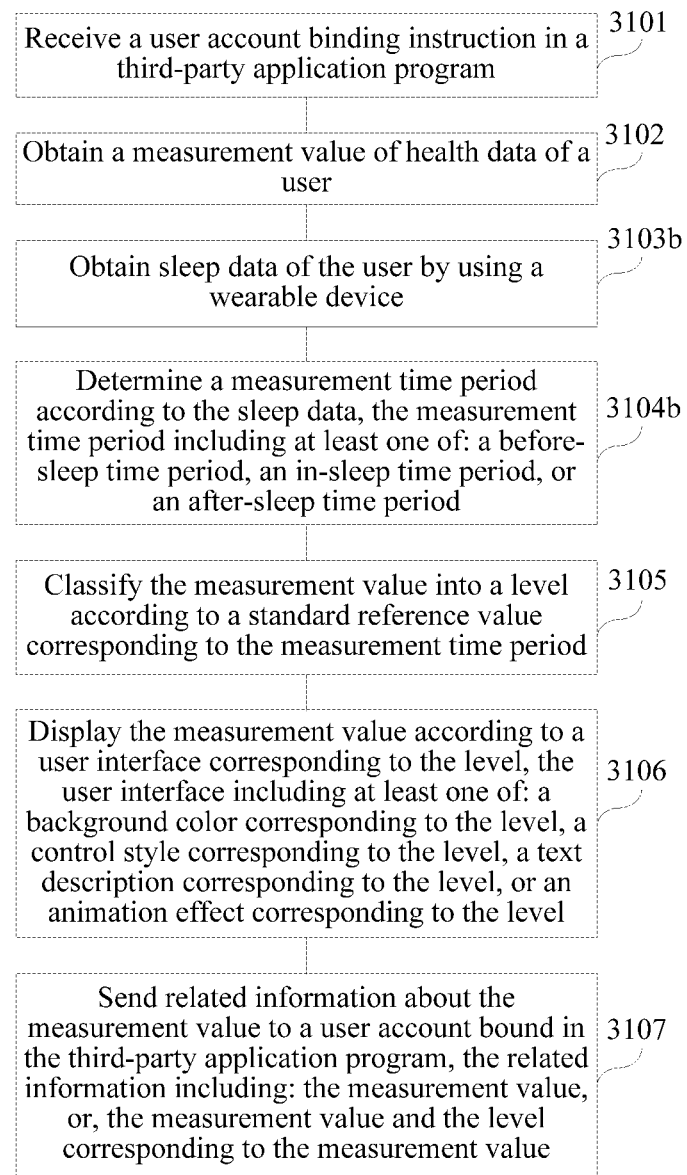
FIG. 33 is a method flowchart of a method for displaying health data according to another embodiment of the present disclosure.

Based on the optional embodiment shown in FIG. 31, the measurement time period of the health data may further be obtained by using a wearable device. That is, step 3103 may be replaced for implementation into step 3103b, and step 3104 may be replaced for implementation into step 3104b, as shown in FIG. 33.

In step 3103b, sleep data of the user is obtained by using a wearable device.

Optionally, sleep data is data that can reflect conditions related to sleep of the user, such as sleep time and sleep depth.

In step 3104b, a measurement time period is determined according to the sleep data, the measurement time period including at least one of: a before-sleep time period, an in-sleep time period, or an after-sleep time period.

The health data measurement device determines the measurement time period according to the sleep data, obtained by the wearable device, of the user.

Figure 34:
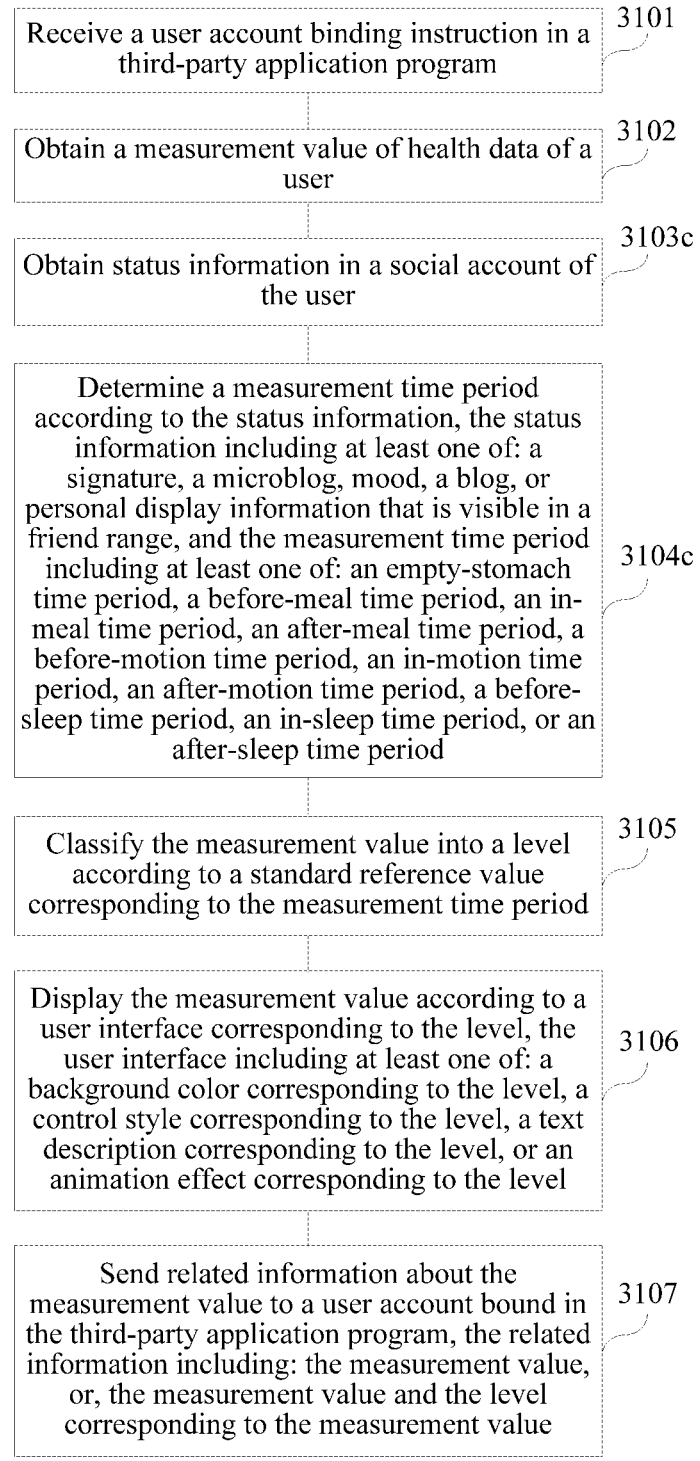
FIG. 34 is a method flowchart of a method for displaying health data according to another embodiment of the present disclosure.

Based on the optional embodiment shown in FIG. 31, the measurement time period of the health data may further be obtained by using a related status of a social account of the user. That is, step 3103 may be replaced for implementation into step 3103c, and step 3104 may be replaced for implementation into step 3104c, as shown in FIG. 34.

In step 3103c, status information in a social account of the user is obtained.

The health data measurement device obtains status information in a social account of the user.

In step 3104c, a measurement time period is determined according to the status information, the status information including at least one of: a signature, a microblog, mood, a blog, or personal display information that is visible in a friend range, and the measurement time period including at least one of: an empty-stomach time period, a before-meal time period, an in-meal time period, an after-meal time period, a before-motion time period, an in-motion time period, an after-motion time period, a before-sleep time period, an in-sleep time period, or an after-sleep time period.

For example, the user publishes a status "The cake I just ate is great!" on a microblog, the health data measurement device can determine, according to time when the status is published, a measurement time period to which a measurement moment belongs.

In an exemplary example, the first device is a blood glucose meter, and the second device is a smartphone. A third-party application WeChat is installed in the second device. The blood glucose meter is bound to a WeChat account W.

It is learned that Xiaoming sets 7 time periods for the blood glucose meter; the empty-stomach time period is 00:00 to 8:00; the after-breakfast time period is 08:00 to 10:00; the before-lunch time period is 10:00 to 12:00; the after-lunch time period is 12:00 to 16:00; the before-supper time period is 16:00 to 18:00; the after-supper time period is 18:00 to 20:00; the before-sleep time period is 20:00 to 00:00.

Figure 35A:
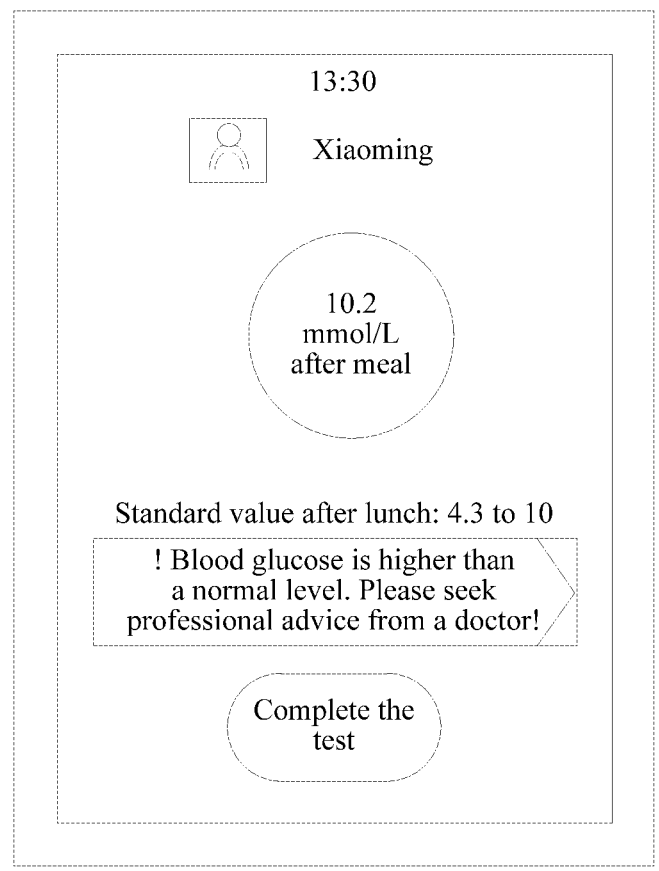
FIG. 35A is a schematic diagram of implementation of a method for displaying health data according to another embodiment of the present disclosure.

Xiaoming measures his blood glucose at 13:30, Sep. 30, 2015. The blood glucose measurement result is 10.2 mmol/L. As shown in FIG. 35A, a user interface of the blood glucose meter displays that the blood glucose result is 10.2 mmol/L, the background color of the interface is red, and the text descriptions are "Standard value after lunch: 4.3 to 10" and "Blood glucose is higher than a normal level. Please seek professional advice from a doctor".

Figure 35B:
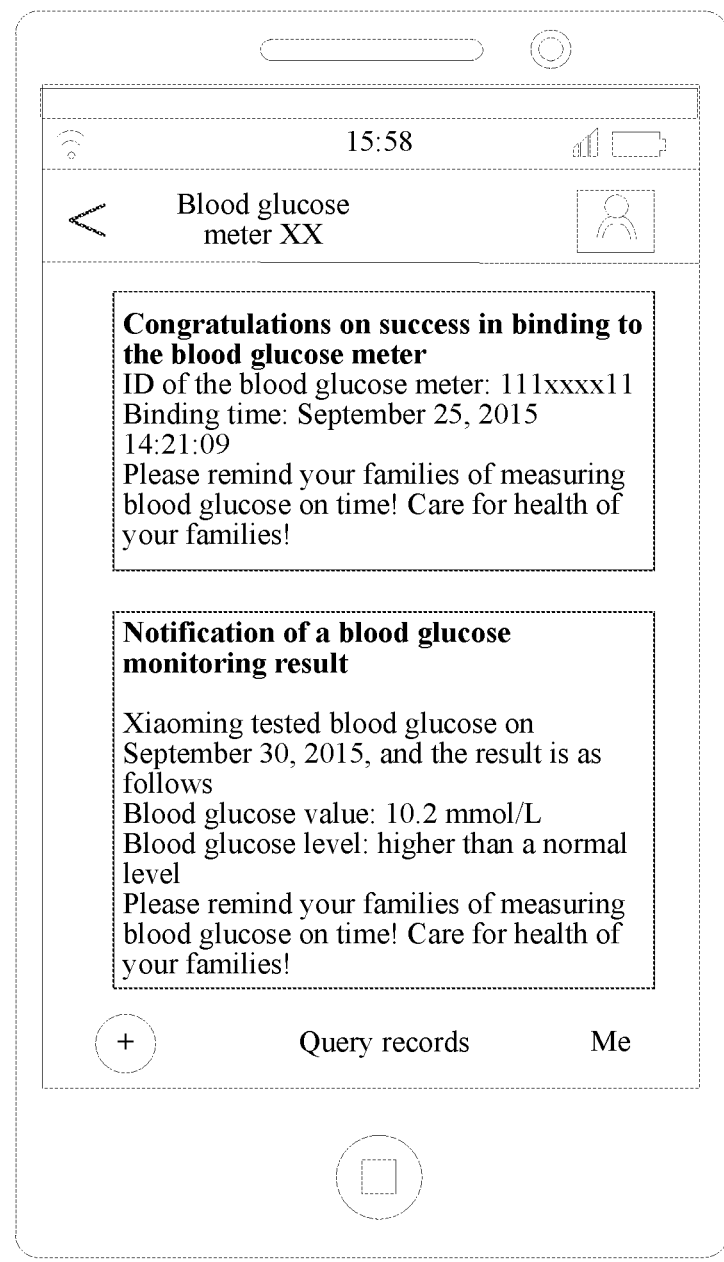
FIG. 35B is a schematic diagram of implementation of a method for displaying health data according to another embodiment of the present disclosure.

After Xiaoming completes the blood glucose test, the blood glucose meter sends the blood glucose value and the blood glucose level of Xiaoming to the WeChat account W, as shown in FIG. 35B, so that a user W can view the blood glucose result of Xiaoming on a WeChat interface.

Figure 36:
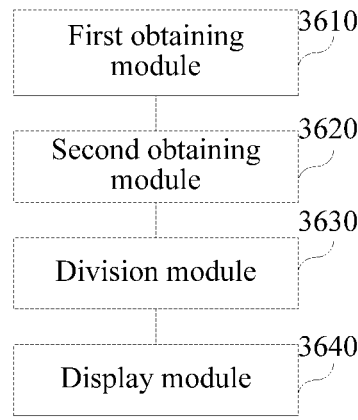
FIG. 36 is structural block diagram of a health index measurement apparatus according to an embodiment of the present disclosure.

Referring to FIG. 36, FIG. 36 is a structural block diagram of an apparatus for displaying health data according to an embodiment of the present disclosure. The apparatus for displaying health data provided in this embodiment may be implemented as all or a part of a first terminal by software, hardware, or a combination thereof. The apparatus includes: a first obtaining module 3610, configured to obtain a measurement value of health data of a user; a second obtaining module 3620, configured to obtain a measurement time period of the health data; a division module 3630, configured to classify the measurement value into a level according to a standard reference value corresponding to the measurement time period; and a display module 3640, configured to display the measurement value according to the level.

Based on the above, according to the apparatus for displaying health data provided in this embodiment, by obtaining a measurement time period of health data, classifying the measurement value into a level according to a standard reference value corresponding to the measurement time period, and displaying the measurement value according to the level, the problem that a user cannot determine health data in a numerical form and a suitable standard reference value because the health data in the numerical standard form is excessively professional is resolved, thereby achieving the effect of enabling the user to determine a level of current health data more easily, so that the user can learn the current health condition more intuitively, so as to avoid affecting related nursing or treatment time.

Figure 37:
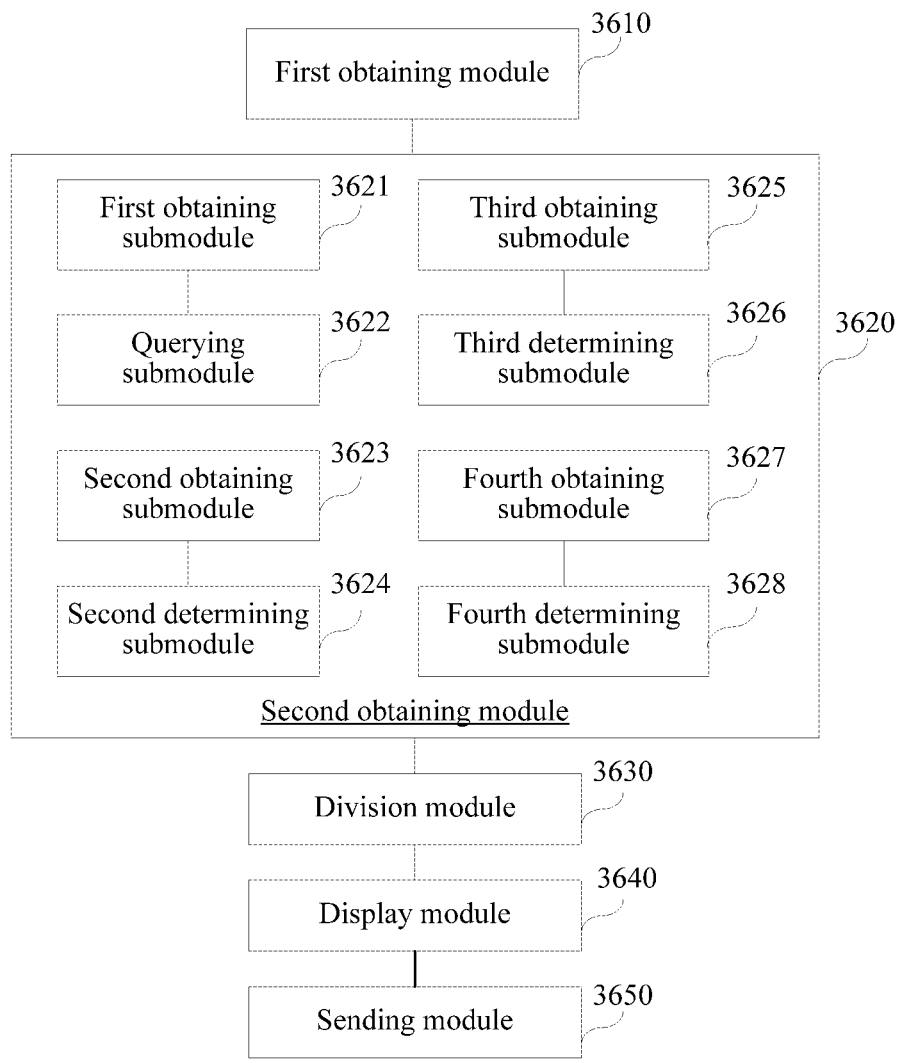
FIG. 37 is structural block diagram of a health index measurement apparatus according to another embodiment of the present disclosure.

Referring to FIG. 37, FIG. 9 is a structural block diagram of an apparatus for displaying health data according to another embodiment of the present disclosure. The apparatus for displaying health data provided in this embodiment may be implemented as all or a part of a first terminal by software, hardware, or a combination thereof. The apparatus includes: a first obtaining module 3610, configured to obtain a measurement value of health data of a user; a second obtaining module 3620, configured to obtain a measurement time period of the health data; a division module 3630, configured to classify the measurement value into a level according to a standard reference value corresponding to the measurement time period; and a display module 3640, configured to display the measurement value according to the level.

Optionally, the second obtaining module 3620 includes: a first obtaining submodule 3621, configured to obtain a measurement moment of the health data; and a querying submodule 3622, configured to query, in at least one preset measurement time period, a measurement time period to which the measurement moment belongs, the measurement time period including at least one of: an empty-stomach time period, a before-meal time period, an in-meal time period, an after-meal time period, a before-motion time period, an in-motion time period, an after-motion time period, a before-sleep time period, an in-sleep time period, or an after-sleep time period.

Optionally, the second obtaining module 3620 includes a second obtaining submodule 3623, configured to obtain motion data of the user by using a wearable device; and a second determining submodule 3624, configured to determine the measurement time period according to the motion data, the measurement time period including at least one of: a before-motion time period, an in-motion time period, or an after-motion time period.

Optionally, the second obtaining module 3620 includes a third obtaining submodule 3625, configured to obtain sleep data of the user by using a wearable device; and a third determining submodule 3626, configured to determine the measurement time period according to the sleep data, the measurement time period including at least one of: a before-sleep time period, an in-sleep time period, or an after-sleep time period.

Optionally, the second obtaining module 3620 includes a fourth obtaining submodule 3627, configured to obtain status information in a social account of the user; and a fourth determining submodule 3628, configured to determine the measurement time period according to the status information, the status information including at least one of: a signature, a microblog, mood, a blog, or personal display information that is visible in a friend range, and the measurement time period including at least one of: an empty-stomach time period, a before-meal time period, an in-meal time period, an after-meal time period, a before-motion time period, an in-motion time period, an after-motion time period, a before-sleep time period, an in-sleep time period, or an after-sleep time period.

Optionally, the display module 3640 is specifically configured to display the measurement value according to a user interface corresponding to the level, the user interface including at least one of: a background color corresponding to the level, a control style corresponding to the level, a text description corresponding to the level, or an animation effect corresponding to the level.

Optionally, the apparatus further includes: a sending module 3650, configured to send related information about the measurement value to a user account bound in a third-party application program, where the related information includes: the measurement value, or, the measurement value and the level corresponding to the measurement value.

Optionally, the sending module 3650 is specifically configured to upload the related information about the measurement value to a background server of the third-party application program, the background server being configured to send the related information about the measurement value to the user account bound in the third-party application program.

Based on the above, according to the apparatus for displaying health data provided in this embodiment, by obtaining a measurement time period of health data, classifying the measurement value into a level according to a standard reference value corresponding to the measurement time period, and displaying the measurement value according to the level, the problem that a user cannot determine health data in a numerical form and a suitable standard reference value because the health data in the numerical standard form is excessively professional is resolved, thereby achieving the effect of enabling the user to determine a level of current health data more easily, so that the user can learn the current health condition more intuitively, so as to avoid affecting related nursing or treatment time.

In addition, according to the apparatus for displaying health data provided in this embodiment, status information in a social account of the user may further be obtained, and a measurement time period is determined according to the status information, thereby achieving the effect of diversifying manners of obtaining the measurement time period of the health data.

In addition, according to the apparatus for displaying health data provided in this embodiment, related information about a measurement value may alternatively be sent to an account, bound in the third-party application program, of a relative of the user, so that the relative of the user corresponding to the health data can learn the health condition of the user more timely, thereby warning the measurement result more comprehensively.

According to the technical solutions provided in the embodiments of the present invention, by obtaining a measurement time period of health data, classifying the measurement value into a level according to a standard reference value corresponding to the measurement time period, and displaying the measurement value according to the level, the problem that a user cannot determine health data in a numerical form and a suitable standard reference value because the health data in the numerical standard form is excessively professional is resolved, thereby achieving the effect of enabling the user to determine a level of current health data more easily, so that the user can learn the current health condition more intuitively, so as to avoid affecting related nursing or treatment time.

It should be noted that the above functional modules are only described for exemplary purposes when the apparatuses for displaying health data provided by the foregoing embodiments measure health data. In actual applications, the functions may be allocated to different functional modules according to specific needs, which means that the internal structure of the device is divided to different functional modules to complete all or some of the above described functions. In addition, the apparatuses for displaying health data provided by the foregoing embodiments are based on the same concept as the methods for displaying health data in the foregoing embodiments. For the specific implementation process, refer to the method embodiments, and the details are not described herein again.

The sequence numbers of the foregoing embodiments of the present disclosure are merely for the convenience of description, and do not imply the preference among the embodiments.

A person of ordinary skill in the art may understand that all or some of the steps of the foregoing embodiments may be implemented by using hardware, or may be implemented by a program instructing relevant hardware. The program may be stored in a computer readable storage medium. The storage medium may be a read-only memory, a magnetic disk, an optical disc, or the like.

The foregoing descriptions are merely preferred embodiments of the present disclosure, but are not intended to limit the present disclosure. Any modification, equivalent replacement, or improvement made within the spirit and principle of the present disclosure shall fall within the protection scope of the present disclosure.

What is claimed is:

1. A method for health management performed by an intelligent device upon which a third-party application program is installed, the intelligent device being in a communication with a measurement device and with a server of the third-party application program, the method comprising:
    displaying, by the intelligent device, a first graphical interface;
    receiving, by the first graphical interface of the intelligent device, login information of a user account and a click of a login box displayed on the first graphical interface, the intelligent device having a memory and a processor;
    after receiving the click of the login box displayed on the first graphical interface, displaying, by the intelligent device, a second graphical interface;
    receiving, by the second graphical interface of the intelligent device, a binding instruction;
    after receiving the binding instruction, establishing, by the intelligent device, a binding connection to the measurement device;
    after the binding connection is established, receiving, by the intelligent device, a measurement value from the measurement device via the server;
    displaying, on a third graphical interface of the intelligence device, the measurement value corresponding to a level according to standard reference values in a measurement time period, the third graphical interface includes at least one of: a background color corresponding to the level, a control style corresponding to the level, a text description corresponding to the level, or an animation effect corresponding to the level;
    obtaining, by the intelligent device, physiological data of a user based on the measurement value, wherein the obtaining the physiological data of the user comprises:
        displaying, by a fourth graphical interface of the intelligent device terminal, multiple candidate calibration information identifiers;
        receiving, via the fourth graphical interface of the intelligent device, a click selection for selecting the calibration information identifier among the candidate calibration information identifiers;
        displaying, on the fourth graphical interface of the intelligent device, the calibration information identifier as selected;
        obtaining, by the intelligent device, compensation information corresponding to the calibration information identifier, wherein the compensation information includes a first correspondence corresponding to the calibration information identifier being a first color and a second correspondence corresponding to the calibration information identifier being a second color different than the first color, and wherein each of the first and the second correspondences correlates measurement values respectively with compensation values;
        displaying on the fourth graphical interface the first and the second correspondences, wherein a same measurement value correlates to different compensation information under the first and the second correspondences as displayed; and
        adjusting the measurement value according to the compensation information to obtain the physiological data of the user;
    storing, by the intelligent device, the physiological data into a medical record corresponding to the first user account;
    receiving, via a fifth graphical interface of the intelligent device, a click of a consultation inlet displayed on the fifth graphical interface, wherein the click of the consultation inlet triggers a health consultation request of the first user account; and
    sending, together with the physiological data, the health consultation request of the user to a doctor terminal via a server, the doctor terminal being a user terminal of a healthcare provider, wherein the health consultation request is used to request the healthcare provider to provide health consultation service to the user based on the physiological data.

2. An apparatus for health management, comprising: a memory; a processor coupled to the memory; and a third-party application program being installed on the apparatus, wherein the processor is configured for:
    displaying a first graphical interface;
    receiving, by the first graphical interface, login information of a user account and a click of a login box displayed on the first graphical interface;
    after receiving the click of the login box displayed on the first graphical interface, displaying a second graphical interface;
    receiving, by the second graphical interface, a binding instruction;
    after receiving the binding instruction, establishing a binding connection to a measurement device;

after the binding connection is established, receiving a measurement value from the measurement device via a server;

displaying, on a third graphical interface, the measurement value corresponding to a level according to standard reference values in a measurement time period, the third graphical interface includes at least one of: a background color corresponding to the level, a control style corresponding to the level, a text description corresponding to the level, or an animation effect corresponding to the level;

obtaining physiological data of a user based on the measurement value, wherein the obtaining the physiological data of the user comprises:

displaying, by a fourth graphical interface, multiple candidate calibration information identifiers;

receiving, via the fourth graphical interface, a click selection for selecting the calibration information identifier among the candidate calibration information identifiers;

displaying, on the fourth graphical interface, the calibration information identifier as selected;

obtaining compensation information corresponding to the calibration information identifier, wherein the compensation information includes a first correspondence corresponding to the calibration information identifier being a first color and a second correspondence corresponding to the calibration information identifier being a second color different than the first color, and wherein each of the first and the second correspondences correlates measurement values respectively with compensation values;

displaying on the fourth graphical interface the first and the second correspondences, wherein a same measurement value correlates to different compensation information under the first and the second correspondences as displayed; and adjusting the measurement value according to the compensation information to obtain the physiological data of the user;

storing the physiological data into a medical record corresponding to the first user account;

receiving, from via a fifth graphical interface, a click of a consultation inlet displayed on the fifth graphical interface, wherein the click of the consultation inlet triggers a health consultation request of the first user account; and sending, together with the physiological data, the health consultation request of the user to a doctor terminal via a server, the doctor terminal being a user terminal of a healthcare provider, wherein the health consultation request is used to request the healthcare provider to provide health consultation service to the user based on the physiological data.

3. A non-transitory computer-readable storage medium, comprising computer program codes for executing:

displaying, by an intelligent device, a first graphical interface, wherein a third-party application program is installed on the intelligent device;

receiving, by the first graphical interface of the intelligent device, login information of a user account and a click of a login box displayed on the first graphical interface, the intelligent device having a memory and a processor;

after receiving the click of the login box displayed on the first graphical interface, displaying, by the intelligent device, a second graphical interface;

receiving, by the second graphical interface of the intelligent device, a binding instruction;

after receiving the binding instruction, establishing, by the intelligent device, a binding connection to a measurement device;

after the binding connection is established, receiving, by the intelligent device, a measurement value from the measurement device via a server;

displaying, on a third graphical interface, the measurement value corresponding to a level according to standard reference values in a measurement time period, the third graphical interface includes at least one of: a background color corresponding to the level, a control style corresponding to the level, a text description corresponding to the level, or an animation effect corresponding to the level;

obtaining, by the intelligent device, physiological data of a user based on the measurement value, wherein the obtaining the physiological data of the user comprises:

displaying, by a fourth graphical interface, multiple candidate calibration information identifiers;

receiving, via the fourth graphical interface of the intelligent device, a click selection for selecting the calibration information identifier among the candidate calibration information identifiers;

displaying, on the fourth graphical interface of the intelligent device, the calibration information identifier as selected;

obtaining, by the intelligent device, compensation information corresponding to the calibration information identifier, wherein the compensation information includes a first correspondence corresponding to the calibration information identifier being a first color and a second correspondence corresponding to the calibration information identifier being a second color different than the first color, and wherein each of the first and the second correspondences correlates measurement values respectively with compensation values;

displaying on the fourth graphical interface the first and the second correspondences, wherein a same measurement value correlates to different compensation information under the first and the second correspondences as displayed; and adjusting the measurement value according to the compensation information to obtain the physiological data of the user;

storing the physiological data into a medical record corresponding to the first user account;

receiving, via a fifth graphical interface of the intelligent device, a click of a consultation inlet displayed on the fifth graphical interface, wherein the click of the consultation inlet triggers a health consultation request of the first user account; and sending, together with the physiological data, the health consultation request of the user to a doctor terminal via a server, the doctor terminal being a user terminal of a healthcare provider, wherein the health consultation request is used to request the healthcare provider to provide health consultation service to the user based on the physiological data.

4. The method according to claim 1, wherein a binding key is positioned on the second graphical interface, and the method further comprises:

receiving, by the intelligent device, an activation of the binding key; and binding, by the intelligent device, the user account of the user on the intelligent device with a social account of the user or a different user, wherein the social account includes an instant messaging account.

5. The method according to claim 1, wherein the physiological data includes first and second physiological data, and obtaining the physiological data of the user comprises:
   obtaining at a first time point, by the intelligent device, the first physiological data of the user;
   obtaining at a second time point different than the first time point, by the intelligent device, the second physiological data of the user; and
   displaying, at the user interface of the intelligent device, a health inquiry recommendation according to a comparison of the second physiological data to the first physiological data.

6. The method according to claim 1, wherein the consultation inlet is a press-to-call button positioned on the fifth graphical interface, and the health consultation request is received by:
   receiving, by the intelligent device, an activation of the press-to-call button; and
   automatically generating, by the intelligent device, the health consultation request in response to receipt of the activation of the press-to-call button.

7. The method according to claim 1,
   wherein the intelligent device is separate from but in communication with the measurement device.

8. The method according to claim 1, wherein the multiple candidate calibration information identifiers include a first candidate calibration information identifier and a second calibration information identifier, and wherein displaying the multiple candidate calibration information identifiers comprises:
   displaying, on the fourth graphical interface of the first user terminal intelligent device, the first candidate calibration information identifier in a first display pattern; and
   displaying, on the fourth graphical interface of the intelligent device, the second candidate calibration information identifier in a second display pattern different than the first display pattern.

9. The method according to claim 1, further comprising:
   forwarding, by the intelligent device, the measurement value to a second user terminal of a relative of the user.

10. The method according to claim 1, wherein the measurement value is a first measurement value, the level is a first level, and the measurement time period is a first measurement time period, and wherein displaying the measurement value comprises:
    classifying, by the intelligent device, the first measurement value obtained in the first measurement period as the first level according to the standard reference values;
    storing, by the intelligent device, the first measurement value and the first level;
    classifying, by the intelligent device, a second measurement value obtained in a second measurement period as a second level according to the standard reference values;
    storing, by the intelligent device, the second measurement value and the second level; and
    displaying, on the third graphical interface of the intelligent device, the first level and the second level, the first level or the second level suggesting whether a trigger instruction is to be acted on the consultation inlet of the intelligent device.

11. The method according to claim 10, further comprising:
    in response to determining the second level suggests that the trigger instruction is to be acted on the consultation inlet, displaying, on the third graphical interface of the intelligent device, a color or a text to warn the user to act on the consultation inlet with the trigger instruction.

12. The method according to claim 1, wherein the health consultation request carries a contact method of the user to be forwarded to the doctor terminal.

13. The method according to claim 1, wherein adjusting the measurement value according to the compensation information to obtain the physiological data of the user comprises:
    obtaining, by the intelligent device, information on a test strip;
    converting, by the intelligent device, information on the test strip into an electric signal;
    displaying, on the user interface of the intelligent device, the measurement value according to the electric signal as converted.

14. The method according to claim 1, wherein the user is a first user and the user account is a first user account, and the method further comprises:
    storing, by the intelligent device, the first user account of the first user and a second user account of a second user;
    displaying, on the first graphical interface of the intelligent device, a first user account of the first user and the second user account of the second user;
    receiving, from the first graphical interface of the first user terminal intelligent device, a selection of the first user account; and
    after receiving the login information of the first user account, obtaining, by the intelligent device, a profile corresponding to the first user account.

15. The method according to claim 1, wherein selecting the calibration information identifier comprises:
    receiving a voice instruction as the selection instruction, and extracting the calibration information identifier carried in the voice instruction.

\* \* \* \* \*